(12) United States Patent
Slomczynska et al.

(10) Patent No.: US 8,809,344 B2
(45) Date of Patent: Aug. 19, 2014

(54) COMPOUNDS, COMPOSITIONS, AND METHODS FOR CONTROL OF HEPATITIS C VIRAL INFECTIONS

(75) Inventors: Urszula Slomczynska, Ballwin, MO (US); Paul Olivo, Clayton, MO (US); Jodi Beattie, Wentzville, MO (US); Gale Starkey, St. Louis, MO (US); Amine Noueiry, St. Louis, MO (US); Robert Roth, St. Louis, MO (US)

(73) Assignee: Apath, LLC, New York, NY (US)

( * ) Notice: Subject to any disclaimer, the term of this patent is extended or adjusted under 35 U.S.C. 154(b) by 356 days.

(21) Appl. No.: 13/126,619

(22) PCT Filed: Oct. 29, 2009

(86) PCT No.: PCT/US2009/062544
§ 371 (c)(1),
(2), (4) Date: Jul. 13, 2011

(87) PCT Pub. No.: WO2010/096115
PCT Pub. Date: Aug. 26, 2010

(65) Prior Publication Data
US 2011/0262397 A1 Oct. 27, 2011

Related U.S. Application Data

(60) Provisional application No. 61/109,372, filed on Oct. 29, 2008.

(51) Int. Cl.
*A61K 31/519* (2006.01)
(52) U.S. Cl.
USPC .................................. 514/259.1; 514/259.3
(58) Field of Classification Search
USPC .......................................... 514/259.1, 259.3
See application file for complete search history.

(56) References Cited

U.S. PATENT DOCUMENTS

| | | | |
|---|---|---|---|
| 4,122,278 | A | 10/1978 | Coispeau |
| 5,356,897 | A | 10/1994 | Oku et al. |
| 6,235,911 | B1 | 5/2001 | Yoshida et al. |
| 7,196,111 | B2 | 3/2007 | Shipps et al. |
| 2004/0121975 | A1 | 6/2004 | Gao et al. |
| 2007/0032488 | A1 | 2/2007 | Botyanszki et al. |
| 2007/0128625 | A1 | 6/2007 | Boddeker et al. |
| 2007/0167383 | A1 | 7/2007 | Roberts et al. |
| 2007/0265262 | A1 | 11/2007 | Schmitz et al. |
| 2007/0265265 | A1 | 11/2007 | Schmitz et al. |
| 2007/0269420 | A1 | 11/2007 | Chunduru et al. |
| 2007/0274951 | A1 | 11/2007 | Tong et al. |
| 2008/0045498 | A1 | 2/2008 | Griffith et al. |
| 2008/0051384 | A1 | 2/2008 | Schmitz et al. |
| 2008/0125367 | A1 | 5/2008 | Glenn et al. |
| 2008/0181866 | A1 | 7/2008 | Leivers et al. |
| 2008/0193411 | A1 | 8/2008 | Leivers et al. |
| 2010/0015093 | A1 | 1/2010 | Einav et al. |
| 2010/0028299 | A1 | 2/2010 | Einav et al. |

FOREIGN PATENT DOCUMENTS

| | | |
|---|---|---|
| JP | 2004277337 A | 10/2004 |
| WO | 93/17110 A2 | 9/1993 |
| WO | 2004017908 A2 | 3/2004 |
| WO | 2004037159 A2 | 5/2004 |
| WO | 2004089416 A2 | 10/2004 |
| WO | 2005051318 A2 | 6/2005 |
| WO | 2010/039195 A2 | 4/2010 |
| WO | 2010107739 A2 | 9/2010 |

OTHER PUBLICATIONS

Dalinger et al., "Liquid-Phase Synthesis of Combinatorial Libraries Based on 7-Trifluoromethyl-Substituted Pyrazolo [1,5-a] Pyrimidine Scaffold", J Comb. Chem. 2005, pp. 236-245, vol. 7.
Hwang, et al., "Solid-Phase Synthesis of 5-Amino-1 (Sustituted Thiocarbamoyl)pyrazole and 1,2,4-Triazole Derivatives via Dithiocarbazate Linker", J. Comb. Chem. 2005, pp. 136-141, vol. 7.
Kiessling et al.; Selective Inhibition of c-Myc/Max Dimerization and DNA Binding by Small Molecules. Chemistry & Biology, Jul. 2006, pp. 745-751, vol. 13(7), Cambridge, MA, United States.
Wilson et al., Solid Phase Synthesis of 5-Aminopyrazoles and Derivatives Part II, Tetrahedron Letters 39, 1998, pp. 2827-2830.
Zhou et al., Structure-Guided Optimization of Estrogen Receptor Binding Affinity and Antagonist Potency of Pyrazolopyrimidines with Basic Side Chains J. Med.Chem., 2007, pp. 399-403, vol. 50.
Rai et al, "New Opportunities in Anti-Hepatitis C Virus Drug Discovery: Targeting NS4B", Antiviral Research, 2011, pp. 93-101, vol. 90.
FDA News Release, "FDA Approves New Treatment for Hepatitis C Virus", Nov. 22, 2013, 3 pages, retrieved from <http://www.fda.gov/newsevents/newsroom/pressannouncements/ucm376449.htm> on Feb. 28, 2014.
FDA News Release, "FDA Approve Sovaldi for Chronic Hepatitis C", Dec. 6, 2013, 2 pages, retrieved from <http://www.fda.gov/newsevents/newsroom/pressannouncements/ucm377888.htm> on Feb. 28, 2014.
FDA News Release, "FDA Approves Victrelis for Hepatitis C", May 13, 2011, 3 pages, retrieved from <http://www.fda.gov/newsevents/newsroom/pressannouncements/ucm255390.htm> on Feb. 28, 2014.
Tong et al., "Preclinical Characterization of the Antiviral Activity of SCH 900518 (Narlaprevir), a Novel Mechanism-Based Inhibitor of Hepatitis C Virus NS3 Protease", Antimicrobial Agents and Chemotherapy, Jun. 2010, pp. 2365-2370, vol. 54 No. 6 [retrieved from http://aac.asm.org on Feb. 28, 2014].

*Primary Examiner* — Shengjun Wang
(74) *Attorney, Agent, or Firm* — Thompson Coburn LLP; Charles P. Romano

(57) ABSTRACT

Various tetrahydropyrazolo[1,5-a]pyrimidine compounds, compositions, methods of making, and methods for the prevention and treatment of HCV infections and associated diseases are disclosed. The invention further relates to biomarkers for identification of HCV strains which are resistant to the tetrahydropyrazolo[1,5-a]pyrimidine compounds.

6 Claims, 7 Drawing Sheets9

| AP Number | Structure |
|---|---|
| 0080978 (purified enantiomer) | Enantiomer 2 |
| 0089652 (racemate) | |
| 0088954 | 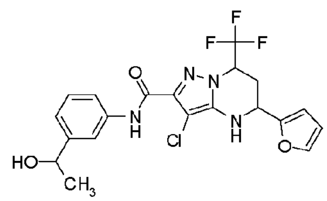 |
| 0080982 | 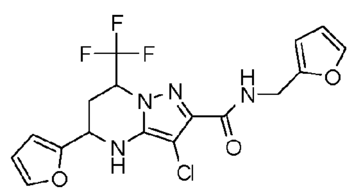 |
| 0083795 | 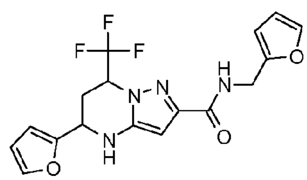 |
| 0084720 | 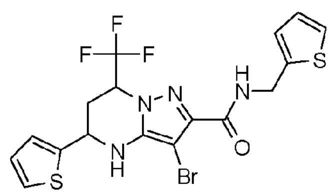 |
| 0080925 | 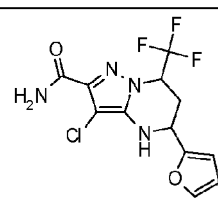 |

FIGURE 1

| AP Number | Structure | Formula | Molecular Weight | ClogP | EC50 (uM) | CC50 (uM) | Change from 80978 |
|---|---|---|---|---|---|---|---|
| 0080978 (purified enantiomer) | Enantiomer 2 | C17H14ClF3N4O2S | 430.8314 | 1.425 | 0.45 | | |
| 0089652 (racemate) | 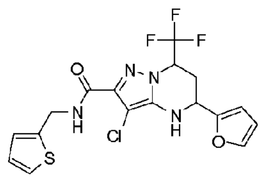 | C17H14ClF3N4O2S | 430.8314 | 1.426 | 0.9 | 100 | |
| 0088954 | 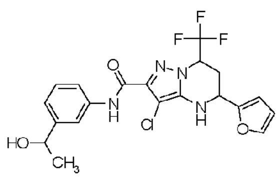 | C20H18ClF3N4O3 | 454.8354 | 0.872 | 2.54 | 26.22 | R3 |
| 0080982 | 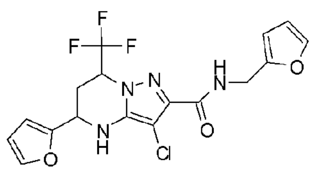 | C17H14ClF3N4O3 | 414.7708 | 0.956 | 4.69 | 100 | R3 |

FIGURE 2 (A)

| AP Number | Structure | Formula | Molecular Weight | ClogP | EC50 (uM) | CC50 (uM) | Change from 80978 |
|---|---|---|---|---|---|---|---|
| 0083795 | 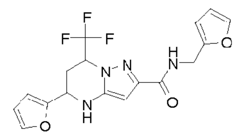 | C17H15F3N4O3 | 380.3257 | 1.051 | 6.51 | 100 | R3R4 |
| 0084720 | 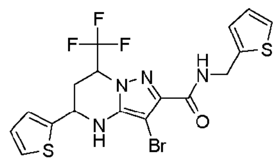 | C17H14BrF3N4OS2 | 491.343 | 1.956 | 16.58 | 83.93 | R1R4 |
| 0080925 | 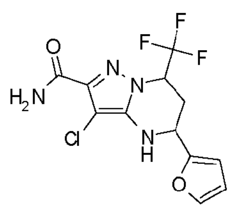 | C12H10ClF3N4O2 | 334.6848 | -0.4 | 20.2 | 100 | R3 |

(5S,7R)-3-chloro-5-(furan-2-yl)-N-(thiophen-2-ylmethyl)-7-(trifluoromethyl)-4,5,6,7-tetrahydropyrazolo[1,5-a]pyrimidine-2-carboxamide

80978 Inhibits Virus with a Sensitive NS4B

FIGURE 5

80978 Inactive Against Virus with Resistant NS4B

Treatment of APV23 with HCV antiviral compounds

Treatment of APV23 with 89652 analogs

FIGURE 6

SEQUENCE LISTING

<160> NUMBER OF SEQ ID NOS: 9

<210> SEQ ID NO 1
<211> LENGTH: 783
<212> TYPE: DNA
<213> ORGANISM: Hepatitis C virus
<220> FEATURE:
<221> NAME/KEY: CDS
<222> LOCATION: (1)..(783)

<400> SEQUENCE: 1

| | | | | | | | | | | | | | | | | |
|---|---|---|---|---|---|---|---|---|---|---|---|---|---|---|---|---|
| gcc | tca | cac | ctc | cct | tac | atc | gaa | cag | gga | atg | cag | ctc | gcc | gaa | caa | 48 |
| Ala | Ser | His | Leu | Pro | Tyr | Ile | Glu | Gln | Gly | Met | Gln | Leu | Ala | Glu | Gln | |
| 1 | | | | 5 | | | | | 10 | | | | | 15 | | |
| ttc | aaa | cag | aag | gca | atc | ggg | ttg | ctg | caa | aca | gcc | acc | aag | caa | gcg | 96 |
| Phe | Lys | Gln | Lys | Ala | Ile | Gly | Leu | Leu | Gln | Thr | Ala | Thr | Lys | Gln | Ala | |
| | | | 20 | | | | | 25 | | | | | 30 | | | |
| gag | gct | gct | gct | ccc | gtg | gtg | gaa | tcc | aag | tgg | cgg | acc | ctc | gaa | gcc | 144 |
| Glu | Ala | Ala | Ala | Pro | Val | Val | Glu | Ser | Lys | Trp | Arg | Thr | Leu | Glu | Ala | |
| | | | 35 | | | | | 40 | | | | | 45 | | | |
| ttc | tgg | gcg | aag | cat | atg | tgg | aat | ttc | atc | agc | ggg | ata | caa | tat | tta | 192 |
| Phe | Trp | Ala | Lys | His | Met | Trp | Asn | Phe | Ile | Ser | Gly | Ile | Gln | Tyr | Leu | |
| | | 50 | | | | | 55 | | | | | 60 | | | | |
| gca | ggc | ttg | tcc | act | ctg | cct | ggc | aac | ccc | gcg | ata | gca | tca | ctg | atg | 240 |
| Ala | Gly | Leu | Ser | Thr | Leu | Pro | Gly | Asn | Pro | Ala | Ile | Ala | Ser | Leu | Met | |
| 65 | | | | | 70 | | | | | 75 | | | | | 80 | |
| gca | ttc | aca | gcc | tct | atc | acc | agc | ccg | ctc | acc | acc | caa | cat | acc | ctc | 288 |
| Ala | Phe | Thr | Ala | Ser | Ile | Thr | Ser | Pro | Leu | Thr | Thr | Gln | His | Thr | Leu | |
| | | | | 85 | | | | | 90 | | | | | 95 | | |
| ctg | ttt | aac | atc | ctg | ggg | gga | tgg | gtg | gcc | gcc | caa | ctt | gct | cct | ccc | 336 |
| Leu | Phe | Asn | Ile | Leu | Gly | Gly | Trp | Val | Ala | Ala | Gln | Leu | Ala | Pro | Pro | |
| | | | 100 | | | | | 105 | | | | | 110 | | | |
| agc | gct | gct | tct | gct | ttc | gta | ggc | gcc | ggc | atc | gct | gga | gcg | gct | gtt | 384 |
| Ser | Ala | Ala | Ser | Ala | Phe | Val | Gly | Ala | Gly | Ile | Ala | Gly | Ala | Ala | Val | |
| | | | | 115 | | | | | 120 | | | | | 125 | | |
| ggc | agc | ata | ggc | ctt | ggg | aag | gtg | ctt | gtg | gat | att | ttg | gca | ggt | tat | 432 |
| Gly | Ser | Ile | Gly | Leu | Gly | Lys | Val | Leu | Val | Asp | Ile | Leu | Ala | Gly | Tyr | |
| | 130 | | | | | 135 | | | | | 140 | | | | | |
| gga | gca | ggg | gtg | gca | ggc | gcg | ctc | gtg | gcc | ttt | aag | gtc | atg | agc | ggc | 480 |
| Gly | Ala | Gly | Val | Ala | Gly | Ala | Leu | Val | Ala | Phe | Lys | Val | Met | Ser | Gly | |
| 145 | | | | | 150 | | | | | 155 | | | | | 160 | |
| gag | atg | ccc | tcc | acc | gag | gac | ctg | gtt | aac | cta | ctc | cct | gct | atc | ctc | 528 |
| Glu | Met | Pro | Ser | Thr | Glu | Asp | Leu | Val | Asn | Leu | Leu | Pro | Ala | Ile | Leu | |
| | | | | 165 | | | | | 170 | | | | | 175 | | |
| tcc | cct | ggc | gcc | cta | gtc | gtc | ggg | gtc | gtg | tgc | gca | gcg | ata | ctg | cgt | 576 |
| Ser | Pro | Gly | Ala | Leu | Val | Val | Gly | Val | Val | Cys | Ala | Ala | Ile | Leu | Arg | |
| | | | 180 | | | | | 185 | | | | | 190 | | | |
| cgg | cac | gtg | ggc | cca | ggg | gag | ggg | gct | gtg | cag | tgg | atg | aac | cgg | ctg | 624 |
| Arg | His | Val | Gly | Pro | Gly | Glu | Gly | Ala | Val | Gln | Trp | Met | Asn | Arg | Leu | |
| | | 195 | | | | | 200 | | | | | 205 | | | | |
| ata | gcg | ttc | gct | tcg | cgg | ggt | aac | cac | gtc | tcc | ccc | acg | cac | tat | gtg | 672 |
| Ile | Ala | Phe | Ala | Ser | Arg | Gly | Asn | His | Val | Ser | Pro | Thr | His | Tyr | Val | |
| | 210 | | | | | 215 | | | | | 220 | | | | | |
| cct | gag | agc | gac | gct | gca | gca | cgt | gtc | act | cag | atc | ctc | tct | agt | ctt | 720 |
| Pro | Glu | Ser | Asp | Ala | Ala | Ala | Arg | Val | Thr | Gln | Ile | Leu | Ser | Ser | Leu | |
| 225 | | | | | 230 | | | | | 235 | | | | | 240 | |
| acc | atc | act | cag | ctg | ctg | aag | agg | ctt | cac | cag | tgg | atc | aac | gag | gac | 768 |
| Thr | Ile | Thr | Gln | Leu | Leu | Lys | Arg | Leu | His | Gln | Trp | Ile | Asn | Glu | Asp | |
| | | | | 245 | | | | | 250 | | | | | 255 | | |
| tgc | tcc | acg | cca | tgc | | | | | | | | | | | | 783 |
| Cys | Ser | Thr | Pro | Cys | | | | | | | | | | | | |
| | | | 260 | | | | | | | | | | | | | |

<210> SEQ ID NO 2
<211> LENGTH: 261
<212> TYPE: PRT
<213> ORGANISM: Hepatitis C virus

<400> SEQUENCE: 2

Ala Ser His Leu Pro Tyr Ile Glu Gln Gly Met Gln Leu Ala Glu Gln
1               5                   10                  15

```
Phe Lys Gln Lys Ala Ile Gly Leu Leu Gln Thr Ala Thr Lys Gln Ala
                20                  25                  30

Glu Ala Ala Ala Pro Val Val Glu Ser Lys Trp Arg Thr Leu Glu Ala
            35                  40                  45

Phe Trp Ala Lys His Met Trp Asn Phe Ile Ser Gly Ile Gln Tyr Leu
        50                  55                  60

Ala Gly Leu Ser Thr Leu Pro Gly Asn Pro Ala Ile Ala Ser Leu Met
65                  70                  75                  80

Ala Phe Thr Ala Ser Ile Thr Ser Pro Leu Thr Thr Gln His Thr Leu
                85                  90                  95

Leu Phe Asn Ile Leu Gly Gly Trp Val Ala Ala Gln Leu Ala Pro Pro
            100                 105                 110

Ser Ala Ala Ser Ala Phe Val Gly Ala Gly Ile Ala Gly Ala Ala Val
        115                 120                 125

Gly Ser Ile Gly Leu Gly Lys Val Leu Val Asp Ile Leu Ala Gly Tyr
    130                 135                 140

Gly Ala Gly Val Ala Gly Ala Leu Val Ala Phe Lys Val Met Ser Gly
145                 150                 155                 160

Glu Met Pro Ser Thr Glu Asp Leu Val Asn Leu Leu Pro Ala Ile Leu
                165                 170                 175

Ser Pro Gly Ala Leu Val Val Gly Val Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260

<210> SEQ ID NO 3
<211> LENGTH: 783
<212> TYPE: DNA
<213> ORGANISM: Hepatitis C virus
<220> FEATURE:
<221> NAME/KEY: CDS
<222> LOCATION: (1)..(783)

<400> SEQUENCE: 3 gcc tca cac ctc cct tac atc gaa cag gga atg cag ctc gcc gaa caa      48
Ala Ser His Leu Pro Tyr Ile Glu Gln Gly Met Gln Leu Ala Glu Gln
1               5                   10                  15 ttc aaa cag aag gca atc ggg ttg ctg caa aca gcc acc aag caa gcg      96
Phe Lys Gln Lys Ala Ile Gly Leu Leu Gln Thr Ala Thr Lys Gln Ala
                20                  25                  30 gag gct gct gct ccc gtg gtg gaa tcc aag tgg cgg acc ctc gaa gcc     144
Glu Ala Ala Ala Pro Val Val Glu Ser Lys Trp Arg Thr Leu Glu Ala
            35                  40                  45 ttc tgg gcg aag cat atg tgg aat ttc atc agc ggg ata caa tat tta     192
Phe Trp Ala Lys His Met Trp Asn Phe Ile Ser Gly Ile Gln Tyr Leu
        50                  55                  60 gca ggc ttg tcc act ctg cct ggc aac ccc gcg ata gca tca ctg atg     240
Ala Gly Leu Ser Thr Leu Pro Gly Asn Pro Ala Ile Ala Ser Leu Met
65                  70                  75                  80
```

| | | | | | | | | | | | | | | |
|---|---|---|---|---|---|---|---|---|---|---|---|---|---|---|
| gca | ttc | aca | gcc | tct | atc | acc | agc | ccg | ctc | acc | acc | caa | cat | acc ctc | 288 |
| Ala | Phe | Thr | Ala | Ser | Ile | Thr | Ser | Pro | Leu | Thr | Thr | Gln | His | Thr Leu | |
| | | | 85 | | | | | 90 | | | | | 95 | | | ctg gtt aac atc ctg ggg gga tgg gtg gcc gcc caa ctt gct cct ccc   336
Leu Val Asn Ile Leu Gly Gly Trp Val Ala Ala Gln Leu Ala Pro Pro
            100                 105                 110 agc gct gct tct gct ttc gta ggc gcc ggc atc gct gga gcg gct gtt   384
Ser Ala Ala Ser Ala Phe Val Gly Ala Gly Ile Ala Gly Ala Ala Val
                115                 120                 125 ggc agc ata ggc ctt ggg aag gtg ctt gtg gat att ttg gca ggt tat   432
Gly Ser Ile Gly Leu Gly Lys Val Leu Val Asp Ile Leu Ala Gly Tyr
        130                 135                 140 gga gca ggg gtg gca ggc gcg ctc gtg gcc ttt aag gtc atg agc ggc   480
Gly Ala Gly Val Ala Gly Ala Leu Val Ala Phe Lys Val Met Ser Gly
145                 150                 155                 160 gag atg ccc tcc acc gag gac ctg gtt aac cta ctc cct gct atc ctc   528
Glu Met Pro Ser Thr Glu Asp Leu Val Asn Leu Leu Pro Ala Ile Leu
                165                 170                 175 tcc cct ggc gcc cta gtc gtc ggg gtc gtg tgc gca gcg ata ctg cgt   576
Ser Pro Gly Ala Leu Val Val Gly Val Val Cys Ala Ala Ile Leu Arg
            180                 185                 190 cgg cac gtg ggc cca ggg gag ggg gct gtg cag tgg atg aac cgg ctg   624
Arg His Val Gly Pro Gly Glu Gly Ala Val Gln Trp Met Asn Arg Leu
        195                 200                 205 ata gcg ttc gct tcg cgg ggt aac cac gtc tcc ccc acg cac tat gtg   672
Ile Ala Phe Ala Ser Arg Gly Asn His Val Ser Pro Thr His Tyr Val
    210                 215                 220 cct gag agc gac gct gca gca cgt gtc act cag atc ctc tct agt ctt   720
Pro Glu Ser Asp Ala Ala Ala Arg Val Thr Gln Ile Leu Ser Ser Leu
225                 230                 235                 240 acc atc act cag ctg ctg aag agg ctt cac cag tgg atc aac gag gac   768
Thr Ile Thr Gln Leu Leu Lys Arg Leu His Gln Trp Ile Asn Glu Asp
                245                 250                 255 tgc tcc acg cca tgc                                               783
Cys Ser Thr Pro Cys
            260

```
<210> SEQ ID NO 4
<211> LENGTH: 261
<212> TYPE: PRT
<213> ORGANISM: Hepatitis C virus

<400> SEQUENCE: 4
```

Ala Ser His Leu Pro Tyr Ile Glu Gln Gly Met Gln Leu Ala Glu Gln
1               5                   10                  15

Phe Lys Gln Lys Ala Ile Gly Leu Leu Gln Thr Ala Thr Lys Gln Ala
                20                  25                  30

Glu Ala Ala Ala Pro Val Val Glu Ser Lys Trp Arg Thr Leu Glu Ala
            35                  40                  45

Phe Trp Ala Lys His Met Trp Asn Phe Ile Ser Gly Ile Gln Tyr Leu
        50                  55                  60

Ala Gly Leu Ser Thr Leu Pro Gly Asn Pro Ala Ile Ala Ser Leu Met
65                  70                  75                  80

Ala Phe Thr Ala Ser Ile Thr Ser Pro Leu Thr Thr Gln His Thr Leu
                85                  90                  95

Leu Val Asn Ile Leu Gly Gly Trp Val Ala Ala Gln Leu Ala Pro Pro
            100                 105                 110

Ser Ala Ala Ser Ala Phe Val Gly Ala Gly Ile Ala Gly Ala Ala Val
        115                 120                 125

```
Gly Ser Ile Gly Leu Gly Lys Val Leu Val Asp Ile Leu Ala Gly Tyr
        130                 135                 140

Gly Ala Gly Val Ala Gly Ala Leu Val Ala Phe Lys Val Met Ser Gly
145                 150                 155                 160

Glu Met Pro Ser Thr Glu Asp Leu Val Asn Leu Leu Pro Ala Ile Leu
                165                 170                 175

Ser Pro Gly Ala Leu Val Val Gly Val Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260

<210> SEQ ID NO 5
<211> LENGTH: 783
<212> TYPE: DNA
<213> ORGANISM: Hepatitis C virus
<220> FEATURE:
<221> NAME/KEY: CDS
<222> LOCATION: (1)..(783)

<400> SEQUENCE: 5 gcc tca cac ctc cct tac atc gaa cag gga atg cag ctc gcc gaa caa      48
Ala Ser His Leu Pro Tyr Ile Glu Gln Gly Met Gln Leu Ala Glu Gln
1               5                   10                  15 ttc aaa cag aag gca atc ggg ttg ctg caa aca gcc acc aag caa gcg      96
Phe Lys Gln Lys Ala Ile Gly Leu Leu Gln Thr Ala Thr Lys Gln Ala
            20                  25                  30 gag gct gct gct ccc gtg gtg gaa tcc aag tgg cgg acc ctc gaa gcc     144
Glu Ala Ala Ala Pro Val Val Glu Ser Lys Trp Arg Thr Leu Glu Ala
        35                  40                  45 ttc tgg gcg aag cat atg tgg aat ttc atc agc ggg ata caa tat tta     192
Phe Trp Ala Lys His Met Trp Asn Phe Ile Ser Gly Ile Gln Tyr Leu
    50                  55                  60 gca ggc ttg tcc act ctg cct ggc aac ccc gcg ata gca tca ctg atg     240
Ala Gly Leu Ser Thr Leu Pro Gly Asn Pro Ala Ile Ala Ser Leu Met
65                  70                  75                  80 gca ttc aca gcc tct atc acc agc ccg ctc acc acc caa cat acc ctc     288
Ala Phe Thr Ala Ser Ile Thr Ser Pro Leu Thr Thr Gln His Thr Leu
                85                  90                  95 ctg ctt aac atc ctg ggg gga tgg gtg gcc gcc caa ctt gct cct ccc     336
Leu Leu Asn Ile Leu Gly Gly Trp Val Ala Ala Gln Leu Ala Pro Pro
            100                 105                 110 agc gct gct tct gct ttc gta ggc gcc ggc atc gct gga gcg gct gtt     384
Ser Ala Ala Ser Ala Phe Val Gly Ala Gly Ile Ala Gly Ala Ala Val
        115                 120                 125 ggc agc ata ggc ctt ggg aag gtg ctt gtg gat att ttg gca ggt tat     432
Gly Ser Ile Gly Leu Gly Lys Val Leu Val Asp Ile Leu Ala Gly Tyr
    130                 135                 140 gga gca ggg gtg gca ggc gcg ctc gtg gcc ttt aag gtc atg agc ggc     480
Gly Ala Gly Val Ala Gly Ala Leu Val Ala Phe Lys Val Met Ser Gly
145                 150                 155                 160
```

```
gag atg ccc tcc acc gag gac ctg gtt aac cta ctc cct gct atc ctc    528
Glu Met Pro Ser Thr Glu Asp Leu Val Asn Leu Leu Pro Ala Ile Leu
            165                 170                 175 tcc cct ggc gcc cta gtc gtc ggg gtc gtg tgc gca gcg ata ctg cgt    576
Ser Pro Gly Ala Leu Val Val Gly Val Val Cys Ala Ala Ile Leu Arg
        180                 185                 190 cgg cac gtg ggc cca ggg gag ggg gct gtg cag tgg atg aac cgg ctg    624
Arg His Val Gly Pro Gly Glu Gly Ala Val Gln Trp Met Asn Arg Leu
            195                 200                 205 ata gcg ttc gct tcg cgg ggt aac cac gtc tcc ccc acg cac tat gtg    672
Ile Ala Phe Ala Ser Arg Gly Asn His Val Ser Pro Thr His Tyr Val
210                 215                 220 cct gag agc gac gct gca gca cgt gtc act cag atc ctc tct agt ctt    720
Pro Glu Ser Asp Ala Ala Ala Arg Val Thr Gln Ile Leu Ser Ser Leu
225                 230                 235                 240 acc atc act cag ctg ctg aag agg ctt cac cag tgg atc aac gag gac    768
Thr Ile Thr Gln Leu Leu Lys Arg Leu His Gln Trp Ile Asn Glu Asp
                245                 250                 255 tgc tcc acg cca tgc                                                783
Cys Ser Thr Pro Cys
            260
```

<210> SEQ ID NO 6
<211> LENGTH: 261
<212> TYPE: PRT
<213> ORGANISM: Hepatitis C virus

<400> SEQUENCE: 6

```
Ala Ser His Leu Pro Tyr Ile Glu Gln Gly Met Gln Leu Ala Glu Gln
1               5                   10                  15

Phe Lys Gln Lys Ala Ile Gly Leu Leu Gln Thr Ala Thr Lys Gln Ala
                20                  25                  30

Glu Ala Ala Ala Pro Val Val Glu Ser Lys Trp Arg Thr Leu Glu Ala
            35                  40                  45

Phe Trp Ala Lys His Met Trp Asn Phe Ile Ser Gly Ile Gln Tyr Leu
        50                  55                  60

Ala Gly Leu Ser Thr Leu Pro Gly Asn Pro Ala Ile Ala Ser Leu Met
65                  70                  75                  80

Ala Phe Thr Ala Ser Ile Thr Ser Pro Leu Thr Thr Gln His Thr Leu
                85                  90                  95

Leu Leu Asn Ile Leu Gly Gly Trp Val Ala Ala Gln Leu Ala Pro Pro
            100                 105                 110

Ser Ala Ala Ser Ala Phe Val Gly Ala Gly Ile Ala Gly Ala Ala Val
        115                 120                 125

Gly Ser Ile Gly Leu Gly Lys Val Leu Val Asp Ile Leu Ala Gly Tyr
130                 135                 140

Gly Ala Gly Val Ala Gly Ala Leu Val Ala Phe Lys Val Met Ser Gly
145                 150                 155                 160

Glu Met Pro Ser Thr Glu Asp Leu Val Asn Leu Leu Pro Ala Ile Leu
                165                 170                 175

Ser Pro Gly Ala Leu Val Val Gly Val Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
210                 215                 220
```

```
Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260

<210> SEQ ID NO 7
<211> LENGTH: 783
<212> TYPE: DNA
<213> ORGANISM: Hepatitis C virus
<220> FEATURE:
<221> NAME/KEY: CDS
<222> LOCATION: (1)..(783)

<400> SEQUENCE: 7 gcc tct agg gcg gct ctc atc gaa gag ggg cag cgg ata gcc gag atg      48
Ala Ser Arg Ala Ala Leu Ile Glu Glu Gly Gln Arg Ile Ala Glu Met
1               5                   10                  15 ttg aag tcc aag atc caa ggc ttg ctg cag cag gcc tcg aag cag gcc      96
Leu Lys Ser Lys Ile Gln Gly Leu Leu Gln Gln Ala Ser Lys Gln Ala
            20                  25                  30 cag gac ata caa ccc gct atg cag gct tca tgg ccc aaa gtg gaa caa     144
Gln Asp Ile Gln Pro Ala Met Gln Ala Ser Trp Pro Lys Val Glu Gln
        35                  40                  45 ttt tgg gcc aga cac atg tgg aac ttc att agc ggc atc caa tac ctc     192
Phe Trp Ala Arg His Met Trp Asn Phe Ile Ser Gly Ile Gln Tyr Leu
    50                  55                  60 gca gga ttg tca aca ctg cca ggg aac ccc gcg gtg gct tcc atg atg     240
Ala Gly Leu Ser Thr Leu Pro Gly Asn Pro Ala Val Ala Ser Met Met
65                  70                  75                  80 gca ttc agt gcc gcc ctc acc agt ccg ttg tcg acc agt acc acc atc     288
Ala Phe Ser Ala Ala Leu Thr Ser Pro Leu Ser Thr Ser Thr Thr Ile
                85                  90                  95 ctt ctc aac atc atg gga ggc tgg tta gcg tcc cag atc gca cca ccc     336
Leu Leu Asn Ile Met Gly Gly Trp Leu Ala Ser Gln Ile Ala Pro Pro
            100                 105                 110 gcg ggg gcc acc ggc ttt gtc gtc agt ggc ctg gtg ggg gct gcc gtg     384
Ala Gly Ala Thr Gly Phe Val Val Ser Gly Leu Val Gly Ala Ala Val
        115                 120                 125 ggc agc ata ggc ctg ggt aag gtg ctg gtg gac atc ctg gca gga tat     432
Gly Ser Ile Gly Leu Gly Lys Val Leu Val Asp Ile Leu Ala Gly Tyr
    130                 135                 140 ggt gcg ggc att tcg ggg gcc ctc gtc gca ttc aag atc atg tct ggc     480
Gly Ala Gly Ile Ser Gly Ala Leu Val Ala Phe Lys Ile Met Ser Gly
145                 150                 155                 160 gag aag ccc tct atg gaa gat gtc atc aat cta ctg cct ggg atc ctg     528
Glu Lys Pro Ser Met Glu Asp Val Ile Asn Leu Leu Pro Gly Ile Leu
                165                 170                 175 tct ccg gga gcc ctg gtg gtg ggg gtc atc tgc gcg gcc att ctg cgc     576
Ser Pro Gly Ala Leu Val Val Gly Val Ile Cys Ala Ala Ile Leu Arg
            180                 185                 190 cgc cac gtg gga ccg ggg gag ggc gcg gtc caa tgg atg aac agg ctt     624
Arg His Val Gly Pro Gly Glu Gly Ala Val Gln Trp Met Asn Arg Leu
        195                 200                 205 att gcc ttt gct tcc aga gga aac cac gtc gcc cct act cac tac gtg     672
Ile Ala Phe Ala Ser Arg Gly Asn His Val Ala Pro Thr His Tyr Val
    210                 215                 220 acg gag tcg gat gcg tcg cag cgt gtg acc caa cta ctt ggc tct ctt     720
Thr Glu Ser Asp Ala Ser Gln Arg Val Thr Gln Leu Leu Gly Ser Leu
225                 230                 235                 240
```

```
act ata acc agc cta ctc aga aga ctc cac aat tgg ata act gag gac    768
Thr Ile Thr Ser Leu Leu Arg Arg Leu His Asn Trp Ile Thr Glu Asp
            245                 250                 255 tgc ccc atc cca tgc                                                783
Cys Pro Ile Pro Cys
            260

<210> SEQ ID NO 8
<211> LENGTH: 261
<212> TYPE: PRT
<213> ORGANISM: Hepatitis C virus

<400> SEQUENCE: 8

Ala Ser Arg Ala Ala Leu Ile Glu Glu Gly Gln Arg Ile Ala Glu Met
1               5                   10                  15

Leu Lys Ser Lys Ile Gln Gly Leu Leu Gln Gln Ala Ser Lys Gln Ala
            20                  25                  30

Gln Asp Ile Gln Pro Ala Met Gln Ala Ser Trp Pro Lys Val Glu Gln
        35                  40                  45

Phe Trp Ala Arg His Met Trp Asn Phe Ile Ser Gly Ile Gln Tyr Leu
    50                  55                  60

Ala Gly Leu Ser Thr Leu Pro Gly Asn Pro Ala Val Ala Ser Met Met
65                  70                  75                  80

Ala Phe Ser Ala Ala Leu Thr Ser Pro Leu Ser Thr Ser Thr Thr Ile
                85                  90                  95

Leu Leu Asn Ile Met Gly Gly Trp Leu Ala Ser Gln Ile Ala Pro Pro
            100                 105                 110

Ala Gly Ala Thr Gly Phe Val Val Ser Gly Leu Val Gly Ala Ala Val
        115                 120                 125

Gly Ser Ile Gly Leu Gly Lys Val Leu Val Asp Ile Leu Ala Gly Tyr
    130                 135                 140

Gly Ala Gly Ile Ser Gly Ala Leu Val Ala Phe Lys Ile Met Ser Gly
145                 150                 155                 160

Glu Lys Pro Ser Met Glu Asp Val Ile Asn Leu Leu Pro Gly Ile Leu
                165                 170                 175

Ser Pro Gly Ala Leu Val Val Gly Val Ile Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ala Pro Thr His Tyr Val
    210                 215                 220

Thr Glu Ser Asp Ala Ser Gln Arg Val Thr Gln Leu Leu Gly Ser Leu
225                 230                 235                 240

Thr Ile Thr Ser Leu Leu Arg Arg Leu His Asn Trp Ile Thr Glu Asp
                245                 250                 255

Cys Pro Ile Pro Cys
            260

<210> SEQ ID NO 9
<211> LENGTH: 3010
<212> TYPE: PRT
<213> ORGANISM: Hepatitis C virus

<400> SEQUENCE: 9

Met Ser Thr Asn Pro Lys Pro Gln Arg Lys Thr Lys Arg Asn Thr Asn
1               5                   10                  15
```

-continued

```
Arg Arg Pro Gln Asp Val Lys Phe Pro Gly Gly Gln Ile Val Gly
         20                  25                  30
Gly Val Tyr Leu Leu Pro Arg Arg Gly Pro Arg Leu Gly Val Arg Ala
         35                  40                  45
Thr Arg Lys Thr Ser Glu Arg Ser Gln Pro Arg Gly Arg Arg Gln Pro
     50                  55                  60
Ile Pro Lys Ala Arg Gln Pro Glu Gly Arg Ala Trp Ala Gln Pro Gly
65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Thr Asp Pro
            100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Leu
        130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Ile Pro Ala Ser Ala Tyr
            180                 185                 190
Glu Val Arg Asn Val Ser Gly Val Tyr His Val Thr Asn Asp Cys Ser
            195                 200                 205
Asn Ala Ser Ile Val Tyr Glu Ala Ala Asp Met Ile Met His Thr Pro
210                 215                 220
Gly Cys Val Pro Cys Val Arg Glu Asn Asn Ser Ser Arg Cys Trp Val
225                 230                 235                 240
Ala Leu Thr Pro Thr Leu Ala Ala Arg Asn Ala Ser Val Pro Thr Thr
                245                 250                 255
Thr Ile Arg Arg His Val Asp Leu Leu Val Gly Ala Ala Ala Leu Cys
            260                 265                 270
Ser Ala Met Tyr Val Gly Asp Leu Cys Gly Ser Val Phe Leu Val Ala
        275                 280                 285
Gln Leu Phe Thr Phe Ser Pro Arg Arg His Glu Thr Val Gln Asp Cys
    290                 295                 300
Asn Cys Ser Ile Tyr Pro Gly His Val Thr Gly His Arg Met Ala Trp
305                 310                 315                 320
Asp Met Met Met Asn Trp Ser Pro Thr Ala Ala Leu Val Val Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Val Gly Asn Trp
        355                 360                 365
Ala Lys Val Leu Ile Val Met Leu Leu Phe Ala Gly Val Asp Gly Gly
        370                 375                 380
Thr Tyr Val Thr Gly Gly Thr Met Ala Lys Asn Thr Leu Gly Ile Thr
385                 390                 395                 400
Ser Leu Phe Ser Pro Gly Ser Ser Gln Lys Ile Gln Leu Val Asn Thr
                405                 410                 415
Asn Gly Ser Trp His Ile Asn Arg Thr Ala Leu Asn Cys Asn Asp Ser
            420                 425                 430
```

```
Leu Asn Thr Gly Phe Leu Ala Ala Leu Phe Tyr Val His Lys Phe Asn
            435                 440                 445

Ser Ser Gly Cys Pro Glu Arg Met Ala Ser Cys Ser Pro Ile Asp Ala
450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
                500                 505                 510

Pro Val Val Val Gly Thr Thr Asp Arg Phe Gly Val Pro Thr Tyr Ser
            515                 520                 525

Trp Gly Glu Asn Glu Thr Asp Val Leu Leu Asn Asn Thr Arg Pro
            530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ile Gly Asn
                565                 570                 575

Lys Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
            595                 600                 605

Val His Tyr Pro Tyr Arg Leu Trp His Tyr Pro Cys Thr Val Asn Phe
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
                660                 665                 670

Gln Val Leu Pro Cys Ser Phe Thr Thr Leu Pro Ala Leu Ser Thr Gly
            675                 680                 685

Leu Ile His Leu His Gln Asn Val Val Asp Val Gln Tyr Leu Tyr Gly
            690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
                740                 745                 750

Val Leu Asn Ala Ala Ser Val Ala Gly Ala His Gly Ile Leu Ser Phe
            755                 760                 765

Leu Val Phe Phe Cys Ala Ala Trp Tyr Ile Lys Gly Arg Leu Val Pro
            770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Ile Leu Leu Thr Leu Ser
                820                 825                 830

Pro His Tyr Lys Leu Phe Leu Ala Arg Leu Ile Trp Trp Leu Gln Tyr
            835                 840                 845
```

-continued

```
Phe Ile Thr Arg Ala Glu Ala His Leu Gln Val Trp Ile Pro Pro Leu
850                 855                 860

Asn Val Arg Gly Gly Arg Asp Ala Val Ile Leu Leu Thr Cys Ala Ile
865                 870                 875                 880

His Pro Glu Leu Ile Phe Thr Ile Thr Lys Ile Leu Leu Ala Ile Leu
                    885                 890                 895

Gly Pro Leu Met Val Leu Gln Ala Gly Ile Thr Lys Val Pro Tyr Phe
                900                 905                 910

Val Arg Ala His Gly Leu Ile Arg Ala Cys Met Leu Val Arg Lys Val
                915                 920                 925

Ala Gly Gly His Tyr Val Gln Met Ala Leu Met Lys Leu Ala Ala Leu
930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Asp Met Glu Thr Lys Val Ile Thr Trp Gly Ala Asp Thr Ala Ala
                980                 985                 990

Cys Gly Asp Ile Ile Leu Gly Leu Pro Val Ser Ala Arg Arg Gly Arg
                995                 1000                1005

Glu Ile His Leu Gly Pro Ala Asp Ser Leu Glu Gly Gln Gly Trp
    1010                1015                1020

Arg Leu Leu Ala Pro Ile Thr Ala Tyr Ser Gln Gln Thr Arg Gly
    1025                1030                1035

Leu Leu Gly Cys Ile Ile Thr Ser Leu Thr Gly Arg Asp Arg Asn
    1040                1045                1050

Gln Val Glu Gly Glu Val Gln Val Val Ser Thr Ala Thr Gln Ser
    1055                1060                1065

Phe Leu Ala Thr Cys Val Asn Gly Val Cys Trp Thr Val Tyr His
    1070                1075                1080

Gly Ala Gly Ser Lys Thr Leu Ala Gly Pro Lys Gly Pro Ile Thr
    1085                1090                1095

Gln Met Tyr Thr Asn Val Asp Gln Asp Leu Val Gly Trp Gln Ala
    1100                1105                1110

Pro Pro Gly Ala Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Val
    1145                1150                1155

Ser Tyr Leu Lys Gly Ser Ser Gly Gly Pro Leu Leu Cys Pro Ser
    1160                1165                1170

Gly His Ala Val Gly Ile Phe Arg Ala Ala Val Cys Thr Arg Gly
    1175                1180                1185

Val Ala Lys Ala Val Asp Phe Val Pro Val Glu Ser Met Glu Thr
    1190                1195                1200

Thr Met Arg Ser Pro Val Phe Thr Asp Asn Ser Ser Pro Pro Ala
    1205                1210                1215

Val Pro Gln Thr Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245
```

-continued

```
Tyr Lys Val Leu Val Leu Asn Pro Ser Val Ala Ala Thr Leu Gly
    1250                1255                1260

Phe Gly Ala Tyr Met Ser Lys Ala His Gly Ile Asp Pro Asn Ile
    1265                1270                1275

Arg Thr Gly Val Arg Thr Ile Thr Thr Gly Ala Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ser
    1310                1315                1320

Thr Thr Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Pro His Pro Asn Ile Glu Glu Val Ala Leu Ser
    1355                1360                1365

Ser Thr Gly Glu Ile Pro Phe Tyr Gly Lys Ala Ile Pro Ile Glu
    1370                1375                1380

Thr Ile Lys Gly Gly Arg His Leu Ile Phe Cys His Ser Lys Lys
    1385                1390                1395

Lys Cys Asp Glu Leu Ala Ala Lys Leu Ser Gly Leu Gly Leu Asn
    1400                1405                1410

Ala Val Ala Tyr Tyr Arg Gly Leu Asp Val Ser Val Ile Pro Thr
    1415                1420                1425

Ser Gly Asp Val Ile Val Val Ala Thr Asp Ala Leu Met Thr Gly
    1430                1435                1440

Phe Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Val Pro Gln Asp Ala Val Ser Arg Ser Gln Arg Arg
    1475                1480                1485

Gly Arg Thr Gly Arg Gly Arg Met Gly Ile Tyr Arg Phe Val Thr
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Ser Val Arg Leu Arg Ala Tyr Leu Asn Thr Pro Gly Leu
    1535                1540                1545

Pro Val Cys Gln Asp His Leu Glu Phe Trp Glu Ser Val Phe Thr
    1550                1555                1560

Gly Leu Thr His Ile Asp Ala His Phe Leu Ser Gln Thr Lys Gln
    1565                1570                1575

Ala Gly Asp Asn Phe Pro Tyr Leu Val Ala Tyr Gln Ala Thr Val
    1580                1585                1590

Cys Ala Arg Ala Gln Ala Pro Pro Pro Ser Trp Asp Gln Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ala Val Gln Asn Glu Val Thr Thr Thr
    1625                1630                1635
```

-continued

```
His Pro Ile Thr Lys Tyr Ile Met Ala Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Thr Thr Gly Ser Val Val Ile Val
    1670                1675                1680

Gly Arg Ile Ile Leu Ser Gly Lys Pro Ala Ile Ile Pro Asp Arg
    1685                1690                1695

Glu Val Leu Tyr Arg Glu Phe Asp Glu Met Glu Glu Cys Ala Ser
    1700                1705                1710

His Leu Pro Tyr Ile Glu Gln Gly Met Gln Leu Ala Glu Gln Phe
    1715                1720                1725

Lys Gln Lys Ala Ile Gly Leu Leu Gln Thr Ala Thr Lys Gln Ala
    1730                1735                1740

Glu Ala Ala Ala Pro Val Val Glu Ser Lys Trp Arg Thr Leu Glu
    1745                1750                1755

Ala Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ser Ile Thr Ser Pro Leu Thr Thr
    1790                1795                1800

Gln His Thr Leu Leu Phe Asn Ile Leu Gly Gly Trp Val Ala Ala
    1805                1810                1815

Gln Leu Ala Pro Pro Ser Ala Ala Ser Ala Phe Val Gly Ala Gly
    1820                1825                1830

Ile Ala Gly Ala Ala Val Gly Ser Ile Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Val Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Gln Ile Leu Ser Ser Leu Thr Ile
    1940                1945                1950

Thr Gln Leu Leu Lys Arg Leu His Gln Trp Ile Asn Glu Asp Cys
    1955                1960                1965

Ser Thr Pro Cys Ser Gly Ser Trp Leu Arg Asp Val Trp Asp Trp
    1970                1975                1980

Ile Cys Thr Val Leu Thr Asp Phe Lys Thr Trp Leu Gln Ser Lys
    1985                1990                1995

Leu Leu Pro Arg Leu Pro Gly Val Pro Phe Phe Ser Cys Gln Arg
    2000                2005                2010

Gly Tyr Lys Gly Val Trp Arg Gly Asp Gly Ile Met Gln Thr Thr
    2015                2020                2025
```

```
Cys Pro Cys Gly Ala Gln Ile Thr Gly His Val Lys Asn Gly Ser
    2030                2035                2040

Met Arg Ile Val Gly Pro Arg Thr Cys Ser Asn Thr Trp His Gly
    2045                2050                2055

Thr Phe Pro Ile Asn Ala Tyr Thr Thr Gly Pro Cys Thr Pro Ser
    2060                2065                2070

Pro Ala Pro Asn Tyr Ser Arg Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Glu Glu Val Thr Phe Leu
    2135                2140                2145

Val Gly Leu Asn Gln Tyr Leu Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Thr Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Thr Arg His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Glu Pro Leu Gln Ala Glu Glu Asp Glu Arg Glu Val
    2255                2260                2265

Ser Val Pro Ala Glu Ile Leu Arg Arg Ser Arg Lys Phe Pro Arg
    2270                2275                2280

Ala Met Pro Ile Trp Ala Arg Pro Asp Tyr Asn Pro Pro Leu Leu
    2285                2290                2295

Glu Ser Trp Lys Asp Pro Asp Tyr Val Pro Pro Val Val His Gly
    2300                2305                2310

Cys Pro Leu Pro Pro Ala Lys Ala Pro Pro Ile Pro Pro Pro Arg
    2315                2320                2325

Arg Lys Arg Thr Val Val Leu Ser Glu Ser Thr Val Ser Ser Ala
    2330                2335                2340

Leu Ala Glu Leu Ala Thr Lys Thr Phe Gly Ser Ser Glu Ser Ser
    2345                2350                2355

Ala Val Asp Ser Gly Thr Ala Thr Ala Ser Pro Asp Gln Pro Ser
    2360                2365                2370

Asp Asp Gly Asp Ala Gly Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Glu Glu Ala Ser Glu Asp Val Val Cys
    2405                2410                2415
```

```
Cys Ser Met Ser Tyr Thr Trp Thr Gly Ala Leu Ile Thr Pro Cys
    2420            2425                2430

Ala Ala Glu Glu Thr Lys Leu Pro Ile Asn Ala Leu Ser Asn Ser
    2435            2440                2445

Leu Leu Arg His His Asn Leu Val Tyr Ala Thr Thr Ser Arg Ser
    2450            2455                2460

Ala Ser Leu Arg Gln Lys Lys Val Thr Phe Asp Arg Leu Gln Val
    2465            2470                2475

Leu Asp Asp His Tyr Arg Asp Val Leu Lys Glu Met Lys Ala Lys
    2480            2485                2490

Ala Ser Thr Val Lys Ala Lys Leu Leu Ser Val Glu Glu Ala Cys
    2495            2500                2505

Lys Leu Thr Pro Pro His Ser Ala Arg Ser Lys Phe Gly Tyr Gly
    2510            2515                2520

Ala Lys Asp Val Arg Asn Leu Ser Ser Lys Ala Val Asn His Ile
    2525            2530                2535

Arg Ser Val Trp Lys Asp Leu Leu Glu Asp Thr Glu Thr Pro Ile
    2540            2545                2550

Asp Thr Thr Ile Met Ala Lys Asn Glu Val Phe Cys Val Gln Pro
    2555            2560                2565

Glu Lys Gly Gly Arg Lys Pro Ala Arg Leu Ile Val Phe Pro Asp
    2570            2575                2580

Leu Gly Val Arg Val Cys Glu Lys Met Ala Leu Tyr Asp Val Val
    2585            2590                2595

Ser Thr Leu Pro Gln Ala Val Met Gly Ser Ser Tyr Gly Phe Gln
    2600            2605                2610

Tyr Ser Pro Gly Gln Arg Val Glu Phe Leu Val Asn Ala Trp Lys
    2615            2620                2625

Ala Lys Lys Cys Pro Met Gly Phe Ala Tyr Asp Thr Arg Cys Phe
    2630            2635                2640

Asp Ser Thr Val Thr Glu Asn Asp Ile Arg Val Glu Glu Ser Ile
    2645            2650                2655

Tyr Gln Cys Cys Asp Leu Ala Pro Glu Ala Arg Gln Ala Ile Arg
    2660            2665                2670

Ser Leu Thr Glu Arg Leu Tyr Ile Gly Gly Pro Leu Thr Asn Ser
    2675            2680                2685

Lys Gly Gln Asn Cys Gly Tyr Arg Arg Cys Arg Ala Ser Gly Val
    2690            2695                2700

Leu Thr Thr Ser Cys Gly Asn Thr Leu Thr Cys Tyr Leu Lys Ala
    2705            2710                2715

Ala Ala Ala Cys Arg Ala Ala Lys Leu Gln Asp Cys Thr Met Leu
    2720            2725                2730

Val Cys Gly Asp Asp Leu Val Val Ile Cys Glu Ser Ala Gly Thr
    2735            2740                2745

Gln Glu Asp Glu Ala Ser Leu Arg Ala Phe Thr Glu Ala Met Thr
    2750            2755                2760

Arg Tyr Ser Ala Pro Pro Gly Asp Pro Pro Lys Pro Glu Tyr Asp
    2765            2770                2775

Leu Glu Leu Ile Thr Ser Cys Ser Ser Asn Val Ser Val Ala His
    2780            2785                2790

Asp Ala Ser Gly Lys Arg Val Tyr Tyr Leu Thr Arg Asp Pro Thr
    2795            2800                2805
```

```
Thr Pro Leu Ala Arg Ala Ala Trp Glu Thr Ala Arg His Thr Pro
    2810            2815                2820

Val Asn Ser Trp Leu Gly Asn Ile Ile Met Tyr Ala Pro Thr Leu
    2825            2830                2835

Trp Ala Arg Met Ile Leu Met Thr His Phe Phe Ser Ile Leu Leu
    2840            2845                2850

Ala Gln Glu Gln Leu Glu Lys Ala Leu Asp Cys Gln Ile Tyr Gly
    2855            2860                2865

Ala Cys Tyr Ser Ile Glu Pro Leu Asp Leu Pro Gln Ile Ile Gln
    2870            2875                2880

Arg Leu His Gly Leu Ser Ala Phe Ser Leu His Ser Tyr Ser Pro
    2885            2890                2895

Gly Glu Ile Asn Arg Val Ala Ser Cys Leu Arg Lys Leu Gly Val
    2900            2905                2910

Pro Pro Leu Arg Val Trp Arg His Arg Ala Arg Ser Val Arg Ala
    2915            2920                2925

Arg Leu Leu Ser Gln Gly Gly Arg Ala Ala Thr Cys Gly Lys Tyr
    2930            2935                2940

Leu Phe Asn Trp Ala Val Arg Thr Lys Leu Lys Leu Thr Pro Ile
    2945            2950                2955

Pro Ala Ala Ser Gln Leu Asp Leu Ser Ser Trp Phe Val Ala Gly
    2960            2965                2970

Tyr Ser Gly Gly Asp Ile Tyr His Ser Leu Ser Arg Ala Arg Pro
    2975            2980                2985

Arg Trp Phe Met Trp Cys Leu Leu Leu Leu Ser Val Gly Val Gly
    2990            2995                3000

Ile Tyr Leu Leu Pro Asn Arg
    3005            3010
```

COMPOUNDS, COMPOSITIONS, AND METHODS FOR CONTROL OF HEPATITIS C VIRAL INFECTIONS

CROSS-REFERENCE TO RELATED APPLICATIONS

This patent application is a National Stage application of International Patent Application No PCT/US2009/062544, filed Oct. 29, 2009, which is incorporated herein by reference in its entirety and which claims the benefit of U.S. Provisional Patent Application No. 61/109,372, filed Oct. 29, 2008, which is incorporated herein by reference in its entirety.

STATEMENT REGARDING FEDERALLY SPONSORED RESEARCH OR DEVELOPMENT

Not Applicable.

INCORPORATION OF SEQUENCE LISTING

A computer readable form of the sequence listing is provided herein, containing the file named "66146_96260_SEQ_LIST.txt", which is 52278 bytes in size (measured in MS-DOS), and is herein incorporated by reference. This Sequence Listing consists of SEQ ID NOs: 1-9.

BACKGROUND OF THE INVENTION

About 2% of the world population (123 million individuals) are chronically infected with the hepatitis C virus (HCV). Chronic infection puts these individuals at risk for the development of hepatitis, cirrhosis, liver failure and hepatocellular carcinoma making chronic hepatitis C the leading cause for liver transplantation worldwide. In the United States a seroprevalence rate of 1.8% has been reported and HCV is associated with more than half of an increasing number of newly diagnosed hepatocellular carcinomas.

Current therapy combining pegylated interferon-alpha with ribavirin achieves cure rates of just above 50% (Fried et al., 2002, N Engl J Med 347:975-82; Manns et al., 2001, Lancet 358:958-965). Several difficult to treat patient groups show decreased response rates or cannot tolerate therapy at all. These include patients that have failed to respond to standard therapy, African Americans, patients with HIV-coinfection or end-stage liver disease and patients after liver transplantation. Currently, HCV infection of the graft after liver transplantation is universal, usually leading to rapid fibrosis progression and subsequent graft failure. This accounts for the poor outcome of liver transplantation for HCV-induced cirrhosis compared to other indications (Forman et al., 2002, Gastroenterology 122:889-96).

HCV is a member of the family Flaviviridae, which also includes Pestiviruses and Flaviviruses. The HCV virion consists of an enveloped nucleocapsid containing the viral genome, a single, positive stranded RNA of approximately 9,600 nucleotides. The HCV genome encodes a single long open reading frame giving rise to a viral polyprotein of over 3000 amino acids that then undergoes co- and post-translational proteolytic processing to generate the mature viral proteins: C-E1-E2-p7-NS2-NS3-NS4A-NS4B-NS5A-NS5B. The viral structural proteins, including core, the capsid protein E1, and E2, are encoded by the first third of the polyprotein p7 (a putative ion channel) and nonstructural (NS) proteins, encoded by the C-terminal two-thirds of the polyprotein, are components of the HCV RNA replication complex. The replication of the viral genome occurs through a negative strand RNA intermediate.

HCV replication and the HCV non-structural proteins involved in this process have been identified as targets for development of antiviral compounds. Identification of antiviral compounds that inhibit the HCV non-structural proteins and replication of subgenomic HCV replicons have been disclosed (see, for example, U.S. Pat. No. 7,241,796). Compounds that bind NS4B and inhibit replication of subgenomic HCV replicons have also been reported (U.S. Patent Application Publication No. 20070269420). Nonetheless, there remains an urgent need for additional compounds, compositions, and methods that can be used to treat or prevent HCV infections.

SUMMARY OF INVENTION

The present invention relates to compounds, compositions, and methods for the prevention and treatment of viral infections and diseases, especially wherein such infections and diseases are caused by the hepatitis C virus. The invention further relates to biomarkers for identification of HCV strains which are resistant to the compounds.

Certain embodiments of the invention provide compounds of the formula (I):

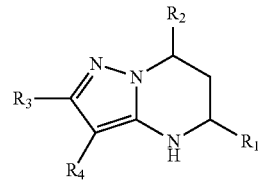

or pharmaceutically acceptable salts thereof, where:

$R_1$ is selected from the group consisting of substituted aryl, unsubstituted aryl substituted heteroaryl, unsubstituted heteroaryl, polyhaloalkyl, substituted alkyl, unsubstituted alkyl, substituted cycloalkyl, unsubstituted cycloalkyl, substituted arylalkyl, unsubstituted arylalkyl, substituted heteroarylalkyl, and unsubstituted heteroarylalkyl groups;

$R_2$ is selected from the group consisting of polyhaloalkyl, substituted aryl, unsubstituted aryl, substituted heteroaryl, unsubstituted heteroaryl, substituted arylalkyl, unsubstituted arylalkyl, substituted heteroarylalkyl, and unsubstituted heteroarylalkyl groups;

$R_3$ is selected from the group consisting of substituted aryl, unsubstituted aryl, substituted heteroaryl, unsubstituted heteroaryl, substituted alkyl, unsubstituted alkyl, cycloalkyl, substituted arylalkyl, unsubstituted arylalkyl, heteroalkyl, alkoxy, alkyl thio, aryloxy, hydrogen, amino, —COOH, —CO—NH$_2$, —CO—O—R"3, —CO—S—R"3, and —CO—NR'3-R"3 groups, wherein R'3 is a hydrogen, alkyl, substituted aryl, unsubstituted aryl, substituted heteroaryl or unsubstituted heteroaryl group, and wherein R"3 is substituted aryl, unsubstituted aryl, substituted alkyl, unsubstituted alkyl, substituted cycloalkyl, unsubstituted cycloalkyl, or —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, substituted alkyl, unsubstituted alkyl, substituted cycloalkyl, unsubstituted cycloalkyl, substituted arylalkyl, unsubstituted arylalkyl, substituted arylalkyl, or heteroalkyl group;

$R_4$ is selected from the group consisting of hydrogen, alkyl, cyano (CN), hydroxyl, nitro, chloro, bromo, fluoro, iodo, —COOH, —CO—NH₂, —CO—O—R"4, —CO—S—R"4, and —CO—NR'4-R"4 groups, wherein R'4 is a hydrogen, substituted alkyl, unsubstituted alkyl, substituted aryl, unsubstituted aryl, substituted heteroaryl or unsubstituted heteroaryl group, and wherein R"4 is —(X)—R, wherein X is a —(CH₂)ₙ— or —CO— linker group, wherein n is 1, 2, or 3, and wherein R is a substituted aryl, unsubstituted aryl, substituted heteroaryl, unsubstituted heteroaryl, adamantyl, alkyl, cycloalkyl, unsubstituted arylalkyl, substituted arylalkyl, or heteroalkyl group; and where the compounds or salts are enantiomers with R₁ and R₂ in a syn configuration that inhibits hepatitis C viral replication, the enantiomers being substantially free of other enantiomeric forms. In certain embodiments, R₁ can be selected from the group consisting of a substituted aryl, substituted furyl-2, unsubstituted furyl-2, substituted thienyl-2, and unsubstituted thienyl-2 group. In certain embodiments, R₁ is furyl-2 or substituted furyl-2. In certain embodiments, R₂ is a polyhaloalkyl selected from the group consisting of —CCl₃, —CBr₃, —CF₃, —CF₂Cl, —CF₂Br, —CF₂I, —CCl₂F, and —CBr₂F. In certain embodiments, R₂ is —CF₃. In certain embodiments, R₃ is —CO—NR'3-R"3, wherein R'3 is hydrogen and R"3 is a substituted aryl, unsubstituted aryl, substituted alkyl, unsubstituted alkyl, substituted cycloalkyl, or —(X)—R, wherein X is —(CH₂)ₙ—, wherein n is 1 or 2, and wherein R is a substituted aryl, unsubstituted aryl, substituted heteroaryl, unsubstituted heteroaryl, substituted alkyl, unsubstituted alkyl, substituted cycloalkyl, unsubstituted cycloalkyl, unsubstituted arylalkyl, substituted arylalkyl, or heteroalkyl group. In certain embodiments, R₃ is —CO—NR'3-R"3, wherein R'3 is hydrogen and R"3 is a meta-substituted phenyl or —(X)—R, wherein X is —(CH₂)ₙ—, wherein n is 1 or 2, and wherein R is a meta-substituted aryl, ortho-substituted aryl, meta/ortho substituted aryl, unsubstituted aryl, substituted heteroaryl, or unsubstituted heteroaryl group. In certain embodiments, R₃ is —CO—NR'3-R"3, wherein R'3 is hydrogen and R"3 is a meta hydroxyalkyl substituted phenyl or —(X)—R, wherein X is —(CH₂)ₙ—, wherein n is 1 or 2, and wherein R is a substituted furyl, an unsubstituted furyl, a substituted thiophene or an unsubstituted thiophene group. In certain embodiments, R₃ is —CO—NR'3-R"3, wherein R'3 is hydrogen and R"3 is phenyl-m-(CHOH)—CH₃, or —(X)—R, wherein X is —(CH₂)ₙ—, wherein n is 1 or 2, and wherein R is furyl-2, substituted furyl-2, thiophene-2-yl or substituted thiophene-2-yl. In certain embodiments, R₄ can be a halogen selected from the group consisting of fluorine, chlorine, and bromine. In certain embodiments, R₄ is chlorine. In certain embodiments, R₁ can be substituted thienyl-2, unsubstituted thienyl-2, substituted furyl-2, or unsubstituted furyl-2, R₂ is a polyhaloalkyl selected from the group consisting of —CCl₃, —CBr₃, —CF₃, —CF₂Cl, —CF₂Br, —CF₂I, —CCl₂F, and —CBr₂F, R₃ is —CO—NH—R"3 and R"3 is -phenyl-m-(CHOH)—CH₃, furane-2ylmethyl-, substituted furane-2ylmethyl-, -thiophene-2-ylmethyl, or substituted thiophene-2-ylmethyl, and R₄ is hydrogen, chlorine, or bromine. In certain embodiments, R₁ can be furyl-2, R₂ is a polyhaloalkyl selected from the group consisting of —CCl₃, —CBr₃, —CF₃, —CF₂Cl, —CF₂Br, —CF₂I, —CCl₂F, and —CBr₂F, R₃ is —CO—NH—R"3 and R"3 is -thiophene-2-ylmethyl. In certain embodiments, R₃ is —CO—NH—R"3. In certain embodiments, R₁ can be selected from the group consisting of a substituted aryl, substituted furyl-2, unsubstituted furyl-2, substituted thienyl-2, and unsubstituted thienyl-2 group, and R₃ is —CO—NH—R"3. In certain embodiments, R₁ is furyl-2 or substituted furyl-2, and R₃ is —CO—NH—R"3. In certain embodiments, R₂ can be a polyhaloalkyl selected from the group consisting of —CCl₃, —CBr₃, —CF₃, —CF₂Cl, —CF₂Br, —CF₂I, —CCl₂F, and —CBr₂F, and R₃ is —CO—NH—R"3. In certain embodiments, R₂ is —CF₃ and R₃ is —CO—NH—R"3. In certain embodiments, R₃ is —CO—NH—R"3, wherein R"3 is —(CH₂)—R, and wherein R can be a substituted aryl, unsubstituted aryl, substituted heteroaryl, unsubstituted heteroaryl, substituted cycloalkyl, or unsubstituted cycloakyl group. In certain embodiments, R₃ is —CO—NH—R"3, wherein R"3 is —(CH₂)—R, and wherein R is a substituted furyl, unsubstituted furyl, substituted thiophene or unsubstituted thiophene group. In certain embodiments, R₃ is —CO—NH—R"3, wherein R"3 is —(CH₂)—R, and wherein R furyl-2, substituted furyl-2, thiophene-2-yl or substituted thiophene-2-yl group. In certain embodiments, R₃ is —CO—NH—R"3, wherein R₄ is selected from the group consisting of hydrogen, fluorine, chlorine, and bromine. In certain embodiments, R₃ is —CO—NH—R"3, wherein R₄ is hydrogen, chlorine, or bromine. In certain embodiments, R₃ is —CO—NH—R"3, wherein R₄ is chlorine. In certain embodiments, R₁ can be thienyl-2, unsubstituted thienyl-2 furyl-2, or substituted furyl-2, R₂ is a polyhaloalkyl selected from the group consisting of —CCl₃, —CBr₃, —CF₃, —CF₂Cl, —CF₂Br, —CF₂I, —CCl₂F, and —CBr₂F, and R₃ is —CO—NH—R"3. In certain embodiments, R₁ is furyl-2 or substituted furyl-2, R₂ is a polyhaloalkyl selected from the group consisting of —CCl₃, —CBr₃, —CF₃, —CF₂Cl, —CF₂Br, —CF₂I, —CCl₂F, and —CBr₂F, R₃ is —CO—NH—R"3, and R"3 is a meta-substituted phenyl, substituted alkyl, thiophene-2-ylmethyl, or substituted thiophene-2-ylmethyl. In certain embodiments, R₁ is furyl-2 or substituted furyl-2, R₂ is a polyhaloalkyl selected from the group consisting of —CCl₃, —CBr₃, —CF₃, —CF₂Cl, —CF₂Br, —CF₂I, —CCl₂F, and —CBr₂F, R₃ is —CO—NH—R"3, R₃ is —CO—NH—R"3, where R"3 a meta-substituted phenyl wherein said meta substitution is a cyano, hydroxyl, hydroxyalkyl, nitro, chloro, bromo, fluoro, amino, carboxyl, or —CO—NH2 group, and R₄ is chlorine or bromine. In certain embodiments, R₁ is furyl-2, R₂ is —CF₃, R₃ is —CO—NH—R"3, R"3 is thiophene-2-yl-methyl, and R₄ is chlorine. In certain embodiments, R₁ is furyl-2, R₂ is —CF₃, R₃ is —CO—NH—R"3, R"3 is -thiophene-2-yl-methyl, and R₄ is bromine. In certain embodiments, R₁ is thiophene-2-yl, R₂ is —CF₃, R₃ is —CO—NH—R"3, R"3 is thiophene-2-ylmethyl, and R₄ is chlorine. In certain embodiments, R₁ is thiophene-2-yl, R₂ is —CF₃, R₃ is —CO—NH—R"3, R"3 is -thiophene-2-yl-methyl, and R₄ is bromine. In certain embodiments, R₁ is furyl-2, R₂ is —CF₃, R₃ is —CO—NH—R"3, R"3 is a meta-substituted phenyl wherein said meta substitution is a cyano, hydroxyl, hydroxyalkyl, nitro, chloro, bromo, fluoro, amino, carboxyl, or —CO—NH2 group, and R₄ is chlorine or bromine. In certain embodiments, R₁ is furyl-2, R₂ is —CF₃, R₃ is —CO—NH—R"3, R"3 is -phenyl-m-(CHOH)—CH₃, and R₄ is chlorine.

In other embodiments, the enantiomer with R₁ and R₂ in a syn configuration that inhibits hepatitis C viral replication of any of the aforementioned compounds has the structure:

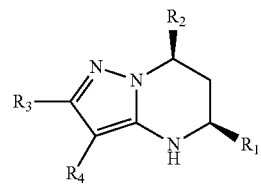

wherein the enantiomer us substantially free of other enantiomeric forms.

Certain other embodiments of the invention provide for enantiomers being substantially free of other enantiomeric forms of the formula:

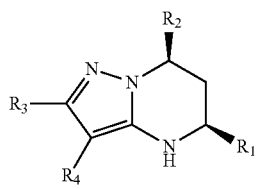

or a pharmaceutically acceptable salt thereof, wherein: $R_1$ is unsubstituted thienyl-2, substituted thienyl-2, unsubstituted furyl-2, or substituted furyl-2; $R_2$ is a polyhaloalkyl selected from the group consisting of —CCl$_3$, —CBr$_3$, —CF$_3$, —CF$_2$Cl, —CF$_2$Br, —CF$_2$I, —CCl$_2$F, and —CBr$_2$F; $R_3$ is —CO—NH$_2$ or $R_3$ is —CO—NHR'3-R"3, wherein R'3 is hydrogen and R"3 is -phenyl-m-(CHOH)—CH$_3$, furan-2-yl-methyl, substituted furan-2-yl-methyl, thiophene-2-yl-methyl, or substituted thiophene-2-yl-methyl; and $R_4$ is hydrogen, chlorine, or bromine. In certain embodiments, $R_1$ is furyl-2 or thienyl-2. In certain embodiments, $R_2$ is —CF$_3$. In certain embodiments, $R_3$ is —CO—NH$_2$. In certain embodiments, $R_3$ is —CO—NHR'3-R"3, wherein R'3 is hydrogen and R"3 is -phenyl-m-(CHOH)—CH$_3$. In certain embodiments, $R_3$ is —CO—NHR'3-R"3, wherein R'3 is hydrogen and R"3 is furan-2-yl-methyl, substituted furan-2-yl-methyl, thiophene-2-yl-methyl, or substituted thiophene-2-yl-methyl. In certain embodiments, $R_3$ is —CO—NHR'3-R"3, wherein R'3 is hydrogen and R"3 is furan-2-yl-methyl or thiophene-2-yl-methyl. In certain embodiments, $R_1$ is furyl-2 or thienyl-2, $R_2$ is —CF$_3$, and $R_3$ is —CO—NH$_2$. In certain embodiments, $R_1$ is furyl-2 or thienyl-2, $R_2$ is —CF$_3$, and $R_3$ is —CO—NHR'3-R"3, wherein R'3 is hydrogen and R"3 is -phenyl-m-(CHOH)—CH$_3$. In certain embodiments, $R_1$ is furyl-2 or thienyl-2, $R_2$ is —CF$_3$, and $R_3$ is —CO—NHR'3-R"3, wherein R'3 is hydrogen and R"3 is furan-2-yl-methyl or thiophene-2-yl-methyl. In certain embodiments, $R_1$ is furyl-2 and $R_2$ is —CF$_3$. In certain embodiments, $R_1$ is furyl-2, $R_2$ is —CF$_3$, and $R_4$ is Cl. In certain embodiments, $R_2$ is —CF$_3$ and $R_3$ is —CO—NHR'3-R"3, wherein R'3 is hydrogen and R"3 is furan-2-yl-methyl or thiophene-2-yl-methyl. In certain embodiments, the enantiomer has the structure:

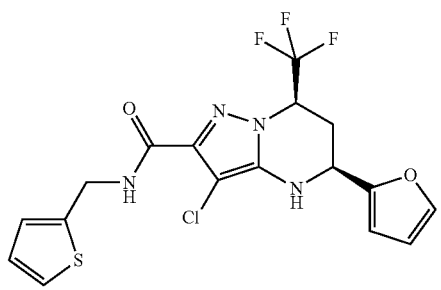 [SMILES: O=C(NCc1cccs1)c1nn2c(c1Cl)N[C@H](c1ccco1)C[C@@H]2C(F)(F)F]

or the structure:

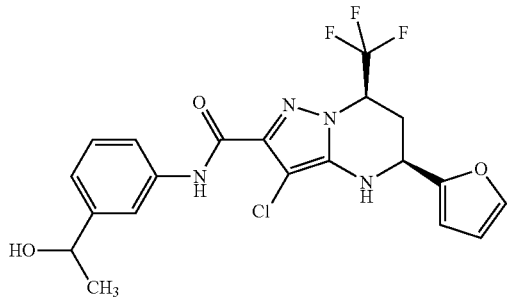 [SMILES: CC(O)c1cccc(NC(=O)c2nn3c(c2Cl)N[C@H](c2ccco2)C[C@@H]3C(F)(F)F)c1]

or the structure:

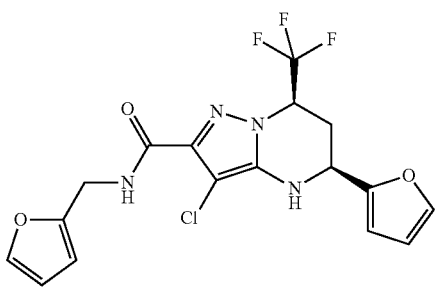 [SMILES: O=C(NCc1ccco1)c1nn2c(c1Cl)N[C@H](c1ccco1)C[C@@H]2C(F)(F)F]

or the structure:

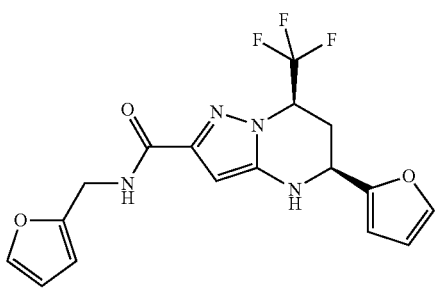 [SMILES: O=C(NCc1ccco1)c1cc2n(n1)[C@@H](C(F)(F)F)C[C@@H](c1ccco1)N2]

or the structure:

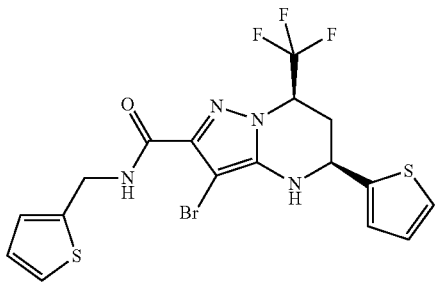 [SMILES: O=C(NCc1cccs1)c1nn2c(c1Br)N[C@H](c1cccs1)C[C@@H]2C(F)(F)F]

or the structure:

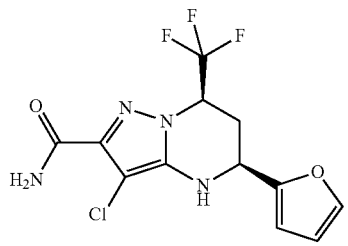 [SMILES: NC(=O)c1nn2c(c1Cl)N[C@H](c1ccco1)C[C@@H]2C(F)(F)F]

or a pharmaceutically acceptable salt thereof.

Certain other embodiments of the invention provide for pharmaceutical compositions comprising a compound of the formula (I):

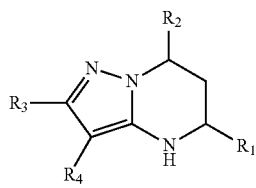

or a pharmaceutically acceptable salt thereof and one or more pharmaceutically acceptable carriers, where:

$R_1$ is selected from the group consisting of substituted aryl, unsubstituted aryl substituted heteroaryl, unsubstituted heteroaryl, polyhaloalkyl, substituted alkyl, unsubstituted alkyl, substituted cycloalkyl, unsubstituted cycloalkyl, substituted arylalkyl, unsubstituted arylalkyl, substituted heteroarylalkyl, and unsubstituted heteroarylalkyl groups;

$R_2$ is selected from the group consisting of polyhaloalkyl, substituted aryl, unsubstituted aryl, substituted heteroaryl, unsubstituted heteroaryl, substituted arylalkyl, unsubstituted arylalkyl, substituted heteroarylalkyl, and unsubstituted heteroarylalkyl groups;

$R_3$ is selected from the group consisting of substituted aryl, unsubstituted aryl, substituted heteroaryl, unsubstituted heteroaryl, substituted alkyl, unsubstituted alkyl, cycloalkyl, substituted arylalkyl, unsubstituted arylalkyl, heteroalkyl, alkoxy, alkyl thio, aryloxy, hydrogen, amino, —COOH, —CO—NH$_2$, —CO—O—R"3, —CO—S—R"3, and —CO—NR'3-R"3 groups, wherein R'3 is a hydrogen, alkyl, substituted aryl, unsubstituted aryl, substituted heteroaryl or unsubstituted heteroaryl group, and wherein R"3 is substituted aryl, unsubstituted aryl, substituted alkyl, unsubstituted alkyl, substituted cycloalkyl, unsubstituted cycloalkyl, or —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, substituted alkyl, unsubstituted alkyl, substituted cycloalkyl, unsubstituted cycloalkyl, substituted arylalkyl, substituted arylalkyl, or heteroalkyl group;

$R_4$ is selected from the group consisting of hydrogen, alkyl, cyano (CN), hydroxyl, nitro, chloro, bromo, fluoro, iodo, —COOH, —CO—NH$_2$, —CO—O—R"4, —CO—S—R"4, and —CO—NR'4-R"4 groups, wherein R'4 is a hydrogen, substituted alkyl, unsubstituted alkyl, substituted aryl, unsubstituted aryl, substituted heteroaryl or unsubstituted heteroaryl group, and wherein R"4 is —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, adamantyl, alkyl, cycloalkyl, unsubstituted arylalkyl, substituted arylalkyl, or heteroalkyl group; and where the compounds or salts thereof are enantiomers with $R_1$ and $R_2$ in a syn configuration that inhibit hepatitis C viral replication, said enantiomers being substantially free of other enantiomeric forms. In other embodiments, the pharmaceutical compositions can comprise any of the previously described compounds of formula (I), where the compounds or salts thereof are enantiomers with $R_1$ and $R_2$ in a syn configuration that inhibit hepatitis C viral replication, said enantiomers being substantially free of other enantiomeric forms. In other embodiments, the pharmaceutical compositions further comprise at least one additional biologically active agent selected from the group consisting of immunomodulators, hepatoprotectants, anti-inflammatory agents, antibiotics, anti-infective compounds, and antivirals. In certain embodiments, at least one agent of the at least one additional biologically active agent can be an antiviral agent selected from the group consisting of interferon, pegylated interferon, ribavirin, a viral protease inhibitor, a viral polymerase inhibitors, antiviral small interfering RNA compounds, an anti-sense antiviral compounds, a nucleotide analog, a nucleoside analog, and an immunoglobulin.

In other embodiments, the enantiomer with $R_1$ and $R_2$ in a syn configuration that inhibits hepatitis C viral replication of any of the aforementioned pharmaceutical compositions has the structure:

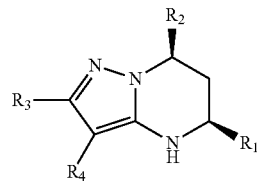

wherein the enantiomer is substantially free of other enantiomeric forms.

In certain other embodiments, the enantiomer with $R_1$ and $R_2$ in a syn configuration that inhibits hepatitis C viral replication of an aforementioned pharmaceutical compositions has the structure:

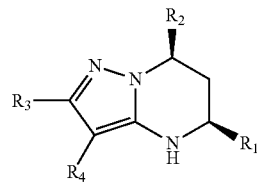

wherein the enantiomer is substantially free of other enantiomeric forms and wherein: $R_1$ is unsubstituted thienyl-2, substituted thienyl-2, unsubstituted furyl-2, or substituted furyl-2; $R_2$ is a polyhaloalkyl selected from the group consisting of —CCl$_3$, —CBr$_3$, —CF$_3$, —CF$_2$Cl, —CF$_2$Br, —CF$_2$I, —CCl$_2$F, and —CBr$_2$F; $R_3$ is —CO—NH$_2$ or $R_3$ is —CO—NHR'3-R"3, wherein R'3 is hydrogen and R"3 is -phenyl-m-(CHOH)—CH$_3$, furan-2-yl-methyl, substituted furan-2-yl-methyl, thiophene-2-yl-methyl, or substituted thiophene-2-yl-methyl; and $R_4$ is hydrogen, chlorine, or bromine. In certain embodiments, $R_1$ is furyl-2 or thienyl-2. In certain embodiments, $R_2$ is —CF$_3$. In certain embodiments, $R_3$ is —CO—NH$_2$. In certain embodiments, R$_3$ is —CO—NHR'3-R"3, wherein R'3 is hydrogen and R"3 is —phenyl-m-(CHOH)—CH$_3$. In certain embodiments, R$_3$ is —CO—NHR'3-R"3, wherein R'3 is hydrogen and R"3 is furan-2-yl-methyl, substituted furan-2-yl-methyl, thiophene-2-yl-methyl, or substituted thiophene-2-yl-methyl. In certain embodiments, R$_3$ is —CO—NHR'3-R"3, wherein R'3 is hydrogen and R"3 is furan-2-yl-methyl or thiophene-2-yl-methyl. In certain embodiments, R$_1$ is furyl-2 or thienyl-2, R$_2$ is —CF$_3$, and R$_3$ is —CO—NH$_2$. In certain embodiments, R$_1$ is furyl-2 or thienyl-2, R$_2$ is —CF$_3$, and R$_3$ is —CO—NHR'3-R"3, wherein R'3 is hydrogen and R"3 is -phenyl-m-(CHOH)—CH$_3$. In certain embodiments, R$_1$ is furyl-2 or thienyl-2, R$_2$ is —CF$_3$, and R$_3$ is —CO—NHR'3-R"3, wherein R'3 is hydrogen and R"3 is furan-2-yl-methyl or thiophene-2-yl-methyl. In certain embodiments, R$_1$ is furyl-2 and R$_2$ is —CF$_3$. In certain embodiments, R$_1$ is furyl-2, R$_2$ is —CF$_3$, and R$_4$ is Cl. In certain embodiments, R$_2$ is —CF$_3$ and R$_3$ is —CO—NHR'3-R"3, wherein R'3 is hydrogen and R"3 is furan-2-yl-methyl or thiophene-2-yl-methyl. In certain embodiments, said enantiomer has the structure:

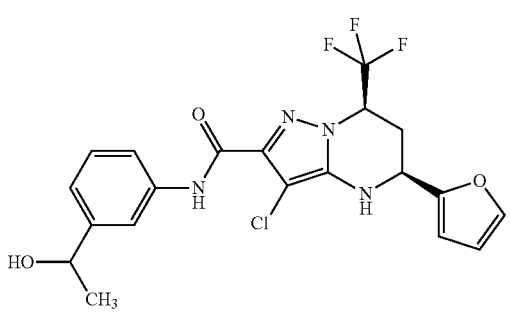 [SMILES: CC(O)c1cccc(NC(=O)c2nn3c(c2Cl)N[C@H](c2ccco2)C[C@@H]3C(F)(F)F)c1]

or the structure:

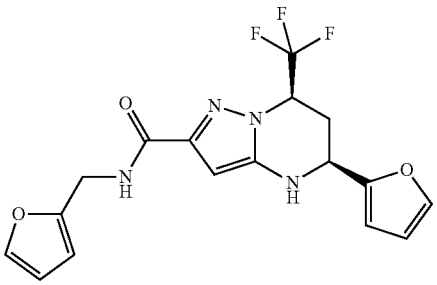 [SMILES: O=C(NCc1ccco1)c1cc2n(n1)[C@@H](C(F)(F)F)C[C@@H](c1ccco1)N2]

or the structure:

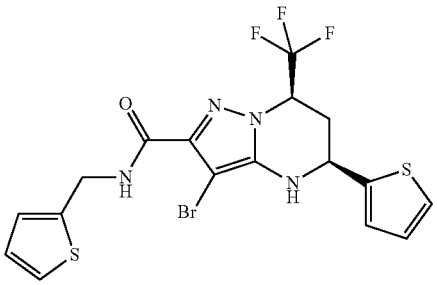

or the structure:

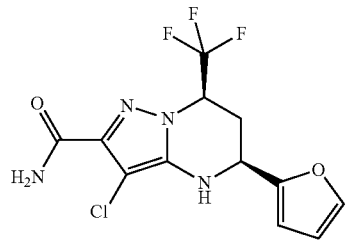 [SMILES: NC(=O)c1nn2c(c1Cl)N[C@H](c1ccco1)C[C@@H]2C(F)(F)F]

or a pharmaceutically acceptable salt thereof.

In other embodiments, the pharmaceutical compositions further comprise at least one additional biologically active agent selected from the group consisting of immunomodulators, hepatoprotectants, anti-inflammatory agents, antibiotics, anti-infective compounds, and antivirals. In certain embodiments, at least one agent of the at least one additional biologically active agent can be an antiviral agent selected from the group consisting of interferon, pegylated interferon, ribavirin, a viral protease inhibitor, a viral polymerase inhibitors, antiviral small interfering RNA compounds, an antisense antiviral compounds, a nucleotide analog, a nucleoside analog, and an immunoglobulin.

Certain other embodiments of the invention provide for methods of producing a pharmaceutical composition, the methods comprising the step of combining (a) a compound of the formula (I):

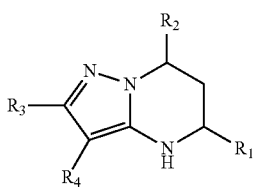

or a pharmaceutically acceptable salt thereof with (b) one or more pharmaceutically acceptable carriers, where:

$R_1$ is selected from the group consisting of substituted aryl, unsubstituted aryl substituted heteroaryl, unsubstituted heteroaryl, polyhaloalkyl, substituted alkyl, unsubstituted alkyl, substituted cycloalkyl, unsubstituted cycloalkyl, substituted arylalkyl, unsubstituted arylalkyl, substituted heteroarylalkyl, and unsubstituted heteroarylalkyl groups;

$R_2$ is selected from the group consisting of polyhaloalkyl, substituted aryl, unsubstituted aryl, substituted heteroaryl, unsubstituted heteroaryl, substituted arylalkyl, unsubstituted arylalkyl, substituted heteroarylalkyl, and unsubstituted heteroarylalkyl groups;

$R_3$ is selected from the group consisting of substituted aryl, unsubstituted aryl, substituted heteroaryl, unsubstituted heteroaryl, substituted alkyl, unsubstituted alkyl, cycloalkyl, substituted arylalkyl, unsubstituted arylalkyl, heteroalkyl, alkoxy, alkyl thio, aryloxy, hydrogen, amino, —COOH, —CO—NH$_2$, —CO—O—R"3, —CO—S—R"3, and —CO—NR'3-R"3 groups, wherein R'3 is a hydrogen, alkyl, substituted aryl, unsubstituted aryl, substituted heteroaryl or unsubstituted heteroaryl group, and wherein R"3 is substituted aryl, unsubstituted aryl, substituted alkyl, unsubstituted alkyl, substituted cycloalkyl, unsubstituted cycloalkyl, or —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, substituted alkyl, unsubstituted alkyl, substituted cycloalkyl, unsubstituted cycloalkyl, unsubstituted arylalkyl, substituted arylalkyl, or heteroalkyl group;

$R_4$ is selected from the group consisting of hydrogen, alkyl, cyano (CN), hydroxyl, nitro, chloro, bromo, fluoro, iodo, —COOH, —CO—NH$_2$, —CO—O—R"4, —CO—S—R"4, and —CO—NR'4-R"4 groups, wherein R'4 is a hydrogen, substituted alkyl, unsubstituted alkyl, substituted aryl, unsubstituted aryl, substituted heteroaryl or unsubstituted heteroaryl group, and wherein R"4 is —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, adamantyl, alkyl, cycloalkyl, unsubstituted arylalkyl, substituted arylalkyl, or heteroalkyl group, and where the compound or salt thereof is an enantiomer with $R_1$ and $R_2$ in a syn configuration that inhibits hepatitis C viral replication, said enantiomer being substantially free of other enantiomeric forms. In other embodiments, methods of making pharmaceutical compositions that can comprise any of the previously described compounds of formula (I) are provided, where the compounds or salts thereof are enantiomers with $R_1$ and $R_2$ in a syn configuration that inhibit hepatitis C viral replication, the enantiomers being substantially free of other enantiomeric forms.

In other embodiments, the enantiomer with $R_1$ and $R_2$ in a syn configuration that inhibits hepatitis C viral replication of any of the aforementioned methods of producing a pharmaceutical composition has the structure:

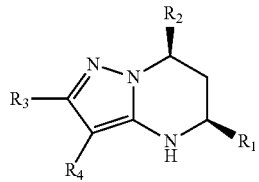

wherein the enantiomer is substantially free of other enantiomeric forms.

In certain other embodiments, the enantiomer with $R_1$ and $R_2$ in a syn configuration that inhibits hepatitis C viral replication of an aforementioned method of producing pharmaceutical compositions has the structure:

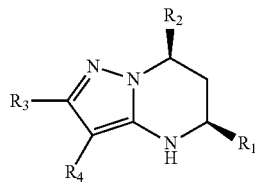

wherein the enantiomer is substantially free of other enantiomeric forms and wherein: $R_1$ is unsubstituted thienyl-2, substituted thienyl-2, unsubstituted furyl-2, or substituted furyl-2; $R_2$ is a polyhaloalkyl selected from the group consisting of —CCl$_3$, —CBr$_3$, —CF$_3$, —CF$_2$Cl, —CF$_2$Br, —CF$_2$I, —CCl$_2$F, and —CBr$_2$F; $R_3$ is —CO—NH$_2$ or $R_3$ is —CO—NHR'3-R"3, wherein R'3 is hydrogen and R"3 is -phenyl-m-(CHOH)—CH$_3$, furan-2-yl-methyl, substituted furan-2-yl-methyl, thiophene-2-yl-methyl, or substituted thiophene-2-yl-methyl; and $R_4$ is hydrogen, chlorine, or bromine. In certain embodiments, $R_1$ is furyl-2 or thienyl-2. In certain embodiments, $R_2$ is —CF$_3$. In certain embodiments, $R_3$ is —CO—NH$_2$. In certain embodiments, $R_3$ is —CO—NHR'3-R"3, wherein R'3 is hydrogen and R"3 is —phenyl-m-(CHOH)—CH$_3$. In certain embodiments, $R_3$ is —CO—NHR'3-R"3, wherein R'3 is hydrogen and R"3 is furan-2-yl-methyl, substituted furan-2-yl-methyl, thiophene-2-yl-methyl, or substituted thiophene-2-yl-methyl. In certain embodiments, $R_3$ is —CO—NHR'3-R"3, wherein R'3 is hydrogen and R"3 is furan-2-yl-methyl or thiophene-2-yl-methyl. In certain embodiments, $R_1$ is furyl-2 or thienyl-2, $R_2$ is —CF$_3$, and $R_3$ is —CO—NH$_2$. In certain embodiments, $R_1$ is furyl-2 or thienyl-2, $R_2$ is —CF$_3$, and $R_3$ is —CO—NHR'3-R"3, wherein R'3 is hydrogen and R"3 is -phenyl-m-(CHOH)—CH$_3$. In certain embodiments, $R_1$ is furyl-2 or thienyl-2, $R_2$ is —CF$_3$, and $R_3$ is —CO—NHR'3-R"3, wherein R'3 is hydrogen and R"3 is furan-2-yl-methyl or thiophene-2-yl-methyl. In certain embodiments, $R_1$ is furyl-2 and $R_2$ is —CF$_3$. In certain embodiments, $R_1$ is furyl-2, $R_2$ is —CF$_3$, and $R_4$ is Cl. In certain embodiments, $R_2$ is —CF$_3$ and $R_3$ is —CO—NHR'3-R"3, wherein R'3 is hydrogen and R"3 is furan-2-yl-methyl or thiophene-2-yl-methyl. In certain embodiments, said enantiomer has the structure:

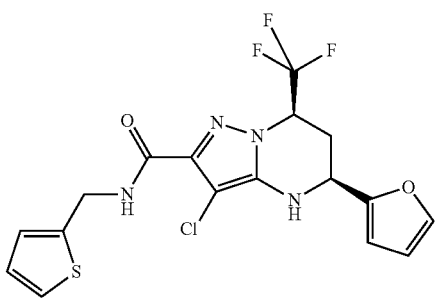 [SMILES: O=C(NCc1cccs1)c1nn2c(c1Cl)N[C@H](c1ccco1)C[C@@H]2C(F)(F)F]

or the structure:

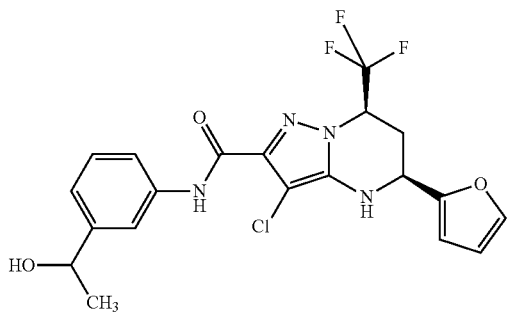 [SMILES: CC(O)c1cccc(NC(=O)c2nn3c(c2Cl)N[C@H](c2ccco2)C[C@@H]3C(F)(F)F)c1]

or the structure:

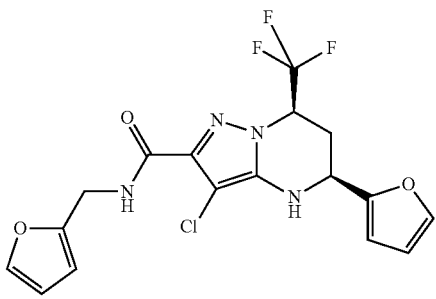 [SMILES: O=C(NCc1ccco1)c1nn2c(c1Cl)N[C@H](c1ccco1)C[C@@H]2C(F)(F)F]

or the structure:

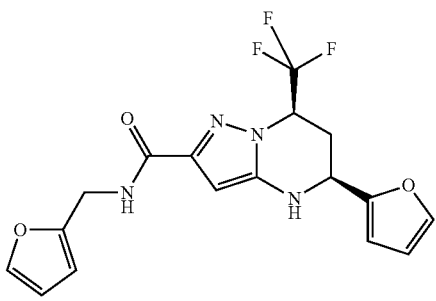 [SMILES: O=C(NCc1ccco1)c1cc2n(n1)[C@@H](C(F)(F)F)C[C@@H](c1ccco1)N2]

or the structure:

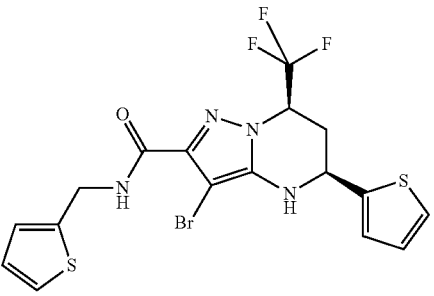 [SMILES: O=C(NCc1cccs1)c1nn2c(c1Br)N[C@H](c1cccs1)C[C@@H]2C(F)(F)F]

or the structure:

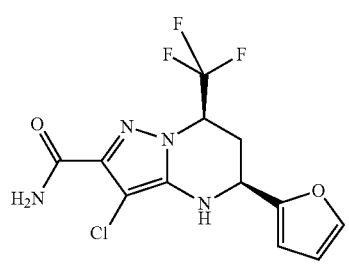 [SMILES: NC(=O)c1nn2c(c1Cl)N[C@H](c1ccco1)C[C@@H]2C(F)(F)F]

or a pharmaceutically acceptable salt thereof.

Certain other embodiments of the invention provide for methods of treating or preventing a hepatitis C viral infection in a subject in need thereof, the methods comprising administering to said subject a therapeutically effective amount of an enantiomer that inhibits hepatitis C viral replication having the formula (I):

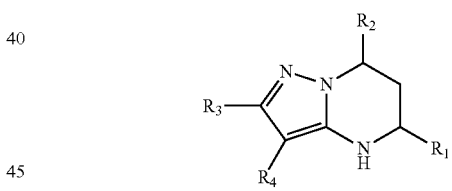

or a pharmaceutically acceptable salt thereof, where:

$R_1$ is selected from the group consisting of substituted aryl, unsubstituted aryl substituted heteroaryl, unsubstituted heteroaryl, polyhaloalkyl, substituted alkyl, unsubstituted alkyl, substituted cycloalkyl, unsubstituted cycloalkyl, substituted arylalkyl, unsubstituted arylalkyl, substituted heteroarylalkyl, and unsubstituted heteroarylalkyl groups;

$R_2$ is selected from the group consisting of polyhaloalkyl, substituted aryl, unsubstituted aryl, substituted heteroaryl, unsubstituted heteroaryl, substituted arylalkyl, unsubstituted arylalkyl, substituted heteroarylalkyl, and unsubstituted heteroarylalkyl groups;

$R_3$ is selected from the group consisting of substituted aryl, unsubstituted aryl, substituted heteroaryl, unsubstituted heteroaryl, substituted alkyl, unsubstituted alkyl, cycloalkyl, substituted arylalkyl, unsubstituted arylalkyl, heteroalkyl, alkoxy, alkyl thio, aryloxy, hydrogen, amino, —COOH, —CO—NH$_2$, —CO—O—R"3, —CO—S—R"3, and —CO—NR'3-R"3 groups, wherein R'3 is a hydrogen, alkyl, substituted aryl, unsubstituted aryl, substituted heteroaryl or unsubstituted heteroaryl group, and wherein R"3 is substituted aryl, unsubstituted aryl, substituted alkyl, unsubstituted alkyl, substituted cycloalkyl, unsubstituted cycloalkyl, or —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, substituted alkyl, unsubstituted alkyl, substituted cycloalkyl, unsubstituted cycloalkyl, substituted arylalkyl, substituted arylalkyl, or heteroalkyl group;

R$_4$ is selected from the group consisting of hydrogen, alkyl, cyano (CN), hydroxyl, nitro, chloro, bromo, fluoro, iodo, —COOH, —CO—NH$_2$, —CO—O—R"4, —CO—S—R"4, and —CO—NR'4-R"4 groups, wherein R'4 is a hydrogen, substituted alkyl, unsubstituted alkyl, substituted aryl, unsubstituted aryl, substituted heteroaryl or unsubstituted heteroaryl group, and wherein R"4 is —(X)—R, wherein X is a —(CH$_2$)$_n$— or —CO— linker group, wherein n is 1, 2, or 3, and wherein R is a substituted aryl, unsubstituted aryl, substituted heteroaryl, unsubstituted heteroaryl, adamantyl, alkyl, cycloalkyl, unsubstituted arylalkyl, substituted arylalkyl, or heteroalkyl group; and where the compound or salt thereof is an enantiomer with R$_1$ and R$_2$ in a syn configuration that inhibits hepatitis C viral replication. In certain embodiments, methods of treating or preventing a hepatitis C viral infection in a subject in need thereof are provided, the methods comprising administering to said subject a therapeutically effective amount of an enantiomer that inhibits hepatitis C viral replication, where the enantiomer is any of the previously described compounds of formula (I). In certain embodiments, the subject can be a human. In certain embodiments, the pharmaceutical composition can be administered to the subject orally, topically, rectally, percutaneously, by parenteral injection, intranasally, or by inhalation. In certain embodiments, the pharmaceutical composition can be administered in combination, either concurrently or sequentially, with at least one additional biologically active agent. In certain embodiments, the pharmaceutical composition can be administered in combination, either concurrently or sequentially, with at least one additional biologically active agent, wherein said at least one additional biologically active agent can be selected from the group consisting of immunomodulators, hepatoprotectants, anti-inflammatory agents, antibiotics, anti-infective compounds, and antivirals. In certain embodiments, the pharmaceutical composition can be administered in combination, either concurrently or sequentially, with at least one additional biologically active agent, wherein the at least one agent of said at least one additional biologically active agent can be an antiviral agent selected from the group consisting of interferon, pegylated interferon, ribavirin, viral protease inhibitors, viral polymerase inhibitors, antiviral small interfering RNA compounds, anti-sense antiviral compounds, nucleotide analogs, nucleoside analogs, and immunoglobulins. In certain embodiments, the therapeutically effective amount of the enantiomer that inhibits hepatitis C viral replication is in a mixture with at least one enantiomer or diastereoisomer that does not inhibit hepatitis C viral replication. In certain embodiments, the mixture is a racemic mixture or a non-racemic mixture. In certain embodiments, the mixture is a diastereomeric mixture. In other embodiments, the therapeutically effective amount of the enantiomer that inhibits hepatitis C viral replication is substantially free of other enantiomeric forms. In certain embodiments, the hepatitis C viral infection is an HCV genotype 1 viral infection. In certain embodiments, the HCV genotype 1 viral infection can be an HCV genotype 1a infection, an HCV genotype 1b infection, or a combination thereof.

In other embodiments, the enantiomer with R$_1$ and R$_2$ in a syn configuration that inhibits hepatitis C viral replication of any of the aforementioned methods of treating or preventing a hepatitis C viral infection has the structure:

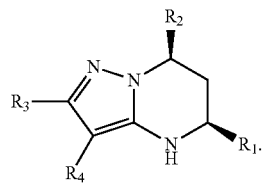

In certain other embodiments, the enantiomer with R$_1$ and R$_2$ in a syn configuration that inhibits hepatitis C viral replication of an aforementioned method of treating or preventing a hepatitis C viral infection has the structure:

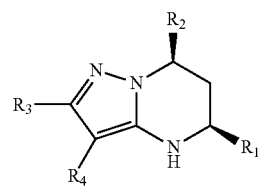

wherein: R$_1$ is unsubstituted thienyl-2, substituted thienyl-2, unsubstituted furyl-2, or substituted furyl-2; R$_2$ is a polyhaloalkyl selected from the group consisting of —CCl$_3$, —CBr$_3$, —CF$_3$, —CF$_2$Cl, —CF$_2$Br, —CF$_2$I, —CCl$_2$F, and —CBr$_2$F; R$_3$ is —CO—NH$_2$ or R$_3$ is —CO—NHR'3-R"3, wherein R'3 is hydrogen and R"3 is -phenyl-m-(CHOH)—CH$_3$, furan-2-yl-methyl, substituted furan-2-yl-methyl, thiophene-2-yl-methyl, or substituted thiophene-2-yl-methyl; and R$_4$ is hydrogen, chlorine, or bromine. In certain embodiments, R$_1$ is furyl-2 or thienyl-2. In certain embodiments, R$_2$ is —CF$_3$. In certain embodiments, R$_3$ is In certain embodiments, R$_3$ is —CO—NHR'3-R"3, wherein R'3 is hydrogen and R"3 is -phenyl-m-(CHOH)—CH$_3$. In certain embodiments, R$_3$ is —CO—NHR'3-R"3, wherein R'3 is hydrogen and R"3 is furan-2-yl-methyl, substituted furan-2-yl-methyl, thiophene-2-yl-methyl, or substituted thiophene-2-yl-methyl. In certain embodiments, R$_3$ is —CO—NHR'3-R"3, wherein R'3 is hydrogen and R"3 is furan-2-yl-methyl or thiophene-2-yl-methyl. In certain embodiments, R$_1$ is furyl-2 or thienyl-2, R$_2$ is —CF$_3$, and R$_3$ is —CO—NH$_2$. In certain embodiments, R$_1$ is furyl-2 or thienyl-2, R$_2$ is —CF$_3$, and R$_3$ is —CO—NHR'3-R"3, wherein R'3 is hydrogen and R"3 is -phenyl-m-(CHOH)—CH$_3$. In certain embodiments, R$_1$ is furyl-2 or thienyl-2, R$_2$ is —CF$_3$, and R$_3$ is —CO—NHR'3-R"3, wherein R'3 is hydrogen and R"3 is furan-2-yl-methyl or thiophene-2-yl-methyl. In certain embodiments, R$_1$ is furyl-2 and R$_2$ is —CF$_3$. In certain embodiments, R$_1$ is furyl-2, R$_2$ is —CF$_3$, and R$_4$ is Cl. In certain embodiments, R$_2$ is —CF$_3$ and R$_3$ is —CO—NHR'3-R"3, wherein R'3 is hydrogen and R"3 is furan-2-yl-methyl or thiophene-2-yl-methyl. In certain embodiments, said enantiomer has the structure:

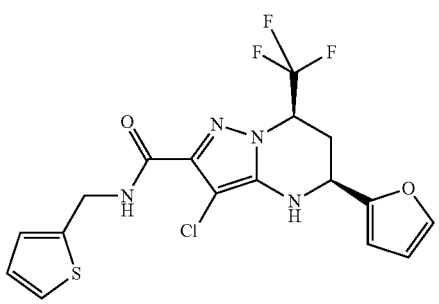 [SMILES: O=C(NCc1cccs1)c1nn2c(c1Cl)N[C@H](c1ccco1)C[C@@H]2C(F)(F)F]

or the structure:

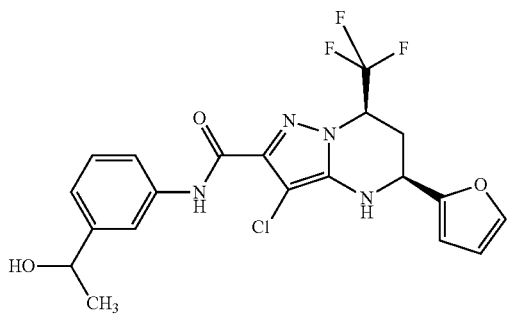 [SMILES: CC(O)c1cccc(NC(=O)c2nn3c(c2Cl)N[C@H](c2ccco2)C[C@@H]3C(F)(F)F)c1]

or the structure:

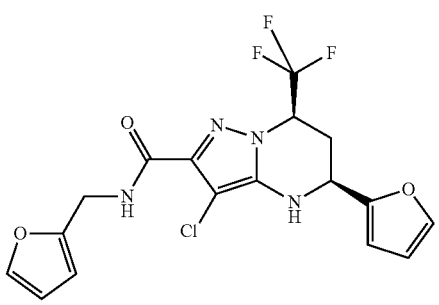 [SMILES: O=C(NCc1ccco1)c1nn2c(c1Cl)N[C@H](c1ccco1)C[C@@H]2C(F)(F)F]

or the structure:

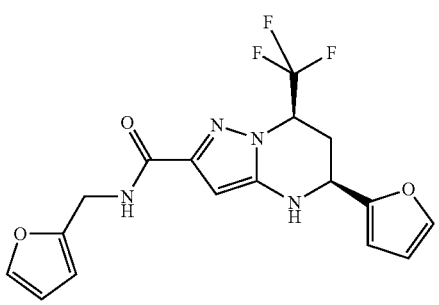 [SMILES: O=C(NCc1ccco1)c1cc2n(n1)[C@@H](C(F)(F)F)C[C@@H](c1ccco1)N2]

or the structure:

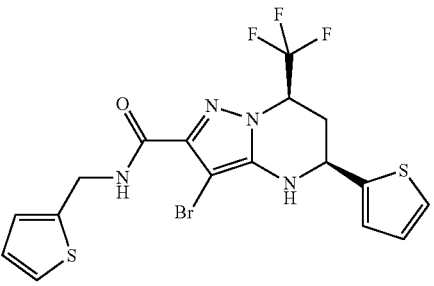

or the structure:

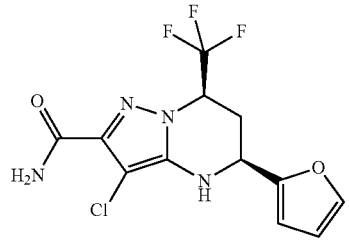 [SMILES: NC(=O)c1nn2c(c1Cl)N[C@H](c1ccco1)C[C@@H]2C(F)(F)F]

or a pharmaceutically acceptable salt thereof.

In certain embodiments, the subject can be a human. In certain embodiments, the pharmaceutical composition can be administered to the subject orally, topically, rectally, percutaneously, by parenteral injection, intranasally, or by inhalation. In certain embodiments, the pharmaceutical composition can be administered in combination, either concurrently or sequentially, with at least one additional biologically active agent. In certain embodiments, the pharmaceutical composition can be administered in combination, either concurrently or sequentially, with at least one additional biologically active agent, wherein said at least one additional biologically active agent can be selected from the group consisting of immunomodulators, hepatoprotectants, anti-inflammatory agents, antibiotics, anti-infective compounds, and antivirals. In certain embodiments, the pharmaceutical composition can be administered in combination, either concurrently or sequentially, with at least one additional biologically active agent, wherein the at least one agent of said at least one additional biologically active agent can be an antiviral agent selected from the group consisting of interferon, pegylated interferon, ribavirin, viral protease inhibitors, viral polymerase inhibitors, antiviral small interfering RNA compounds, anti-sense antiviral compounds, nucleotide analogs, nucleoside analogs, and immunoglobulins. In certain embodiments, the therapeutically effective amount of the enantiomer that inhibits hepatitis C viral replication is in a mixture with at least one enantiomer or diastereoisomer that does not inhibit hepatitis C viral replication. In certain embodiments, the mixture is a racemic mixture or a non-racemic mixture. In certain embodiments, the mixture is a diastereomeric mixture. In other embodiments, the therapeutically effective amount of the enantiomer that inhibits hepatitis C viral replication is substantially free of other enantiomeric forms. In certain embodiments, the hepatitis C viral infection is an HCV genotype 1 viral infection. In certain embodiments, the HCV genotype 1 viral infection can be an HCV genotype 1a infection, an HCV genotype 1b infection, or a combination thereof.

Certain other embodiments of the invention provide for an isolated nucleic acid comprising at least 15 nucleotides that encodes a mutant hepatitis C virus NS4B peptide sequence that comprises an amino acid residue other than phenylalanine at a position corresponding to amino acid residue 1809 of an HCV polyprotein reference sequence of SEQ ID NO:9. In other embodiments, the nucleic acid molecule comprises at least 16 or 17 nucleotides that encode said mutation. In other embodiments, the nucleic acid molecule comprises at least 18 nucleotides that encode said mutation. In other embodiments, the mutant hepatitis C virus NS4B peptide sequence comprises a leucine or a valine at a position corresponding to amino acid residue 1809 of an HCV polyprotein reference sequence of SEQ ID NO:9. In certain embodiments, the mutant hepatitis C virus NS4B peptide sequence comprises a leucine or a valine at a position corresponding to amino acid residue 1809 of an HCV polyprotein reference sequence of SEQ ID NO:9, wherein the hepatitis C virus NS4B peptide sequence comprises the sequence of SEQ ID NO:4 or SEQ ID NO:6.

Certain other embodiments of the invention provide for methods for detecting a hepatitis C virus (HCV) that is resistant to a 4,5,6,7-tetrahydropyrazolo[1,5-a]pyrimidine compound, comprising the step of determining an allelic state of a codon in said HCV that encodes an amino acid corresponding to amino acid residue 1809 of an HCV polyprotein reference sequence of SEQ ID NO:9, thereby detecting a hepatitis C virus that is resistant to a 4,5,6,7-tetrahydropyrazolo[1,5-a]pyrimidine carboxamide compound. In certain other embodiments, it can be determined that said codon encodes an amino acid other than phenylalanine. In certain embodiments, it is determined that said codon encodes valine or leucine. In other embodiments, the hepatitis C virus is a genotype 1 hepatitis C virus. In certain embodiments, the genotype 1 hepatitis C virus can be a genotype 1a or genotype 1b hepatitis C virus.

BRIEF DESCRIPTION OF THE DRAWINGS

The accompanying drawings, which are incorporated in and form a part of the specification, illustrate certain embodiments of the present invention and together with the description, serve to explain the principles of the invention. In the drawings:

FIG. 1: Exemplary Compounds of formula (I). Column 1 shows identifier numbers and column 2 shows the corresponding compound structures.

FIG. 2: Inhibition of HCV RNA Replication by Exemplary Compounds of formula (I). Column 1 shows identifier numbers and column 2 shows the corresponding compound structures. The EC50 value is the concentration (micromolar) of the indicated compound that provides for a 50% reduction in HCV replicon levels is observed relative to an untreated control.

FIG. 3 illustrates the (5S,7R) stereo configuration of the active enantiomer AP0080978. (5S,7R)-3-chloro-5-(furan-2-yl)-N-(thiophene-2-ylmethyl)-7-(trifluoromethyl)-4,5,6,7-tetrahydropyrazolo[1,5-a]pyrimidine-2-carboxamide.

FIG. 4 illustrates the features of the two viral constructs that were utilized to characterize inhibition of HCV viral infectivity.

FIG. 5: AP 80978 Inhibits Virus encoding a Sensitive NS4B protein. FIG. 5 shows that the compound AP 80978 was able to inhibit the APV112 HCV construct with a sensitive NS4B region and provides a comparison with control HCV inhibitors.

FIG. 6: AP 80978 is Inactive Against Virus encoding a Resistant NS4B protein. FIG. 6 shows that infectivity of the APV23 HCV construct was found to be resistant to AP 80978.

DETAILED DESCRIPTION OF THE INVENTION

Figure 3:
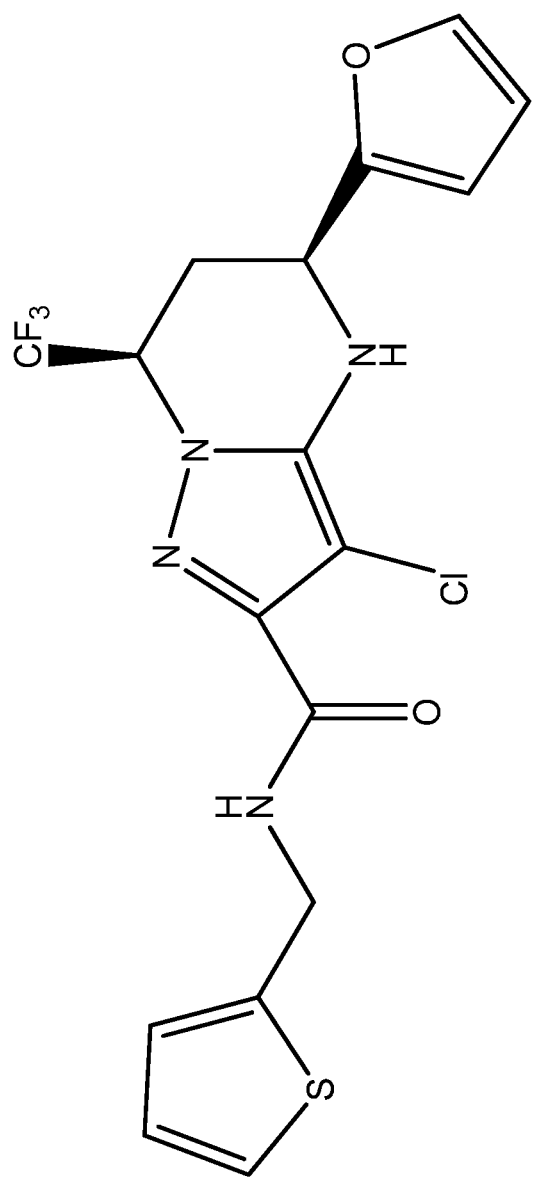
FIG. 3: Active Enantiomer.

The compounds of formula (I) and their pharmaceutically acceptable salts are shown herein to inhibit HCV viral replication. When administered to a subject in need thereof, compounds of formula (I) and their pharmaceutically acceptable salts are thus useful in the treatment and prevention of infections and diseases associated with HCV.

Definitions

Unless otherwise defined, all technical and scientific terms used herein have the same meaning as commonly understood by one of ordinary skill in the art to which this invention pertains. In the case of inconsistencies between the present disclosure and the issued patents, applications, and references that are cited herein, the present disclosure will prevail. The nomenclature used to describe organic radicals, e.g., hydrocarbons and substituted hydrocarbons, generally follows standard nomenclature known in the art, unless otherwise specifically defined.

As used herein, the terms "hepatitis C virus" and "HCV", refer to any major HCV genotype, subtype, isolate, and/or quasispecie unless otherwise indicated. HCV genotypes include, but are not limited to, genotypes 1, 2, 3, 4, 5, and 6 and HCV subtypes include, but are not limited to, subtypes 1a, 1b, 2a, 2b, 3a, 4a-4f, 5a, and 6a.

As used herein, the term "salt(s)", denotes acidic salts formed with inorganic and/or organic acids, as well as basic salts formed with inorganic and/or organic bases. In addition, when a compound of the invention contains both a basic moiety, such as, but not limited to, a pyridine or imidazole, and an acidic moiety, such as, but not limited to, a carboxylic acid, zwitterions ("inner salts") may be formed and are included within the term "salt(s)" as used herein.

As used herein the term "pharmaceutically acceptable salt", is intended to include nontoxic, physiologically acceptable salts synthesized from a compound which contains a basic or acidic moiety.

As used herein the term "prodrug", denotes a compound that is a drug precursor which, upon administration to a subject, undergoes chemical conversion by metabolic or chemical processes to yield an active compound or a salt and/or solvate thereof. Prodrugs include acid derivatives well known to practitioners of the art, such as, for example, esters prepared by reaction of the parent acidic compound with a suitable alcohol, or amides prepared by reaction of the parent acid compound with a suitable amine.

As used herein, the term "solvate", means a physical association of a compound with one or more solvent molecules, whether organic or inorganic. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolated solvates. Non-limiting examples of suitable solvates include hydrates, ethanolates, methanolates, isopropanolates and the like. "Hydrate" is a solvate wherein the solvent molecule is water ($H_2O$).

As used herein, the term "stereoisomers", refers to isomeric compounds that possess identical chemical composition, but which differ in the arrangement of their atoms or groups in space.

As used herein, the term "chiral", refers to molecules that have the property of non-superimposability of the mirror image partner, while the term "achiral" refers to molecules which are superimposable on their mirror image partner.

A used herein, the term "enantiomers", refers to two stereoisomers of a compound that are non-superimposable mirror images of one another.

As used herein, the term "diastereomers" or "diastereoisomer", refers to stereoisomers that are not enantiomers. A stereoisomeric pair with two or more centers of chirality and whose molecules are not mirror images of one another are thus diastereoisomers. Mixtures of diastereomers may be separated under high resolution analytical procedures such as electrophoresis and chromatography.

As used herein, the terms "racemic mixture" and "racemate", refer to an equimolar mixture of two enantiomeric species.

As used herein, the term "non-racemic mixture", means a mixture containing unequal parts of individual enantiomers or stereoisomers.

As used herein the phrase "diastereomeric mixture", refers to a composition comprising more than one diastereomer.

As used herein, the phrase "enantiomer being substantially free of other enantiomeric forms", is used to refer to either a compound or a composition wherein a desired enantiomer is at least 90 percent by weight of the compound or at least 90% by weight of the total amount of the compound present in a composition.

As used herein, the term "derivative", when used in reference to a chemically modified compound, refers to routine modifications of a compound. Routine modifications of compounds include, but are not limited to, formation of esters or an amides of carboxylic acids, or substitution of protecting groups. Routinely substituted protecting groups include, but are not limited to, substitutions of a benzyl group for an alcohol or thiol, and substitutions of a tert-butoxycarbonyl group for an amine.

As used herein, the term "subject", denotes both human and non-human mammals.

As used herein, the term "patient", denotes a human subject.

As used herein, the phrase "therapeutically effective amount", refers to an amount of a compound which, when administered to a subject in need thereof, is sufficient to cause any beneficial change in any symptom or marker associated with HCV infection. By "marker associated with HCV infection" is meant any biological measure that correlates with HCV infection and/or is predictive of clinical prognosis. Biological measures include, but are not limited to, a reduction in viral load. When applied to an individual active ingredient, administered alone or in a composition, the phrase refers to that active ingredient alone. When applied in a composition comprising one or more additional active ingredients, the term refers to combined amounts of the active ingredients that result in the therapeutic effect, whether administered serially or simultaneously.

As use herein, the term "prophylactically effective amount", is used to refer to an amount sufficient to prevent or reduce the severity of HCV symptoms in a subject exposed to HCV. In some embodiments, prophylactic treatment includes administering a compound or composition according to the invention to a subject found to carry HCV, but which does not exhibit symptoms of hepatitis C disease. Prophylactic treatment also includes administering a compound or composition according to the invention to a subject which shows an improved disease state, but which still carries HCV and is at risk of recurrence of symptomatic disease.

As used herein, the term "substituted", refers to replacement of one or more hydrogen atoms on a given alkyl, cycloalkyl, aryl, heteroaryl, arylalkyl, or heteroarylalkyl group with one or more of a cyano, hydroxyl, hydroxyalkyl, nitro, chloro, bromo, fluoro, amino, carboxyl, or —CO—NH2 group.

As used herein, the terms "treating" or "treatment", refers to (i) inhibiting the disease, disorder or condition, i.e., arresting or slowing its development; and (ii) relieving the disease, disorder or condition, i.e., causing regression of the disease, disorder and/or condition.

As used herein, the terms "preventing" or "prevent", refers to preventing a disease, disorder or condition from occurring in a patient which may be predisposed to the disease, disorder and/or condition but has not yet been diagnosed as having it.

As used herein, the phrase "inhibits hepatitis C viral replication", when used in reference to an enantiomeric form of a compound, refers to an enantiomeric form of the compound with an $EC_{50}$ (Effective Concentration of 50%) for reduction of HCV genotype 1a or genotype 1b subgenomic replicon content that is at least five fold less than the $EC_{50}$ for the distinct enantiomeric form of the compound.

As used herein, the phrase "pharmaceutically acceptable", refers to those compounds, materials, compositions, and/or dosage forms which are, within the scope of sound medical judgment, suitable for use in contact with the tissues of subjects without excessive toxicity, irritation, allergic response, or other problem or complication commensurate with a reasonable risk/benefit ratio.

As used herein, the term "corresponding", when used in the context of comparing, aligning, or identifying equivalent amino acids in one polypeptide sequence with another polypeptide sequence, refers to the comparison or alignment that will yield the highest percent identity when aligned with the other polypeptide sequence. When the term "corresponding" is used herein in the context of comparing, aligning, or identifying equivalent nucleotides or codons in one nucleotide sequence with another nucleotide sequence, this term refers to the comparison or alignment that will yield the highest percent identity when aligned with the other nucleotide sequence.

Compounds, Compositions and Methods for Inhibiting HCV Replication

It is demonstrated herein that compounds of the formula (I) are capable of inhibiting HCV replication. Methods for using these compounds to prevent or treat HCV infection of subjects are thus provided herein.

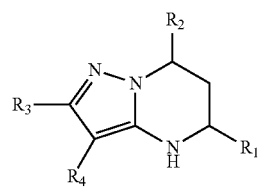

(I)

It is also demonstrated herein that inhibition of HCV replication is associated with only certain enantiomeric forms of certain compounds of formula (I) wherein $R_1$ and $R_2$ are in only one of two potential syn configurations. In certain synthetic schemes for production of certain compounds of formula (I), a mixture of both of the two syn configurations of compounds of formula (I) are produced as shown below:

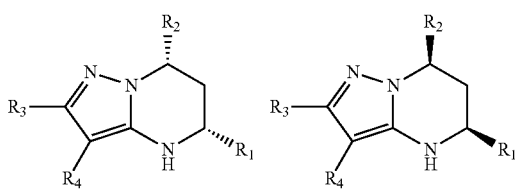

Methods of obtaining the enantiomeric form in the syn configuration of $R_1$ and $R_2$ that inhibits HCV replication and that is substantially free of the other enantiomeric form in the syn configuration of $R_1$ and $R_2$ that does not inhibit HCV replication are also provided.

Certain embodiments of the invention are thus drawn to compounds, compositions, and methods of use wherein the enantiomeric form of the compound of formula (I) that inhibits HCV replication is substantially free of other enantiomeric forms of the compound of formula (I) that do not inhibit HCV replication. Certain embodiments of the invention are also drawn to compounds, compositions, and methods of use wherein the enantiomeric form of the compound of formula (I) that inhibits HCV replication is substantially free of other enantiomeric forms of the compound of formula (I) that do not inhibit HCV replication and wherein $R_1$ and $R_2$ are in the syn configuration that represents the enantiomeric form of the compound of formula (I) that inhibits HCV replication. Thus, certain embodiments of the invention are drawn to compounds, compositions, and methods of use wherein the enantiomeric form of the compound that inhibits HCV replication is at least 90 percent by weight of the compound or at least 90 percent by weight of the total amount of the compound present in a composition. It is anticipated in that in certain embodiments, compositions of the invention will comprise both: i) a total amount of a compound wherein 90% of that total amount of the compound present in the composition is an enantiomeric form of the compound that inhibits HCV replication and ii) other ingredients. Other embodiments of the present invention are drawn to compounds, compositions, and methods of use wherein the enantiomeric form of the compound that inhibits HCV replication is at least 95 percent by weight of the compound or at least 95 percent by weight of the total amount of the compound present in a composition. Still other embodiments of the present invention are drawn to compounds, compositions, and methods of use wherein the enantiomeric form of the compound that inhibits HCV replication is at least 97.5, 98, 99, 99.5, or 99.9 percent by weight of the compound or at least 97.5, 98, 99, 99.5, or 99.9 percent by weight of the total amount of the compound present in a composition.

It is contemplated that the compounds of formula (I) can be used as laboratory reagents. Such compounds may be instrumental in providing research tools for designing viral replication assays, validation of animal assay systems and structural biology studies to further enhance knowledge of HCV disease mechanisms. Further, it is contemplated that the compounds of the present invention can be useful in establishing or determining the binding site of other antiviral compounds, for example, by competitive inhibition.

It is also contemplated that the compounds of formula (I) can be used to treat or prevent viral contamination of materials and therefore reduce the risk of viral infection of laboratory or medical personnel or patients who come in contact with such materials such as blood, tissue, surgical instruments and garments, laboratory instruments and garments, and blood collection or transfusion apparatuses and materials.

Further, the compounds of formula (I) and enantiomeric forms thereof that inhibit HCV replication can be used for the manufacture of a medicament for treating HCV infection in a patient.

Various prodrugs, solvates, and salts of compounds of formula (I) are also provided herein. Pharmaceutically acceptable salts of compounds of formula (I) are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization. U.S. Pat. No. 7,196,111 (filed Jun. 2, 2003) lists non-limiting exemplary acid addition salts and non-limiting exemplary basic salts contemplated herein.

Synthesis of Compounds of Formula (I)

Compounds of formula (I) can be synthesized according to methods known to those skilled in the art. For example, non-limiting embodiments can be prepared according to the methods reported in Dalinger et al., J Comb Chem 7:236-245 (2005). Scheme 1 is a general synthetic scheme for compounds of formula (I) that shows that a wide variety of compounds of the formula (I) can be synthesized by condensation of 5-aminopyrazole 1 derivatives with substituted β-diketones 2 to assemble pyrazolo[1,5-a]pyrimidine 3. Further treatment with sodium borohydride selectively reduces the pyrimidine ring resulting in the final compounds of formula (I). This reduction results in a racemic mixture that is diasteriopure. Dalinger et al., (2005) report that a racemic mixture of the 2,4-syn isomer is formed (i.e. enantiomers where $R_1$ and $R_2$ of formula (I) are in one of the two syn configurations).

Scheme 1. General synthetic scheme to compounds with the formula (I).

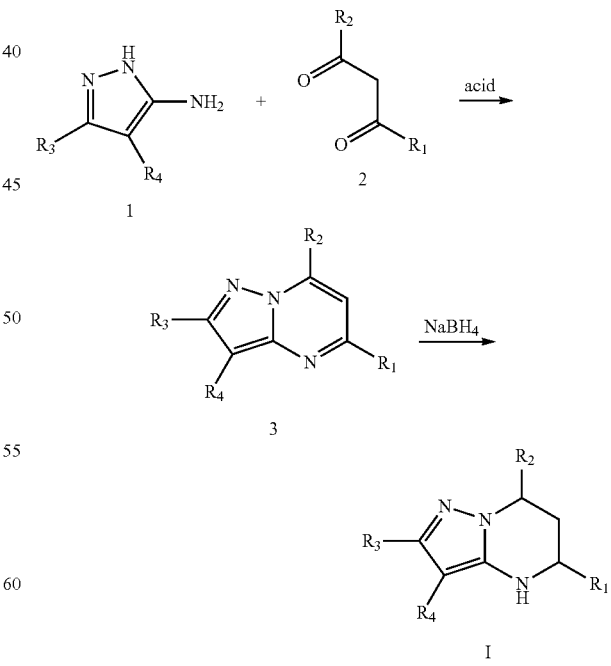

A wide variety of 5-aminopyrazole 1 derivatives for use as intermediate building blocks in the synthesis of the scaffold of compounds of formula (I) may be obtained commercially or synthetically. Commercially available examples include, but are not limited to, where $R_3$ is methyl and $R_4$ is bromine (Anichem LLC, North Brunswick, N.J., USA), where $R_3$ is methyl and $R_4$ is phenyl (American Custom Chemicals Corp., San Diego, Calif., USA), or where $R_3$ is phenyl and $R_4$ is bromine (Maybridge Chemical Co., Ltd., Geel, Belgium). Other 5-aminopyrazole derivatives where the 4 position of the aminopyrazole is alkylated or substituted with aryl or heteroaryl are synthetically accessible and could be used to synthesize compounds of formula (I) where $R_4$ is alkyl, aryl, or heteroaryl substituent. Exemplary non-limiting examples of 5-aminopyrazoles where $R_3$ is aryl and $R_4$ is aryl are described by Zhou et al., (J. Med. Chem. 2007 Jan. 25, 50(2): 399-403). Exemplary and non-limiting examples of 5-aminopyrazoles where $R_3$ is haloalkyl and $R_4$ is aryl are described in U.S. Pat. No. 4,122,278, hereby incorporated by reference in it's entirety. Solid state synthetic schemes for production of various 5-aminopyrazoles have also been described (Wilson et al., Tetrahedron Letters 1998, 39:2827-2830; Hwang, et al., J. Comb. Chem. 2005, 7, 136-141). Syntheses of 5-aminopyrozole-4-carboxylate derivatives are described in U.S. Pat. No. 6,235,911. The 5-aminopyrozole-4-carboxylate derivatives described in U.S. Pat. No. 6,235,911, hereby incorporated by reference in it's entirety, include those where $R_3$ is a straight or branched $C_1$-$C_4$ alkyl that is either unsubstituted or substituted with halogen. Synthesis of 3(5)-Aminopyrazole has also been described (Egwe and Arnold, Angewandte Chemie International Edition in English, 1974, 13(3): 206-207).

Synthesis of β-diketones for use as intermediate building blocks in the synthesis of the scaffold of compounds of formula (I) is know in the art. For example, Dalinger et al., (2005) disclose the use of fourteen exemplary and non-limiting trifluoromethyl-β-diketones. Scheme 2 is a general scheme showing the synthesis of β-diketones 2 for use in the synthesis of compounds of formula (I). β-diketones 2 can be synthesized from a corresponding methylketone derivative 5 and an appropriate carboxylate ester 4 under the Claisen condensation conditions as described in the literature.

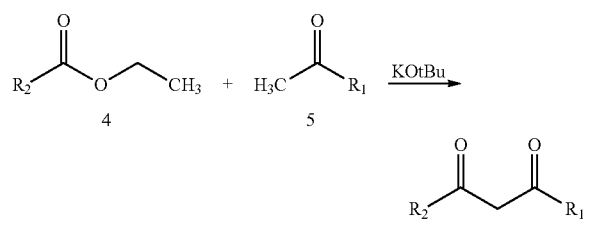

Scheme 2.

In Scheme 2, $R_1$ can be a substituted aryl, unsubstituted aryl, substituted heteroaryl, unsubstituted heteroaryl, substituted or unsubstituted alkyl, polyhaloalkyl, substituted or unsubstituted arylalkyl, substituted or unsubstituted heteroarylalkyl, or a substituted or unsubstituted cycloalkyl group while $R_2$ can be a polyhaloalkyl, substituted aryl, unsubstituted aryl, substituted heteroaryl, unsubstituted heteroaryl, substituted arylalkyl, unsubstituted arylalkyl, substituted heteroarylalkyl or unsubstituted heteroarylalkyl group. Polyhaloalkyls at $R_2$ include trifluoromethyl, trichloromethyl, tribromomethyl, difluorochloromethyl, difluorobromomethyl, difluoroiodomethyl, dichlorofluoromethyl, and dibromofluoromethyl groups. Scheme 2-1 depicts a non-limiting exemplary scheme of a the synthesis of a trifluoromethyl-β-diketone 7 where $R_2$ is trifluoromethyl.

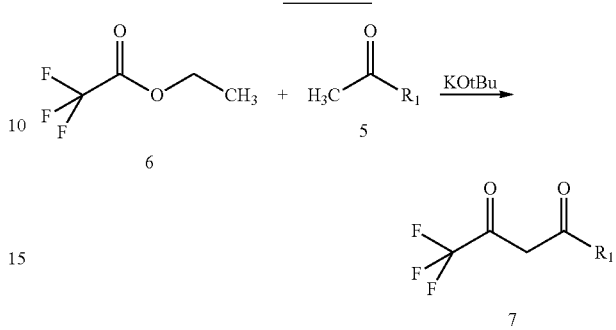

Scheme 2-1

Compounds of formula (I) where $R_3$ is a substituent other than a carboxamide can be synthesized by using a variety commercially and synthetically available 5-aminopyrazole derivatives as described above in Scheme 1. In such schemes, $R_3$ can be a substituted aryl, unsubstituted aryl, substituted heteroaryl, unsubstituted heteroaryl, substituted alkyl, unsubstituted alkyl, cycloalkyl, substituted arylalkyl, unsubstituted arylalkyl, heteroalkyl, alkoxy, alkyl thio, aryloxy, hydrogen, amino, carboxy, or other group that is not a carboxamide.

Compounds of formula (I) where $R_3$ is a carboxamide or carboxyamide derivative and their synthesis have also been described (Dalinger et. al., 2005). The 3-carboxy-5-aminopyrazole 12 intermediates can be used, as described in Dalinger et. al., (2005), to synthesize 4,5,6,7-tetrahydropyrazolo[1,5] pyrimidine carboxyamide compounds of formula (I). An exemplary synthesis of 3-carboxy-5-aminopyrazole 12 intermediates, wherein $R_4$ is chlorine or bromine is depicted in Scheme 3.

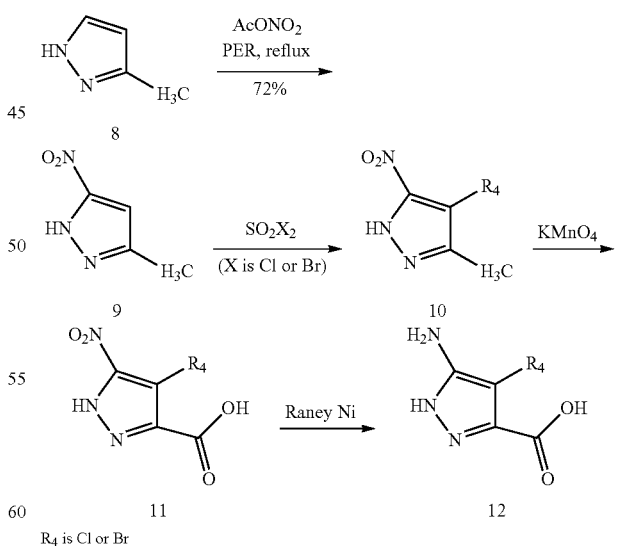

Scheme 3

$R_4$ is Cl or Br

Nitration of methylpyrazoles with $HNO_3$ normally does not proceed at the 3 position and often dinitration is found (S. A. Shevelev, I. L. Dalinger: Russ. J. Org. Chem. 34 (1998) 1071-80). Therefore acetyl nitrate needs to be used to obtain first the N-nitro compounds (J. W. A. M. Janssen et al., J. Org. Chem. 38 (1973) 1777-82). These N-nitro compounds are then rearranged by heating to the 3-nitro compounds via an anionotropic 1,5-shift ((a) see Shevelev and Dalinger (1998), (b) J. W. A. M. Janssen, C. L. Habraken: J. Org. Chem. 36 (1971) 3081-4).

Halogen $R_4$ substituents such as chlorine or bromine can be introduced with sulfuryl chloride or surfuryl bromide, respectively, by extended heating to reflux. Oxidation of the methyl intermediate 8 to the acid 9 with potassium permanganate or dichromate is described in the literature. The transformation of the nitro group to the corresponding amine can be accomplished, for example, by Raney-Ni reduction with either hydrazine or with pressurized hydrogen gas as a hydrogen source in this reduction. The above described synthetic scheme can also be used for the synthesis of the intermediate 12, wherein $R_4$ is hydrogen, when the intermediate 9 is directly transformed, without a halogenation step, directly to carboxylic acid 11.

Scheme 4 is a general synthetic scheme that shows that a wide variety of 4,5,6,7-tetrahydropyrazolo[1,5-a]pyrimidine carboxyamide compounds of the formula (I) can be synthesized by condensation of 3-carboxy-5-aminopyrazole 12 derivatives with substituted β-diketones 2 to assemble pyrazolo[1,5-a]pyrimidine carboxylates 13. The pyrazolo[1,5-a]pyrimidine carboxylates 13 can then be converted into libraries of amide derivatives 14 via reaction of the corresponding acid chlorides with appropriate amines. Further treatment with sodium borohydride selectively reduces the pyrimidine ring resulting in the final 4,5,6,7-tetrahydropyrazolo[1,5-a]pyrimidine carboxyamide compounds of formula (I).

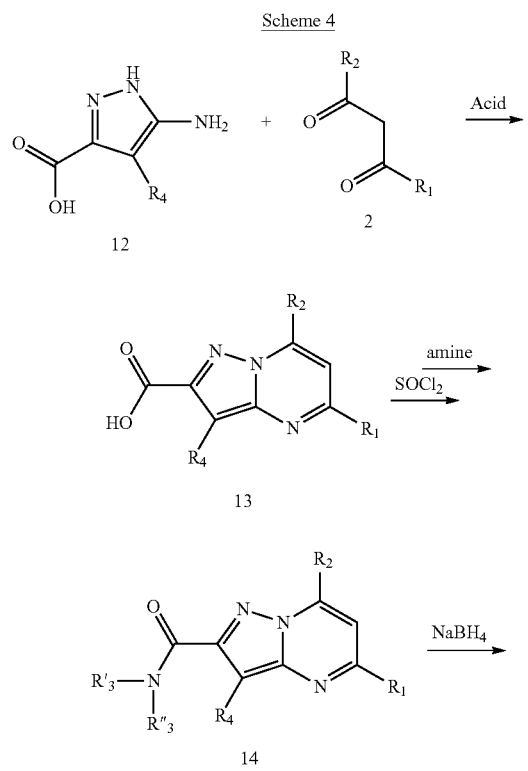

Scheme 4

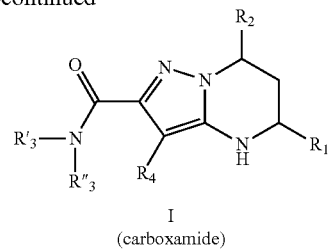

I
(carboxamide)

Diversity of the generic core structure of formula (I):

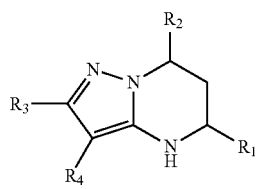

can be achieved by varying the substituents at the $R_1$, $R_2$, $R_3$, and $R_4$ positions. The following section provides illustrative and non-limiting examples of how diversity at the $R_1$, $R_2$, $R_3$, and $R_4$ positions can be achieved. Examples of compounds used in the present invention can be synthesized according to the reaction schemes disclosed herein, or by modifications thereof that are routine to those skilled in the art.

Substituents at the $R_1$ position. The $R_1$ position of formula (I) originates from the corresponding $R_1$ group present in the β-diketone intermediate 2 chosen to form the initial pyrazolo [1,5-a]pyrimidine ring. Different substituents at the $R_1$ position can thus be selected by the use of different β-diketone intermediates. For example, Dalinger et al., (2005) disclose the following fourteen $R_1$ groups of trifluoromethyl-β-diketone intermediates: phenyl, 4-methylphenyl, 4 chlorophenyl, 4-fluorophenyl, 4-bromophenyl, 4-methoxyphenyl, 3-methoxyphenyl, 2-methoxyphenyl, 3,4-dichlorophenyl, 3,4-dimethoxyphenyl, 4-nitrophenyl, 1,3-benzodioxol-5-yl, 2-furyl, and 2-thienyl. To obtain other substituents at the $R_1$ position of formula (I), β-diketone intermediates 2 where $R_1$ is an alkyl, a polyhaloalkyl, a cycloalkyl group can be used. Polyhaloalkyls at $R_1$ can thus include trifluoromethyl, trichloromethyl, tribromomethyl, difluorochloromethyl, difluorobromomethyl, difluoroiodomethyl, dichlorofluoromethyl, and dibromofluoromethyl groups.

Substituents at the $R_2$ position. The $R_2$ position of formula (I) originates from the corresponding $R_2$ group present in the β-diketone intermediate 2 chosen to form the initial pyrazolo [1,5-a]pyrimidine ring. Different substituents at the $R_2$ position can thus be selected by the use of different β-diketone intermediates. Dalinger et al., (2005) disclose the use of a β-diketone intermediate 7 where $R_2$ is a trifluoromethyl group. To obtain other substituents at the $R_2$ position of formula (I), β-diketone intermediates 2 where $R_2$ of the β-diketone is a polyhaloalkyl other than trifluoromethyl, a substituted aryl, an unsubstituted aryl, a substituted heteroaryl, or an unsubstituted heteroaryl groups can be used. Polyhaloalkyls at $R_2$ can thus include trifluoromethyl, trichloromethyl, tribromomethyl, difluorochloromethyl, difluorobromethyl, difluoroiodomethyl, dichlorofluoromethyl, and dibromofluoromethyl groups.

Substituents at the $R_3$ position. As previously described, compounds of formula (I) where $R_3$ is a substituent other than a carboxamide can be synthesized using a variety of commercially and synthetically available 5-aminopyrazole derivatives. For example, $R_3$ can comprise substituents such as hydrogen, alkyl, polyhaloalkyl, substituted aryl, unsubstituted aryl, substituted heteroaryl, and unsubstituted heteroaryl. Compounds of formula (I) where the $R_3$ position is a carboxamide may also be synthesized by, for example, condensation of 3-carboxy-5-aminopyrazole 12 derivatives with corresponding β-diketones to assemble pyrazolo[1,5-a]pyrimidine carboxylates. These acids can then be converted into corresponding chlorides at the $R_3$ position. The subsequent chlorides can then be easily converted into corresponding amide derivatives by reaction with diverse primary and secondary amines. Dalinger et al., (2005) describe the use of 450 different amine components and report that various aliphatic and aromatic amines, such as substituted anilines and benzylamines, heteroarylamines, cyclic and acyclic aliphatic amines, and nitrogen-containing compounds were tolerated without any limitations.

Substituents at the $R_4$ position. As with the $R_3$ position, the $R_4$ position of formula (I) originates from the 5-aminopyrazole intermediate chosen to form the initial pyrazolo[1,5-a] pyrimidine ring. Dalinger et al., (2005) disclose the use of a 3-carboxy-5-aminopyrazole intermediate to synthesize compounds of formula (I) wherein $R_4$ is a hydrogen, and use of a 4-chloro-substituted analog to synthesize compounds of formula (I) wherein $R_4$ is a chlorine. Other 3-carboxy-5-aminopyrazole intermediates where the $R_4$ is halogenated with either fluorine, bromine, or iodine can also be used to synthesize compounds of formula (I) where $R_4$ is fluorine, bromine, or iodine. Compounds of formula (I) can also be synthesized using a variety of commercially and synthetically available 5-aminopyrazole derivatives as previously described. Such derivatives, for example, can yield compounds of formula (I) where $R_4$ is alkyl, substituted aryl, unsubstituted aryl, substituted heteroaryl, and unsubstituted heteroaryl.

Methods for Obtaining Enantiomeric Forms of Compounds of Formula (I) that Inhibit HCV Replication and that are Substantially Free of Enantiomeric Forms that do not Inhibit HCV Replication The compounds of formula (I) include asymmetric carbon atoms and can therefore exist as single stereoisomers, racemates, and as mixtures of enantiomers and diastereomers. As shown herein, one particular enantiomeric form of certain compounds of formula (I) wherein $R_1$ and $R_2$ are in a syn configuration inhibits HCV replication. The other enantiomeric form wherein $R_1$ and $R_2$ are in a syn configuration does not inhibit HCV replication. Compounds of formula (I) with the particular enantiomeric configuration that inhibits HCV replication can be isolated in a form that is substantially free of the enantiomeric configuration that does not inhibit HCV replication. Compounds of formula (I) with the particular enantiomeric configuration that inhibits HCV replication may also be prepared in a form that is substantially free of the enantiomeric configuration that does not inhibit HCV replication.

Enantiomeric forms of compounds of formula (I) can be isolated by a variety of methods known to those skilled in the art. Methods of isolation include, but are not limited to, various chiral chromatography methods. In one embodiment, separation of the enantiomers is effected with a chromatographic system that comprises a chiral stationary phase. In other embodiments, separation of the enantiomers can be effected with a chromatographic system that comprises a chiral mobile phase or mobile phase wherein a chiral additive is provided. In still other embodiments, various combinations of chiral mobile phases, chiral stationary phases, and/or mobile phases with one or more chiral additives can be used to separate the enantiomers formation of diastereoisomeric salts which may be separated by crystallization, gas-liquid or liquid chromatography, and selective reaction of one enantiomer with an enantiomer-specific reagent. Column liquid chromatography, thin-layer chromatography, supercritical fluid chromatography, electromigration methods, counter current liquid chromatography and liquid-liquid can all be employed to separate enantiomers as described by Davankov (Pure and Applied Chemistry 69,1469-1474, 1996) and references cited therein.

Alternatively, specific enantiomers may be synthesized by using optically active reagents, substrates, catalysts or solvents, or by converting one enantiomer into the other by asymmetric transformation. Methods for asymmetric synthesis are described in "Comprehensive Asymmetric Catalysis" (Jacobsen, E. N., Pfaltz, A., Yamamoto, H., Pub. Springer, 2004).

These purification or synthetic methods can be used to provide compounds or compositions wherein the enantiomeric form of the compound that inhibits HCV replication is at least 90, 95, 97.5, 98, 99, 99.5, or 99.9 percent by weight of the compound or at least 90, 95, 97.5, 98, 99, 99.5, or 99.9 percent by weight of the total amount of the compound present in a composition.

Identification of Compounds that Inhibit HCV Replication

Compounds of the present invention have been found to be useful in methods for inhibiting HCV replication. Such methods comprise contacting a cell that harbors either an infectious HCV genome, an HCV genomic replicon, or an HCV sub-genomic replicon with a compound or composition provided herein and determining the effect of the compound or composition on the quantities of the infectious HCV genome, an HCV genomic replicon, or an HCV sub-genomic replicon in the cells treated with the compound or composition.

In certain embodiments, the cell is a cultured cell that is capable of supporting replication of a subgenomic HCV replicon. Cells that harbor subgenomic HCV genotype 1b replicons are described in Lohmann et al., Science 285: 110-113 (1999), Blight et al., Science 290: 1972 (2000), Bartenschlager and Lohmann, J. Gen. Virology 81: 8631-1648 (2000), and elsewhere. Cells that harbor subgenomic HCV genotype 1a replicons are described in Blight et al., J. Virol. 77:3181-3190 (2003), and elsewhere. Cells that harbor HCV genotype 1a and genotype 1b genomic replicons have also been described (Blight et al., J. Virol. 77:3181-3190 (2003), Ikeda et al., J. Virol. 76:2997-3006 (2997), and Pietschmann et al., J. Virol. 76:4008-4021 (2002).

In other embodiments, the cell is a cultured cell that harbors an infectious HCV genome. Cells harboring HCV genotype 1a or genotype 1b genomes that are infectious have been described (Kato et al., J. Virol. 81:4405-4411 (2007).

Inhibitory effects of a given compound can be determined by quantitating the effect of the compound on levels of the infectious HCV genome, an HCV genomic replicon, or an HCV sub-genomic replicon in treated cells. As these various replicating forms of HCV comprise RNA, any method whereby levels of a specific RNA in a cell is measured can be used. When quantitating HCV RNA by use of a quantitative reverse-transcriptase Polymerase Chain Reaction (qRT-PCR), the HCV-derived PCR product can be detected by use of any labelled polynucleotide probes, by use of an intercalating dye such as ethidium bromide or SYBR green, use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, Calif.) or use of methods where the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, S. A.; Journal of Molecular Endocrinology 29, 23, 2002). Fluorescent probes that are activated by the action of enzymes that recognize mismatched nucleic acid complexes (i.e., Invader™, Third Wave Technologies, Madison, Wis.) can also be used to quantitate RNA. Commercially available kits for quantitating HCV RNA include the COBAS™ TaqMan HCV Test (TaqMan HCV; Roche Molecular Systems, Inc., Branchburg, N.J.) and the Versant HCV bDNA test (Bayer Diagnostics, Tarrytown, N.Y.).

Quantitation of the effect of the compound on levels of the infectious HCV genome, an HCV genomic replicon, or an HCV sub-genomic replicon in treated cells can also be effected by measuring a protein product encoded by any of those forms of the HCV genome. Thus, any of an HCV Core protein, structural protein, or non-structural protein encoded by the particular form of the HCV genome present in the cell can be measured to quantitate compound effects on HCV replication. Proteins encoded by the HCV genome can be measured by suitable antibody-based assays or other techniques. In other embodiments, an HCV genomic replicon or HCV sub-genomic replicon in the cell can further comprise a selectable marker gene whose protein product can be measured to quantitate compound effects on HCV replication. In certain embodiments, an HCV genomic replicon or HCV sub-genomic replicon in the cell can further comprise a reporter gene that encodes an assayable product. Examples of reporter genes in HCV replicons include genes that encode Renilla luciferase, firefly luciferase, beta-lactamase, and secreted alkaline phosphatase. Reporter gene expression can be quantitated by appropriate enzymatic assays to determine the effects of a compound on HCV replication.

Pharmaceutical Compositions Comprising Compounds of Formula (I)

In practicing any of the methods of the present invention involving administration of HCV inhibitory, preventative, or mitigating agents to a subject, it is contemplated that a variety of pharmaceutical compositions comprising these active compounds can be administered by a variety of techniques. Such pharmaceutical compositions may be formulated in various ways known in the art for administration purposes. To prepare pharmaceutical compositions, a therapeutically effective amount of a compound or compounds of formula (I) or an enantiomer, diastereomer, salt, solvate, or prodrug thereof, is combined with one or more pharmaceutically acceptable carriers and/or delivery vehicles. The active ingredient, i.e., compound, in such compositions typically comprises from about 0.1 percent by weight to about 99.9 percent by weight of the composition, and often comprises from about 5 percent by weight to about 95 percent by weight. Numerous pharmaceutically acceptable carriers and delivery vehicles exist that are readily accessible and well known in the art. Non-limiting illustrative examples of pharmaceutically acceptable carriers and delivery vehicles include aluminum stearate, lecithin, serum proteins such as human serum albumin, buffer substances such as the various phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, cellulose-based substances, polyethylene glycol, sodium carboxymethylcellulose, polyacrylates, waxes, polyethylene, polyoxypropylene-block polymers, polyethylene glycol and wool fat, and the like. The pharmaceutical compositions described herein may further be prepared in a form suitable for administration orally, percutaneously, by parenteral injection (including subcutaneous, intramuscular, intravenous and intradermal), topically, intranasally, by inhalation, or for application to a medical device, such as an implant, catheter, or other device. Oral administration or administration by injection are generally preferred. In preparing compositions that permit oral delivery of liquid preparations such as suspensions, syrups, elixirs and solutions, any of the pharmaceutically acceptable carriers known in the art may be used such as but not limited to, water, glycols, oils, alcohols and the like. When solid pharmaceutically acceptable carriers are desired, such as those that permit oral or rectal administration; starches, sugars, kaolin, lubricants, binders, cellulose and its derivatives, and disintegrating agents and any other pharmaceutically acceptable carriers known in the art may be used to prepare, for example, powders, pills, capsules and tablets. For pharmaceutically acceptable compositions and preparations that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient. The preparation of pharmaceutically acceptable formulations is described in. e.g., *Remington: The Science and Practice of Pharmacy*, $20^{th}$ Ed., ed. A. Gennaro, Lippincott Williams & Wilkins, 2000.

Compounds of formula (I) may be used to treat or prevent HCV infection in combination with one another, or with at least one additional biologically active agent. Non-limiting illustrative examples of biologically active compounds or agents that can be combined with compounds of formula (I) include, interferon-alpha, interferon-beta, interferon-gamma, pegylated interferons, ribavirin and related compounds, amantadine and related compounds, viral protease inhibitors, viral polymerase inhibitors, antiviral small interfering RNA compounds, anti-sense antiviral compounds, nucleotide analogs, nucleoside analogs, immunoglobulins, immunomodulators, hepatoprotectants, anti-inflammatory agents, antibiotics, antivirals, and anti-infective compounds. Compounds of formula (I) may also be used in combination with antiviral compounds or agents including, but not limited to, acyclovir, famicyclovir, valganciclovir and related compounds. Additionally, combinations of, for example, ribavirin and interferon, may be administered as an additional combination for a multiple combination therapy with at least one compound of formula (I). It is intended that combination therapies of the present invention include any chemically compatible combination of a compound of formula (I) with other biologically active compounds or biologically active agents, as long as the combination does not eliminate the anti-viral activity of the compound of formula (I) or the anti-viral activity of the pharmaceutical composition itself. Certain non-limiting illustrative compounds that can be administered with the compounds of this disclosure including certain other HCV inhibitor compounds are disclosed in U.S. patent application Ser. No. 11/430,611 filed May 9, 2006 and the publications cited therein.

Methods of Treating or Preventing HCV infections

Certain aspects of the current disclosure provide methods for treating or preventing an HCV viral infection, the methods comprising administering to a subject infected with HCV a therapeutically effective amount and/or a prophylactically effective amount of at least one HCV inhibitory compound or composition according to the present invention. Treatment and/or prevention of HCV genotype 1 infections with compounds and/or compositions provided herein is contemplated. HCV genotype 1 infections that comprise infections with HCV genotype 1a, HCV genotype 1b, or combinations of both HCV genotypes 1a or 1b can be treated or prevented with compounds and/or compositions provided herein.

Administration of a combination of one or more of the compounds of the present invention and one or more additional biologically active agents and/or potentiators thereof is also contemplated. Administration of a combination can be sequential, wherein treatment with one agent is done before treatment with a second agent. Alternatively, administration can be concurrent where treatment with two or more agents occurs at the same time. Sequential administration can be done within a reasonable time after the completion of a first therapy before beginning a second therapy. Administration of multiple agents concurrently can be in the same daily dose or in separate doses.

The pharmaceutical compositions of the present invention may be formulated into a variety of dosage forms depending upon the particular composition contemplated. Likewise, a variety of modes of administration are possible depending upon the particular composition and dosage form, although oral administration by tablet, capsule or suspension are the preferred modes of administration.

Therapeutically effective amounts of a compound of formula (I), a pharmaceutical composition thereof, or a combination therapy will depend on absorption, distribution, metabolism, and excretion rates of the components of the therapy as well as other factors known to one of skill in the art. Dosage values will also vary with the severity of the condition to be alleviated. It is further understood that for any particular subject, specific dosage regimens and schedules may be adjusted over time according to the individual's need and the professional judgment of the person administering or supervising the administration. The therapeutically effective amount of the inhibitory compound administered will be determined empirically, and will also be based on considerations such as the particular inhibitor or combination used, the age, sex, diet, body weight, and general health status of the individual, the treatment effect desired, administration route, the severity and course of the infection, and the like. It is expected that the typical dose range will be from about 0.1 mg/kg to about 100 mg/kg per dose, which can be given one to several times per day, or alternatively as a continuous infusion. Such administration can be used as a chronic or acute therapy.

When the compositions comprise a combination of a compound of formula (I) and one or more additional biologically active agent, both the compound and the additional agent are usually present at dosage levels of between about 10 to 100%, and more preferably between about 10 and 80% of the dosage normally administered in a monotherapy regimen.

Therapeutically effective amounts of compounds and/or compositions provided herein can be determined by any of a variety of biological markers of HCV infection. In certain embodiments, the therapeutically effective amounts can be determined by assessing the HCV viral load prior to and after treatment. Commercially available kits for quantitating HCV RNA include the COBAS™ TaqMan HCV Test (TaqMan HCV; Roche Molecular Systems, Inc., Branchburg, N.J.), the COBAS Amplicor HCV Monitor test (Roche Molecular Systems, Inc., Branchburg, N.J.), and the Versant HCV bDNA assay (Bayer Diagnostics, Tarrytown, N.Y.). Such HCV viral load quantitation systems and their monitoring the therapeutic efficacy of HCV treatment regimens is described by Konnick et al., J Clin Microbiol. 43(5): 2133-2140 (2005) and references cited therein.

Kit for Treating or Preventing a Hepatitis C Viral Infection

In certain embodiments contemplated herein, kits comprising at least one pharmaceutical composition of a compound or combination of compounds of the invention and one or more pharmaceutically acceptable carriers, as well as one or more containers are provided.

The composition(s) of the kit that comprise a compound of formula (I) may be provided in any form. Composition forms provided in the kit can include, but are not limited to, tablets, capsules, pills, liquid solutions or dried powders. In certain embodiments where the composition(s) are provided in a liquid solution, such liquid solution can be for example an aqueous solution. When the composition(s) provided are a dry powder, the powder can be reconstituted by the addition of a suitable solvent, that can also be provided.

The container will generally include a vial into which the pharmaceutical composition may be placed, and preferably suitably aliquotted. The kits of the present invention will also typically include a means for containing the composition(s) in a container in close confinement for commercial sale. Such containers may include injection or blow-molded plastic containers into which the desired vials are retained.

The kit can also comprise a device or a component of a device for performing the methods of the invention. Devices, or components of devices, include, but are not limited to, syringes and other implements useful for delivery of the composition to the blood stream or a specific organ, e.g. the liver. In certain embodiments, the compositions of the invention can be provided in unit dose form. In addition or in the alternative, the kits of the invention can provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration. Instructions can also be provided as a fixed, fully detachable, or partially detachable label that is associated with one or more containers in the kit. The instructions associated with the kit can provide directions for preparing the pharmaceutical composition for administration and/or instructions for administration of the pharmaceutical composition to a subject in need thereof.

Isolated Nucleic Acid for Detecting HCV Genotype Variants

Various HCV genotypes, subtypes, isolates, and/or quasispecies may exhibit varying responses to HCV inhibitory agents. In particular, it has been discovered that an amino acid residue other than a phenylalanine at a position corresponding to amino acid residue 1809 of an HCV polyprotein (SEQ ID NO:9) confers resistance to the compounds of the present invention. Certain embodiments of the present invention include nucleic acid probes that encode a residue other than phenylalanine at a position corresponding to amino acid residue 1809 of SEQ ID NO:9. Other embodiments of the present invention include nucleic acid probes that comprise 1, 2, or 3 nucleotides of a codon corresponding to the codon encoding phenylalanine at a position corresponding to amino acid residue 1809 of SEQ ID NO:9, wherein the codon or portion thereof does not encode phenylalanine.

Methods for Detecting Resistant HCV Variants

Those of skill in the art will appreciate that it can be useful to determine if a subject has a type of HCV that is sensitive or resistant to a particular compound, agent, composition, or the like to inform a physician or other person treating the subject as to which compounds, agents, compositions, combinations of treatment, and the like will be most effective. It is also useful to monitor during the course of treatment whether the formerly sensitive HCV infecting a subject has developed resistance to the active compounds comprising the treatment. It has been discovered that HCV comprising an amino acid other than phenylalanine at amino acid residue 1809 of an HCV polyprotein reference sequence of SEQ ID NO:9 are resistant to certain compounds of formula (I). Methods of detecting HCV that are either sensitive or resistant to the compounds of formula (I) are thus contemplated. Such methods can use any method for genotyping HCV to determine if HCV present in a sample contains a mutation that confers resistance to a compound of formula (I). In certain embodiments, an isolated nucleic acid that encodes a residue other than phenylalanine at a position corresponding to amino acid residue 1809 of SEQ ID NO:9 is used to detect HCV mutants that are resistant to the compound of formula (I). In other embodiments of the present invention, nucleic acid probes that comprise 1, 2, or 3 nucleotides of a codon corresponding to the codon encoding phenylalanine at a position corresponding to amino acid residue 1809 of SEQ ID NO:9, wherein the codon or portion thereof does not encode phenylalanine, are used to detect HCV mutants that are resistant to the compound of formula (I). In still other embodiments of the present invention, nucleic acid probes that hybridize to sequences immediately adjacent to a codon encoding phenylalanine at a position corresponding to amino acid residue 1809 of SEQ ID NO:9 are used to detect HCV mutants that are resistant to the compound of formula (I). Nucleic acid probes that hybridize to sequences immediately adjacent to a codon encoding phenylalanine at a position corresponding to amino acid residue 1809 of SEQ ID NO:9 are anticipated to be useful in detection of HCV that are sensitive or resistant to compounds of formula (I), by use in single base extension reaction assays that are routinely used to detect single nucleotide polymorphisms (SNP). However, it is similarly anticipated that the single nucleotide mutations disclosed herein that confer resistance to compounds of formula (I) can be detected by any suitable assay that permits discrimination of SNPs.

Kits for Detecting HCV Genotype Variants

It is contemplated that nucleic acid probes for detecting HCV genotype variants be provided in a kit for diagnostic use. In some embodiments, such probes can further be packaged with additional reagents in a kit. The provided reagent(s) in such kit can be radio-, spectrophotometrically-, fluorescently-, or enzymatically labelled. The provided reagents can also be detectably labelled by other materials. The provided reagents may include a substrate that is converted to a product that can be detected by spectrophotometry, luminometry, or fluorescence.

The reagents of the kit may be provided as a liquid solution, attached or otherwise deposited in or on a solid support, or as a dried powder. Preferably, when the reagent(s) are provided in a liquid solution, the liquid solution is an aqueous solution. Preferably, when the reagent(s) provided are attached to, or otherwise deposited on a solid support, the solid support can be chromatography media, a test plate having a plurality of wells, or a microscope slide. When the reagent(s) provided are a dry powder, the powder can be reconstituted by the addition of a suitable solvent, such as a buffer solution, that may be provided.

The container will generally include a vial into which the reagent(s) may be placed, and preferably suitably aliquotted. The kit of the present invention will also typically include a means for containing the reagent(s) in a container for commercial sale. Such containers may include injection or blow-molded plastic containers into which the desired vials are retained. It is also contemplated however, that such kits may be assembled not for commercial sale, but for internal use within a research group. Thus the usefulness of such kits is not restricted to commercial sales.

The instructions for the kit may either be enclosed in the kit or provided by way of reference to an external or internal website or other internal or external document or reference.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

The following examples are included to illustrate the synthetic procedures used for preparing compounds of the invention. In these examples, all chemicals and intermediates are either commercially available or can be prepared by standard procedures found in the literature or are known to those skilled in the art of organic chemical synthesis.

Example 1

Synthesis of the Compound AP0089652 and Separation of Enantiomeric Forms

The following example illustrates the synthetic procedures used to prepare the compound AP0089652. The schemes and procedures used to synthesize the intermediates are followed by the schemes and procedures used to synthesize compound AP0089652 from those intermediates.

Scheme 5: Synthesis of the intermediate 5-amino-4-chloro-1H-pyrazole-3-carboxylic acid 17

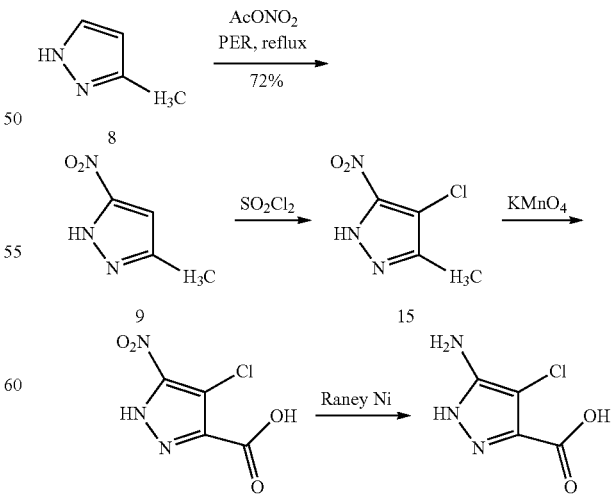

The preceding scheme illustrates the steps used to obtain the 5-amino-4-chloro-1H-pyrazole-3-carboxylic acid 17 intermediate.

Synthesis of the Intermediate 3-methyl-5-nitro-1H-pyrazole 9

Acetic anhydride (96.2 mL, 104.58 g, 1.02 mol) was cooled to −15° C. with an ice/NaCl bath and to this was dropwise, very slowly, added red fuming $HNO_3$ (40.7 mL, 61.8 g, 0.98 mmol). The reaction is strongly exothermic and care must be taken to keep the temperature below 0° C. (inside temperature). This solution was then rapidly transferred with a teflon tube of sufficient diameter (to prevent warming on transfer) to an addition funnel with a cooling mantle. This solution was kept <0° C. at all times and the addition funnel mounted on a flask containing methylpyrazole (35 g, 0.427 mol) in glacial acetic acid (40 mL) at −5° C. The chilled (−15° C.) acetyl nitrate solution was then dropwise added to the methylpyrazole 8 solution at 0° C. The reaction was highly exothermic until ca. 1 eq. acetyl nitrate had been added and it must not be allowed to warm above 5° C. After 3 hours stirring at 0° C. the mixture was poured into ice/water (500 mL) and neutralized to ca. pH 7 with sodium carbonate. Extraction with DCM (3×200 mL), drying (sodium sulfate) and evaporation in vacuo afforded a 90:10 mixture of N-nitro intermediates (42.8 g, 0.337 mol, 79%), which was dissolved in perchloroethylene (4 L), heated at 140° C. ext. temperature for 18 hours and for 5 hours at 165° C. Evaporation of the solvent and drying in vacuo gave pure 9 (39.0 g, 0.307 mol, 72% both steps).

It should be noted that nitration of methyl pyrazoles with $HNO_3$ normally does not proceed at the 3 position and often dinitration is found (S. A. Shevelev, I. L. Dalinger: Russ. J. Org. Chem. 34 (1998) 1071-80). Therefore acetyl nitrate had to be used to affect first the N-nitro compounds (J. W. A. M. Janssen et al.,: J. Org. Chem. 38 (1973) 1777-82). These N-nitro compounds were then rearranged by heating to the 3-nitro compounds via an anionotropic 1,5-shift ((a) see Shevelev and Dalinger (1998), (b) J. W. A. M. Janssen, C. L. Habraken: J. Org. Chem. 36 (1971) 3081-4). Mixtures of the two possible N-nitro compounds were observed in the nitration, however the 1,5-rearrangement led to interconversion, thus only one product (3-methyl-5-nitro-1H-pyrazole 9) was finally observed.

Synthesis of the Intermediate 4-chloro-3-methyl-5-nitro-1H-pyrazole 15

Nitropyrazole 9 (10.0 g, 78.68 mmol) was dissolved in a mixture of chloroform (500 mL) with 1 drop DMF. To this was added sulfuryl chloride (9.60 mL, 14.33 g, 118.0 mmol) and the mixture heated to reflux for 20 hour at 115° C. external temperature. After additional 48 hours stirring at ambient temperature the mixture was evaporated to dryness in vacuo, dichloromethane (250 mL) added and the solution again evaporated in vacuo. Crude 15 was purified by column chromatography (1 kg SiO2, 0-10% methanol in DCM) yielding pure 15 (11.7 g, 72.42 mmol, 92%).

Synthesis of the Intermediate 4-chloro-5-nitro-1H-pyrazole-3-carboxylic acid 16

$KMnO_4$ (34.3 g, 217 mmol) was added in 10 batches over 4 hours to a solution of 15 (11.7 g, 72.4 mmol) in water (300 mL) at 80-85° C. internal temperature. After another 1 hour at 80° C. and 16 hours at ambient temperature the reaction mixture was filtered through celite and the filter cake washed with warm water (200 mL). The filtrate was evaporated and dried in vacuo to afford crude 16 (18.5 g, max. 72.4 mmol), which contained some $MnO_2$ and was otherwise 85% pure acc. to HPLC-MS. Oxidation of the methyl of intermediate 15 to the acid required the use potassium permanganate in the particular experiments described in this Example. Oxidation of the methyl to acid did not occur with dichromate in the particular experiments described in this Example.

Synthesis of the Intermediate 5-amino-4-chloro-1H-pyrazole-3-carboxylic acid 17

Crude 16 (10.0 g, 52.2 mmol) was heated in water (100 mL) to 60° C. int. temperature. The product intermediate 16 contained manganese salts as an impurity, but could be used unpurified in the Raney-Ni reduction to obtain intermediate 17. To this solution was added Raney-Ni (7 g, 50% slurry in water) and dropwise over 4 hours a solution of hydrazine monohydrate (20 mL) in water (200 mL). Hydrazine was more effective as a hydrogen source in this reduction than hydrogen provided at 1 bar. After 1 hour at 60° C. int. temperature the mixture was allowed to cool to ambient temperature, filtered through celite, the filter cake washed with water (200 mL) and the combined filtrates evaporated and dried in vacuo to afford crude 17 (15 g, max. 52.2 mmol), which contained some Ni salts and was used unpurified in the next step.

Scheme 6: Synthesis of the diketone intermediate 4,4,4-trifluoro-1-(furan-2-yl)butane-1,3-dione 19

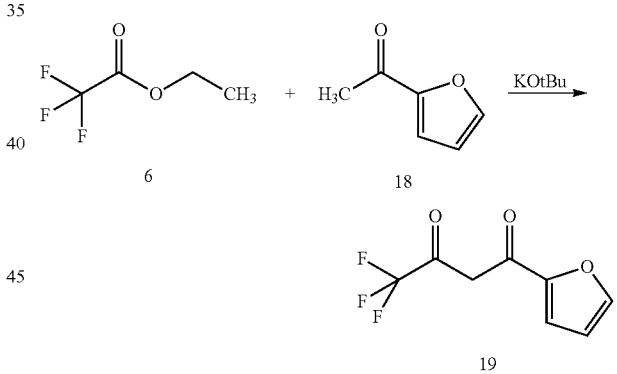

The diketone 19 was synthesized from acetylfuran and trifluoracetate to obtain the 4,4,4-trifluoro-1-(furan-2-yl)butane-1,3-dione 19 product as follows. 2-Acetylfuran 18 (11.0 g, 210 mmol) was dissolved in benzene (210 mL). At room temperature was added KOtBu (23.6 g, 210 mol). The resulting red solution was cooled to 5° C. Ethyl trifluoracetate 6 (25 mL, 29.8 g, 210 mmol) was added dropwise in approximately 20 minutes keeping the temperature below 15° C. Then the mixture was stirred for 16 hours at room temperature. The mixture was poured in ice-water (300 mL) containing concentrated sulfuric acid (5 g). The aqueous mixture was extracted with tBME (3×200 mL). The combined organic layers were washed with brine (200 mL), dried ($Na_2SO_4$) and concentrated to give a dark brown oil (20.8 g). The crude product was purified by kugelrohr distillation to give compound 19 (17.0 g, 39%) as a yellowish oil.

Scheme 7 for the synthesis of compound AP0089652:

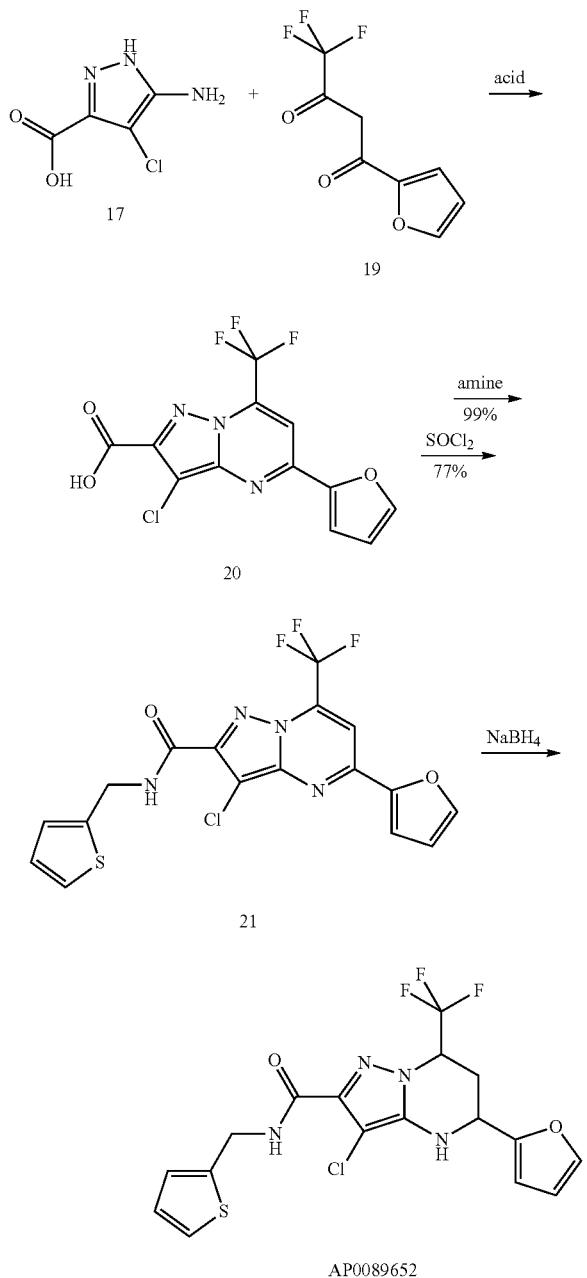

Synthesis of the Intermediate 3-chloro-5-(furan-2-yl)-7-(trifluoromethyl)pyrazolo[1,5-a]pyrimidine-2-carboxylic acid 20

Crude 17 (12.0 g, max. 41.8 mmol) and 19 (16.0 g, 77.6 mmol) were heated in a mixture of aqueous HCl (2N, 125 mL) and glacial acetic acid (150 mL) at 140° C. ext. temperature for 6 hours. After stirring over night at ambient temperature the formed residue was filtered off, washed with cold water (50 mL), dissolved in ethyl acetate (50 mL)/toluene (50 ml) and again evaporated in vacuo to give pure 20 (7.45 g, 22.46 mmol, 54%).

Synthesis of the Intermediate 3-chloro-5-(furan-2-yl)-N-(thiophen-2-ylmethyl)-7-(trifluoromethyl)-1,2-dihydropyrazolo[1,5-a]-pyrimidine-2-carboxamide 21

The intermediate 20 (7.4 g, 22.31 mmol) was suspended in a mixture of toluene (150 mL) and DMF (0.1 mL), thionyl chloride (4.86 mL, 7.96 g, 66.9 mmol) added and the mixture heated to reflux for 8 hours. Evaporation of the solvent and drying in vacuo afforded the crude acid chloride (7.9 g, 21.58 mmol, 97%), which was suspended in hot DCM (100 mL) and crystallized at −20° C. overnight, yielding the pure acid chloride (6.25 g, 17.07 mmol, 77%) after filtration and drying in vacuo. This compound was dissolved in a mixture of $NEt_3$ (4.79 mL, 3.45 g, 34.15 mmol) and acetonitrile (150 mL). Thiophenethylamine (2.32 g, 20.5 mmol) was added at ambient temperature, the mixture stirred for 3 hours and then poured into water (150 mL). The formed precipitate was filtered off and washed with water (150 mL), aq. ammonia (2N, 100 mL) and ethanol (25 mL). Drying in vacuo afforded pure 21 (7.25 g, 16.99 mmol, 99%). C17H11F3N4O2S; MW 392.4; 1H-NMR 300 MHz, CDCl3) in accordance with chemical structure, HPLC purity 99.6, LC-MS [M+H]=393.

Synthesis of 3-chloro-5-(furan-2-yl)-N-(thiophen-2-ylmethyl)-7-(trifluoromethyl)-4,5,6,7-tetrahydropyrazolo[L5-a]pyrimidine-2-carboxamide (AP0089652)

The intermediate 21 (4.3 g, 10.07 mmol) was suspended in ethanol (50 mL), sodium borohydride (1.53 g, 40.3 mmol) was added and the suspension heated to 130° C. external temperature for 45 minutes. After 30 minutes stirring at room temperature glacial acetic acid (5 mL) was added (foaming) and the resulting heterogeneous mixture poured into water (200 mL). The precipitate was filtered off, washed with water (100 mL), ethanol (25 mL) and dried in vacuo to give crude AP0089652 (3.18 g, 7.38 mmol, 73%), which was purified by recrystallization from ethanol to yield analytically pure AP0089652 (1.55 g, 3.60 mmol, 36%). This compound has been prepared from the corresponding aromatic system using a NaBH4-reduction as described previously (Dalinger et al., 2005). Only one pair of diastereoisomers is formed in this step that corresponds to 2,4 syn-isomers. C17H14ClF3N4O2S, MW 430.83, 1H, 300 MHz, D6-DMSO) in accordance with chemical structure, HPLC purity 99.0%, LC-API-ES positive [M+H]=431.1.

Separation of the Enantiomers of AP0089652 to AP0080978 and AP0080977

The separation of the enantiomers was achieved by an HPLC chromatography method using a chiral column Chiralcel OD-H (20×250 mm; 5 μm) Daicel and heptane/2-propanol 50:50 as a mobile phase at the flow rate 6.0 ml/min; UV detection at 254 nm and run time 29 & 35 minutes. Injection: 2500 μl (containing 20 mg) was injected each run. For example the sample of 120 mg racemate was dissolved in a mixture of 5 ml 2-propanol and 10 ml MeOH. Using 50 runs a total of 1 g of racemate compound was separated into 373 mg and 400 mg of the two respective enantiomers, AP0080977 and AP0080978. One of these enantiomers is active in inhibiting hepatitis C viral replication whereas the other enantiomer lacked such activity. The enantiomer 2 (80978) that eluted at longer retention time under those conditions (tR=24.16 min) exhibits antiviral activity against HCV infection.

Enantiomer 2 (80978):

Molecular Formula: $C_{17}H_{14}ClF_3N_4O_2S$; MW: 430.83, colorless powder, H1-NMR is in accordance to the expected structure HPLC Purity: 99.4% [Column Zorbax Extended C-18 (50× 4.60 mm; 3.5 um; reverse phase conditions)

LC-API-ES: Observed [m/z]=430.80; 431.70; 432.60

Purity 97.9% by Chiral HPLC: Column Chiracel OD-H, mobile phase: heptane/Isopropanol 1:1, flow rate 0.5 ml·min)

Example 2

Analysis of HCV Inhibition Activity of AP0089652 and Separated Enantiomeric Forms Inhibition of HCV replication by AP0089652, AP0080978 (enantiomer 2 from Example 1) and AP0080977 (enantiomer 1 from Example 1) were assayed by exposing cells harboring an HCV genotype 1b replicons to the compounds and quantitating HCV replicon levels following exposure. The replicon used in these studies was a transient genotype 1b subgenomic replicon generated from the Con1 strain. In this replicon, the HCV internal ribosome entry site (IRES) within the 5' non-translated region (NTR) drives expression of the first 32 amino acids of the core protein fused to humanized Renilla luciferase (hRluc). The encephalomycarditis IRES lies 3' to the hRluc open reading frame (ORF) and drives expression of non-structural (NS) proteins NS3 through NS5B. Huh7.5 cells (U.S. patent application Ser. No. 10/534, 571) harboring this replicon were seeded into 96-well plates at 20,000 cells per well in medium containing 10% FBS, 1× penicillin/streptomycin, 1× non-essential amino acids, and 100 ng/ml Fungizone. After a four hour attachment period, compound was added to wells using a five point 3-fold serial dilution series with four replicate treatments per dose. Final DMSO percentage was 1% in a total volume of 200 ul. Compound-mediated HCV inhibition and toxicity were assayed 24 hours post-treatment using Renilla luciferase readout and an ATP viability assay (CellTiter-Glo, Promega, Madison, Wis., USA), respectively. Both $EC_{50}$ (i.e. concentrations at which a 50% reduction in replicon levels is observed relative to an untreated control) and $CC_{50}$ (i.e. concentration resulting in a 50% decrease in cell viability) values were determined. The results of these experiments are provided in Table 1.

To quantify the effect of compound on HCV RNA replicon levels by measuring HCV replicon RNA levels, the Clone VI cell line, a human hepatoma cell line that contains a stable genotype 1b (Con1 strain) subgenomic replicon with the adaptive Ser1179Ile mutation was used (U.S. Pat. No. 7,049, 428). Cells were seeded into 12-well plates (40,000 cells per well) in the absence of Geneticin™ (Invitrogen, Carlsbad, Calif., USA) and treated in triplicate four hours later with 20 μM compound, with a final DMSO percentage of 1% in a total volume of 1 ml. Total RNA was extracted 72 hours later, and HCV and GAPDH RNA levels were quantified via quantitative RT-PCR. The log 10 decrease in HCV RNA levels was quantified relative to GAPDH RNA levels using the comparative Ct (threshold cycle) method (Applied Biosystems, Foster City, Calif., USA).

TABLE 1

Inhibition of HCV replication by 89652, 80977, and 80978,

| AP# | Description | 24 hr $CC_{50}$ | 24 hr $EC_{50}$ | SI | Log RNA decrease at [μM] |
|---|---|---|---|---|---|
| 89652 | Racemate | >100 | 0.3 | 322.6 | 0.95 @ 20 μM |
| 89652 | Resynthesized racemate | >100 | 1.8 | 55.6 | 1.27 @ 20 μM |
| 80977 | Enantiomer 1 | >100 | >25 | NA | No activity |
| 80978 | Enantiomer 2 | >100 | 1.8 | 55.6 | 1.16 @ 20 μM |

Inhibition of HCV replication by compound AP0080978 (enantiomer 2 from Example 1) was also assayed by exposing cells harboring either HCV genotype 1a, HCV genotype 1b, HCV genotype 2a replicons. To generate EC50 values in Clone VI cells, cells were seeded in the absence of Geneticin™ (Invitrogen, Carlsbad, Calif., USA) into 12-well plates (40,000 cells per well) and treated four hours later with compound by using five point 3-fold serial dilution series with three replicate treatments per dose. Final DMSO percentage was 1% in a total volume of 1 ml. After a 72 hour treatment period, total RNA was extracted, quantified via RiboGreen™ assay (Invitrogen-Molecular Probes, Eugene, Oreg., USA), and equivalent amounts of RNA were subjected to quantitative RT-PCR to quantify HCV RNA levels. Activity against genotype 1b was re-confirmed using Clone II cells (U.S. Pat. No. 7,049,428) that contain a stable subgenomic replicon (Con1 strain) with a Arg 1164 Gly adaptive mutation that is distinct from the Ser 1179 Ile adaptive mutation present in Clone VI cells. In this assay, cells were seeded into 96-well plates and treated in quadruplicate with varying concentration of compounds for 72 hours. For each replicate culture, HCV RNA levels were measured by blot hybridization and normalized to β-actin RNA levels. Cytotoxicity was measured using an established neutral red dye uptake assay (Korba and Gerin (1992) Antiviral Res 19:55; Okuse et al (2005) Antiviral Res 65: 23). This same method was used to evaluate the efficacy and toxicity of 80978 against Huh7.5 cells containing the genotype 1a replicon H/FL-Neo(L+I) derived from the H77 strain (Blight et al, (2003) J Virol 77: 3181). Activity and toxicity against genotype 2a was evaluated in Huh7 cells harboring a stable hRluc-containing subgenomic genotype 2a replicon containing sequence from both J6 and JFH1 strains. Cells were seeded in the absence of Geneticin™ (Invitrogen) into 96-well plates at 12,000 cells per well in medium containing 10% FBS, 1× penicillin/streptomycin, 1× non-essential amino acids, and Fungizone (100 ng/ml). After a four hour attachment period, compound was added to wells using a five point 3-fold serial dilution series with four replicate treatments per dose. Final DMSO percentage was 1% in a total volume of 2004 Compound-mediated HCV inhibition ($EC_{50}$) and toxicity $CC_{50}$ were assayed 48 hours post-treatment using Renilla luciferase readout and the ATP viability assay (CellTiter-Glo, Promega), respectively. Both $EC_{50}$ (i.e. concentrations at which a 50% reduction in replicon levels is observed relative to an untreated control) and $CC_{50}$ (i.e. concentration resulting in a 50% decrease in cell viability) values were determined). The results of these experiments are provided in Table 2.

TABLE 2

Inhibition of HCV replication by 80978 (Enantiomer 2)

| Experiment | HCV Genotype | Assay | EC50 (uM) | CC50 (uM) |
|---|---|---|---|---|
| 1 | 1b | RT-PCR | 0.9-1.75 | >100 |
| 2 | 2a | Renilla Luciferase | >25 | |
| 3 | 1b | Northern Blot | 7.3 | >20 |
| 4 | 1a | Northern Blot | 7.8 | |

Generation of 80978-resistant HCV Replicons:

In an effort to gain insight into the target of 80978, Clone A cells were selected for resistance to 80978. Clone A cells are a human hepatoma cell line that contains a stable genotype 1b (Con1 strain) subgenomic replicon. Cells were cultured for 12 days in medium containing 10 μM 80978 and 1 mg/ml Geneticin™ (Invitrogen). Medium was changed every 3-4 days to replenish compound, and cells were split as needed to maintain subconfluent cultures. After 12 days of growth in the presence of 10 μM 80978, the concentration of 80978 was increased to 20 μM and cultured for an additional 19 days. Control Clone A cells were grown in parallel in the presence of diluent only. After this culture period, cells were evaluated for response to 80978.

Control cells and cells that had been cultured in the presence of 80978 were treated in triplicate with 3-fold serial dilutions of compound for 72 hours. At the end of this incubation period, total RNA was extracted, and HCV RNA levels were measured by quantitative RT-PCR using primers that recognize the 3'NTR. Clone A cells that had been cultured in the presence of 80978 exhibited a substantial decrease in sensitivity to 80978 relative to the control cells (80978-resistant cells, $EC_{50}$>25 μM; control cells, $EC_{50}$=1.76 μM).

To determine whether resistance was replicon-associated, total RNA was extracted from 80978-resistant and control cells and re-introduced via electroporation into naïve Huh7b cells, the parental cell line of Clone A cells. Electroporated cells that harbored replicon were selected with Geneticin™, pooled, and assayed for sensitivity to 80978. Cells electroporated with total RNA from control cells were sensitive to 80978, while those electroporated with total RNA from 80978-resistant cells maintained resistance to the compound, indicating that the resistance was replicon-associated.

To identify nucleotide changes that confer resistance to 80978, replicon RNA was reverse transcribed and amplified from total RNA extracted from 80978-resistant and control Clone A cells. Sequence analysis of the amplified replicon revealed three mutations present within the sequence encoding NS4B from the 80978-resistant cells that were not present within the control or wild type replicon sequence. These mutations resulted in amino acid changes corresponding to F1809L, F1809V, and S1949Y substitutions in the NS4B protein encoded by these mutants (amino acids are numbered according to the full-length genotype 1b (Con1 strain) HCV genome provided as SEQ ID NO:9 and also available under the NCBI accession number Q9WMX2). One silent mutation at amino acid 1771 was also observed. Each mutation was introduced independently into a stable genotype 1b (Con1 strain) subgenomic reporter replicon plasmid via site-directed mutagenesis. Sequencing of the resulting plasmids revealed that they were void of additional mutations. The sequence of the wild type NS4B encoding sequence is provided as SEQ ID NO:1, the sequence of the mutated NS4B nucleotide sequence encoding the F1809V mutation is provided as SEQ ID NO:3, and the sequence of the mutated NS4B nucleotide sequence encoding the F1809L mutation is provided as SEQ ID NO:5. The sequence of the wild type NS4B protein is provided as SEQ ID NO:2, the sequence of the mutated NS4B protein with the F1809V mutation is provided as SEQ ID NO:4, and the sequence of the mutated NS4B nucleotide sequence encoding the F1809L mutation is provided as SEQ ID NO:6. In vitro transcribed (IVT) RNA generated from each mutant and parental replicon cDNAs was introduced into Huh7.5 cells, a highly permissive human hepatoma cell line, and evaluated for response to 80978 and the positive control compound cyclosporin A (CsA). Cells electroporated with in vitro transcribed RNA from each construct were responsive to CsA ($EC_{50}$ values ranged from 0.1 to 0.16 uM). A differential response was observed between cells electroporated with different replicon RNAs. Cells containing replicons with F1809V and F1809L mutations were resistant to 80978 (for both, EC50 values >22.5 uM), while those containing parental replicon, the S1949Y mutation, or the silent mutation remained sensitive to 80978 ($EC_{50}$=0.29, 0.41, 0.24, respectively), suggesting that NS4B is the target of 80978 and that changing the amino acid at residue 1809 to either valine or leucine is sufficient to confer resistance to the compound.

Example 3

Identification of the Region of Genotype 1b NS4B/Replicon that Confers Sensitivity to 80978

That NS4B is the target of 80978 was confirmed by a complementary approach. The differential response to 80978 by HCV genotype 1b and 2a replicons allowed the use of chimeric replicons to narrow down the region of the HCV genotype 1b NS4B coding region that confers sensitivity to 80978. The nucleotide sequence of the wild type HCV genotype 2a NS4B is provided as SEQ ID NO: 7 and the wild type HCV genotype 2a NS4B protein sequence is provided as SEQ ID NO:8. Using a plasmid containing an 80978-resistant stable HCV genotype 2a subgenomic reporter replicon cDNA, six replacement, or chimeric constructs were made, where the regions encoding the following amino acids of NS4B were replaced with the regions encoding the corresponding amino acids of NS4B from HCV genotype 1b: (i) 7-254, (ii) 7-52, (iii) 53-254, (iv) 219-254, (v) 7-52 and 219-254, and (vi) 53 to 218. The full-length NS4B protein is 261 amino acids in length and is provided as SEQ ID NO:2. Thus, if any of these segments of NS4B from genotype 1b are sufficient to confer 80978-sensitivity to a genotype 2a HCV replicon, it will render the chimeric genotype 1b/genotype 2a replicon sensitive to the compound.

In vitro transcribed (IVT) RNA generated from each of the six chimeric replicon cDNAs as well as the genotype 2a parental replicon was electroporated into Huh7.5 cells and evaluated for their response to 80978 and CsA. The chimeric replicon that contained the nearly full-length NS4B from genotype 1b (amino acids 7-254) did not replicate, while the remaining chimeric replicons replicated to varying degrees based on reporter gene expression levels in cells up to 96 hours post-electroporation that had not yet been selected with Geneticin™. Response to 80978 was measured initially in unselected cells. Two chimeric replicons that encoded either the genotype 1b amino acids 53-254 or the genotype 1b amino acids 53 to 218 were responsive (i.e. sensitive) to 80978, with $EC_{50}$ values less than 2.5 μM. All other chimeric replicons, as well as the genotype 2a parental replicon, generated $EC_{50}$ values for 80978 that were greater than 20 indicating that these chimeric replicons were insensitive to 80978. All of the chimeric and wild type control constructs were responsive to Cyclosporin A (CsA).

Cells harboring replicons were selected with Geneticin™ and pooled, and response to 80978 and CsA was measured in these stable replicon-containing cells. These data were consistent with data gathered using unselected cells in which two "swap" replicons—one encoding genotype 1b amino acids 53-254 and the other encoding genotype 1b amino acids 53-218—were responsive to 80978, while other "swap" replicons and the parental genotype 2a replicon were not. These data complement the resistance data, which demonstrated that an amino acid residue within this "swap" region (phenylalanine at residue 1809) when mutated to either valine or leucine renders an 80978-sensitive genotype 1b replicon resistant to the compound (see above).

Since leucine at amino acid 1809 in the genotype 1b replicon was mutated from a phenylalanine residue to a leucine or a valine residue to confer resistance to 80978, and the residue at the corresponding position in the parental genotype 2a replicon is leucine, mutagenesis was carried out to determine whether a phenylalanine at this position in the genotype 2a replicon was sufficient to confer sensitivity to 80978. The resulting genotype 2a replicon with the L1809F mutation remained resistant to the compound, with an $EC_{50}$ value greater than 25 μM, indicating that a mutation in this residue alone cannot confer 80978 sensitivity to an HCV genotype 2a subgenomic replicon.

Example 4

Additional Compounds of Formula (I) that Inhibit Hepatitis C Viral Replication

Additional compounds of formula (I) shown in FIG. 1 were also shown to inhibit HCV RNA replication. The effects of various compounds of formula (I) on HCV RNA replicon levels were determined by measuring HCV replicon RNA levels in cells treated with various concentrations of the compounds. The previously described Clone VI cell line, a human hepatoma cell line that contains a stable genotype 1b (Con1 strain) subgenomic replicon (U.S. Pat. No. 7,049,428), were used in these experiments. Cells were seeded into 12-well plates (40,000 cells per well) in the absence of Geneticin™ (Invitrogen, Carlsbad, Calif., USA) and treated in triplicate four hours later with 20 μM compound, with a final DMSO percentage of 1% in a total volume of 1 ml. Total RNA was extracted 72 hours later, and HCV and GAPDH RNA levels were quantified via quantitative RT-PCR. The compounds other than 80978 were provided as racemates in these experiments. The log 10 decrease in HCV RNA levels was quantified relative to GAPDH RNA levels using the comparative Ct (threshold cycle) method (Applied Biosystems, Foster City, Calif., USA). To generate EC50 values in Clone VI cells, cells were seeded in the absence of Geneticin™ (Invitrogen, Carlsbad, Calif., USA) into 12-well plates (40,000 cells per well) and treated four hours later with compound by using five point 3-fold serial dilution series with three replicate treatments per dose. Final DMSO percentage was 1% in a total volume of 1 ml. After a 72 hour treatment period, total RNA was extracted, quantified via RiboGreen™ assay (Invitrogen-Molecular Probes, Eugene, Oreg., USA), and equivalent amounts of RNA were subjected to quantitative RT-PCR to quantify HCV RNA levels. Both $EC_{50}$ (i.e. concentrations at which a 50% reduction in HCV replicon levels is observed relative to an untreated control) and $CC_{50}$ (i.e. concentration resulting in a 50% decrease in cell viability) values were determined.

The results of the analysis are provided in FIG. 2. The EC50 values for inhibition of HCV RNA replication of the compounds of formula (I) that were tested ranged from 0.9 micromolar (for 80978; purified enantiomer 2) to about 20 micromolar (for an 80925 racemate).

Certain biological sequences referenced herein by their "NCBI Accession Number" or common names can be accessed through the National Center of Biotechnology Information on the world wide web at http://www.ncbi.nlm-.nik.gov.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

Example 5

Crystal Structure of Active Enantiomer

Analysis of the active enantiomer, Enantiomer 2 (AP0080978), was performed to determine its absolute configuration. Separation of the enantiomers of AP0089652 to AP0080978 and AP0080977 was done as described in Example 1. An enantiopure sample of AP0080978 for analysis was supplied as tiny crystals and was recrystallized by vapor diffusion from chloroform and petroleum ether. These crystals were subjected to X-ray structure analysis. The active enantiomer was determined to be (5S,7R)-3-chloro-5-(furan-2-yl)-N-(thiophene-2-yl-methyl)-7-(trifluoromethly)-4,5,6,7-tetrahydropyrazolo[1,5-a]pyrimidine-2-carboxamide (FIG. 3).

The structural model generated contains a disordered region caused by two different conformations of the thiophene ring in the crystal. No spurious electron density peaks were present in the final difference map between the model and the data. The molecule co-crystallized with a molecule of chloroform solvent, the analysis did not reveal any additional solvent or other molecules incorporated into the crystal structure, and calculations did not detect any solvent-accessible voids within the structure.

The absolute structure parameter, x, (Flack (1983) Acta Cryst. A39, 876-881) has a standard uncertainty, u, of 0.06, and a refined value of x=−0.01. x=0.0 indicates that the refined structure matches the enantiomer in the sample, and x=1.0 indicates the refined structure is the inverse of the enantiomer in the sample. A standard uncertainty, u, <0.1 is considered sufficient to distinguish enantiomers, provided the material is known a priori to be enantiopure (Flack & Bernardinelli (2000) J. Appl. Cryst. 33, 1143-1148).

Experiment and Analysis—X-ray diffraction data were collected at 150K on a Nonius KappaCCD diffractometer. 5269 independent reflections were measured at or below θ=27.5°, of which 4680 were above the threshold I>2.0σ(I). The unit cell is orthorhombic: a=7.88170(10)Å, b=12.44820(10)Å, c=23.5955(3)Å, α=90°, β=90°, γ=90°, volume=2315.02(5)Å$^3$. The structure is in space group P2$_1$2$_1$2$_1$, with 4 formula units, C$_{17}$H$_{14}$C$_{11}$F$_3$N$_4$O$_2$S.CHCl$_3$, in the unit cell giving a Z' of 1, and a calculated density of 1.579 Mg m$^{-3}$.

Disorder—Rotation of the thiophene group around the C—C bond connecting it to the molecule gives rise to two different conformations in the crystalline material. This may be a static disorder with 85.7% of the molecules trapped in one conformation and the rest in the other, or it may be a dynamic disorder with the ring constantly flipping between the two positions and favoring the more stable conformation with a population of 85.7%. In either case, the X-ray diffraction experiment measures the structure averaged over all the conformations present in the crystal. The refined model contains a single additional occupancy parameter, such that the occupancy of S16=occupancy of C19=(1−occupancy of S19)=(1−occupancy of C16).

TABLE 3

Crystal Data

| | |
|---|---|
| C$_{18}$ H$_{15}$ Cl$_4$ F$_3$ N$_4$ O$_2$ S$_1$ | Z = 4 |
| M$_r$ = 550.21 | D$_x$ = 1.579 Mg m$^{-3}$ |
| Orthorhombic, P2$_1$2$_1$2$_1$ | Mo Kα |
| a = 7.88170 (10) Å | μ = 0.65 mm$^{-1}$ |
| b = 12.44820 (10) Å | T = 150 K |
| c = 23.5955 (3) Å | Needle, clear colourless |
| V = 2315.02 (5) Å$^3$ | 0.62 × 0.16 × 0.07 mm |

TABLE 4

Data Collection

| | |
|---|---|
| Area diffractometer | 5269 independent reflections |
| ω scans | 4680 reflections with I > 2.0σ(I) |
| Absorption correction: multi-scan DENZO/SCALEPACK (Otwinowski & Minor, 1997) | |
| T$_{min}$ = 0.75, T$_{max}$ = 0.96 | θ$_{min}$ = 27.5° |
| 5269 measured reflections | R$_{int}$ = 0.041 |

TABLE 5

Refinement

| | |
|---|---|
| Refinement on F$^2$ | Chebychev polynomial (Watkin, 1994, Prince, 1982) |
| | w = 1/[A$_0$T$_0$(x) + A$_1$T$_1$(x) . . . + A$_{n-1}$T$_{n-1}$(x)] |
| | where A$_i$ are: 28.9, 45.8, 27.2, 11.5, 2.81 and x = F/F$_{max}$ |
| | Robust modifier: W = [w] * [1 − (ΔF/6*σF)$^2$]$^2$ |
| R[F$^2$ > 2σ(F$^2$)] = 0.040 | (Δ/σ)$_{max}$ = 0.001 |
| wR(F$^2$) = 0.098 | Δρ$_{max}$ = 0.60 e Å$^{-3}$ |
| S = 1.00 | Δρ$_{min}$ = −0.60 e Å$^{-3}$ |
| 5269 reflections | Extinction correction: None |
| 291 parameters | Absolute structure: Flack (1983), 2274 Friedel-pairs |
| H-atom parameters constrained | Flack parameter: −0.01 (6) |

TABLE 6

Selected Geometric Parameters (Å or °)

| | |
|---|---|
| Cl1—C2 | 1.716 (2) |
| C2—C3 | 1.379 (3) |
| C2—C10 | 1.411 (3) |
| C3—N4 | 1.373 (3) |
| C3—N8 | 1.353 (3) |
| N4—C5 | 1.476 (3) |

TABLE 6-continued

Selected Geometric Parameters (Å or °)

| | |
|---|---|
| C5—C6 | 1.526 (4) |
| C5—C24 | 1.487 (4) |
| C6—C7 | 1.533 (4) |
| C7—N8 | 1.470 (3) |
| C7—C20 | 1.518 (4) |
| N8—N9 | 1.355 (3) |
| N9—C10 | 1.344 (3) |
| C10—C11 | 1.479 (3) |
| C11—O12 | 1.235 (3) |
| C11—N13 | 1.340 (3) |
| N13—C14 | 1.465 (3) |
| C14—C15 | 1.499 (4) |
| C15—S16 | 1.718 (3) |
| C15—C19 | 1.439 (4) |
| S16—C17 | 1.682 (3) |
| C16—C17 | 1.682 (4) |
| C17—C18 | 1.352 (5) |
| C18—C19 | 1.479 (4) |
| C20—F21 | 1.327 (3) |
| C20—F22 | 1.341 (3) |
| C20—F23 | 1.347 (3) |
| C24—O25 | 1.373 (3) |
| C24—C28 | 1.347 (4) |
| O25—C26 | 1.366 (4) |
| C26—C27 | 1.334 (5) |
| C27—C28 | 1.430 (5) |
| Cl29—C30 | 1.752 (4) |
| C30—Cl31 | 1.746 (4) |
| C30—Cl32 | 1.747 (3) |
| Cl1—C2—C3 | 123.29 (19) |
| Cl1—C2—C10 | 130.94 (18) |
| C3—C2—C10 | 105.8 (2) |
| C2—C3—N4 | 130.6 (2) |
| C2—C3—N8 | 105.8 (2) |
| N4—C3—N8 | 123.5 (2) |
| C3—N4—C5 | 115.8 (2) |
| N4—C5—C6 | 107.9 (2) |
| N4—C5—C24 | 109.0 (2) |
| C6—C5—C24 | 112.6 (2) |
| C5—C6—C7 | 111.0 (2) |
| C6—C7—N8 | 108.6 (2) |
| C6—C7—C20 | 110.1 (2) |
| N8—C7—C20 | 110.5 (2) |
| C7—N8—C3 | 122.8 (2) |
| C7—N8—N9 | 123.3 (2) |
| C3—N8—N9 | 113.29 (19) |
| N8—N9—C10 | 104.3 (2) |
| C2—C10—N9 | 110.7 (2) |
| C2—C10—C11 | 128.4 (2) |
| N9—C10—C11 | 120.9 (2) |
| C10—C11—O12 | 121.1 (2) |
| C10—C11—N13 | 116.1 (2) |
| O12—C11—N13 | 122.8 (2) |
| C11—N13—C14 | 121.5 (2) |
| N13—C14—C15 | 115.1 (2) |
| C14—C15—S16 | 122.8 (2) |
| C14—C15—C19 | 124.4 (2) |
| S16—C15—C19 | 112.8 (2) |
| C15—S16—C17 | 92.83 (16) |
| C15—C16—C17 | 92.83 (16) |
| S16—C17—C18 | 112.9 (3) |
| C17—C18—C19 | 114.7 (3) |
| C18—C19—C15 | 106.7 (2) |
| C18—S19—C15 | 106.7 (2) |
| C7—C20—F21 | 113.2 (2) |
| C7—C20—F22 | 113.4 (2) |
| F21—C20—F22 | 107.7 (2) |
| C7—C20—F23 | 109.0 (2) |
| F21—C20—F23 | 107.1 (2) |
| F22—C20—F23 | 106.0 (2) |
| C5—C24—O25 | 116.4 (2) |
| C5—C24—C28 | 113.6 (3) |
| O25—C24—C28 | 110.0 (3) |
| C24—O25—C26 | 106.3 (2) |
| O25—C26—C27 | 110.7 (3) |
| C26—C27—C28 | 106.6 (3) |
| C27—C28—C24 | 106.4 (3) |
| Cl29—C30—Cl31 | 110.9 (2) |

TABLE 6-continued

| Selected Geometric Parameters (Å or °) | |
|---|---|
| Cl29—C30—Cl32 | 109.34 (19) |
| Cl31—C30—Cl32 | 112.4 (2) |

Refinement details—The H atoms were placed at expected positions and initially refined with soft restraints on the bond lengths and angles to regularize their geometry (C—H in the range 0.93-0.98, Å) and $U_{iso}(H)$ (in the range 1.2-1.5 times $U_{eq}$ of the parent atom), after which their positions were constrained to refine with the positions of the heavier atoms. An occupancy parameter was refined to model the some positional disorder in a ring, the positions of S16 and C16 were constrained to be identical, and similarly for S19 and C19.

Software—Data collection: COLLECT (Nonius (1997-2001).COLLECT. Nonius BV, Delft, The Netherlands); cell refinement: DENZO/SCALEPACK (Otwinowski & Minor (1997) *Methods in Enzymology*, Vol. 276, edited by C. W. Carter Jr & R. M. Sweet, pp. 307-326. New York Academic Press); data reduction: DENZO/SCALEPACK; program(s) used to solve structure: SIR92 (Altomare et al. (1994) *J. Appl. Cryst.* 27, 435); program(s) used to refine structure: CRYSTALS (Betteridge et al. (2003) *J. Appl. Cryst.* 36, 1487); molecular graphics: CAMERON (Watkin et al. (1996) *CAMERON*, Chemical Crystallography Laboratory, Oxford, UK); software used to prepare material for publication: CRYSTALS.

Example 6

AP0080978 Analog Efficacy Against Infection by HCV in Cell Culture

Figure 4:
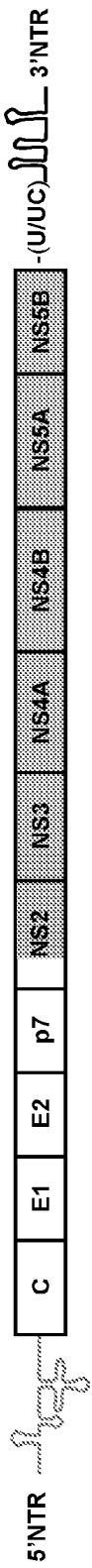
FIG. 4: Resistant and Sensitive Virus Constructs.
Figure 4:
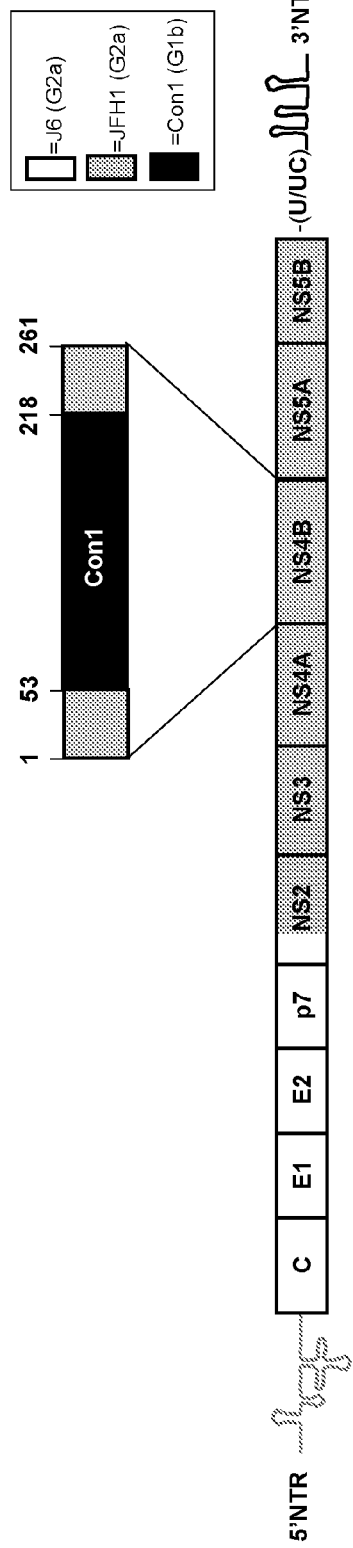

Inhibition of HCV infectivity by AP0080978 and its analogs (AP0080977, non-active enantiomer; AP0089652, racemate; and AP0080935, an aromatic, non-optically active analog of AP0080978) was assayed by exposing cells with infectious chimeric HCV virions in the presence of the compounds. This was accomplished by use of an HCV cell culture system essentially as described in Pietschmann, T. et al. (2006) 103(19): 7408-13, Proc. Natl. Acad. Sci. USA; and elsewhere. Two viral constructs were utilized to characterize inhibition of viral infectivity (FIG. 4). Construct APV23 (FL-J6/JFH) is a full-length, chimeric, genotype 2a HCV genome containing the HCV core through the NS2 first transmembrane domain coding region from the J6 HCV isolate linked to the second NS2 transmembrane domain NS3 through NS5B coding region of HCV strain JFH-1, as shown in FIG. 4 (i.e. an HCV chimera with the "C3 Junction" described in Pietschmann, T. et al. (2006) Proc. Natl. Acad. Sci. USA 103(19): 7408-13; see page 7409 and FIG. 2A of Pietschmann, T. et al.). Construct APV112 was generated by replacing nucleotides encoding amino acids 53 to 218 of the NS4B gene of the APV23 sequence with a corresponding sequence from a genotype 1b (Con1 strain).

Figure 5:
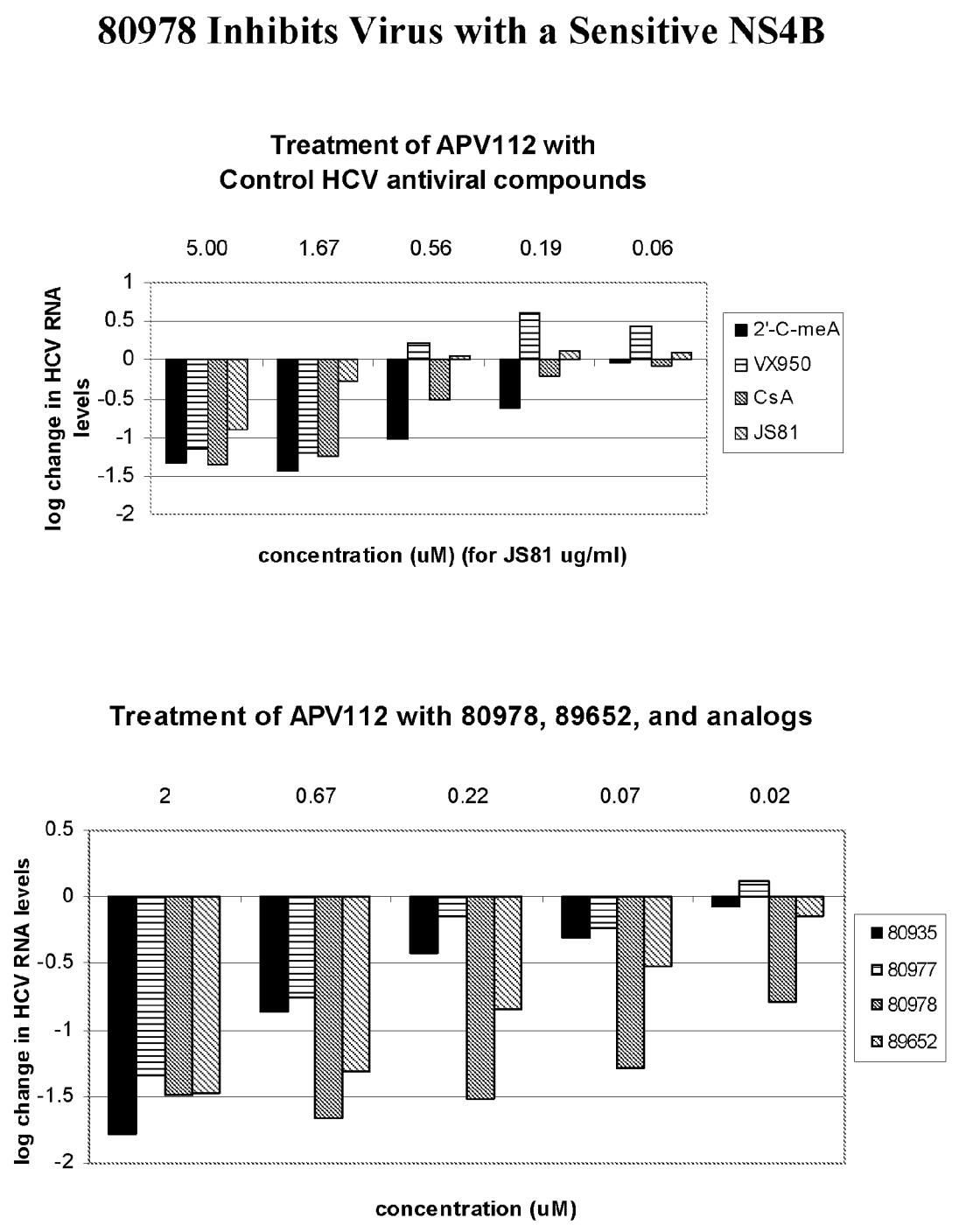

Huh7.5 cells were plated at a density of 20,000 cells per well in 96-well plates. The cells were exposed to the chimeric HCV virions at a multiplicity of infection of 0.01. Potential inhibitory compounds were added simultaneously with the chimeric virus. Cells were incubated for 48 hours and then the levels of HCV 3'NTR and GAPDH RNA were quantified by realtime quantitative PCR. Data were analyzed by the comparative Ct method with delta-delta Ct determined relative to 1.0% DMSO. Results in FIGS. 5 and 6 are depicted as log change in 3'NTR copies relative to 1.0% DMSO.

Chimeric APV23 viral infectivity was unaffected by AP0080978 and AP0089652 (FIG. 6), indicating that this chimeric HCV that contained a genotype 2a NS4b coding region was resistant to these compounds. However, the chimeric APV112 viral infectivity was reduced by AP0080978 and AP0089652 (FIG. 5), indicating that this chimeric HCV that contained a genotype 1b NS4b coding region was sensitive to these compounds. Thus, NS4B appears to be a potential target of AP0080978 and AP0089652. Further, AP0080978 and AP0089652 appear to be significantly more potent in these viral infectivity assays than in HCV replicon assays. AP0080978 is significantly more potent in the HCV APV112 viral infectivity assay than the control HCV inhibitors 2'-C-methyl-adenosine (2'CMeA), VX-950, cyclosporin A, and a-CD81 antibody (JS81) (FIG. 5). The GAPDH normalized numerical log change data for AP0080978, AP0089652, AP0080935, and AP0080978 shown in the FIG. 5 graph are provided below in Table 7. At 0.02 µM, the purified enantiomer 80978 exhibits a 5.3-fold greater log change (i.e. GAPDH normalized decrease in HCV RNA comprising the 3' NTR) relative to the log change associated with the 89652 racemate

TABLE 7

| Log Change Data for AP80978 and Analogs | | | | |
|---|---|---|---|---|
| Concentration | Compound Number | | | |
| (µM) | 80935 | 80977 | 80978 | 89652 |
| 2 | −1.78 | −1.34 | −1.49 | −1.47 |
| 0.67 | −0.86 | −0.75 | −1.67 | −1.31 |
| 0.22 | −0.42 | −0.15 | −1.52 | −0.85 |
| 0.07 | −0.3 | −0.23 | −1.29 | −0.52 |
| 0.02 | −0.07 | 0.12 | −0.79 | −0.15 |

What is claimed is:

1. A method of treating a hepatitis C viral infection in a subject in need thereof, said method comprising administering to said subject a pharmaceutical composition that comprises a therapeutically effective amount of an enantiomer that inhibits hepatitis C viral replication having the formula (I):

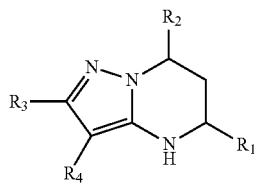

or a pharmaceutically acceptable salt thereof, wherein:
$R_1$ is selected from the group consisting of unsubstituted thienyl-2 and unsubstituted furyl-2;
$R_2$ is selected from the group consisting of —$CCl_3$, —$CBr_3$, and —$CF_3$;
$R_3$ is —$CONHR''3$, wherein R''3 is meta-hydroxyalkyl substituted phenyl, or —(X)—R, wherein X is —$(CH_2)_n$—, wherein n is 1 or 2, and wherein R is a unsubstituted thienyl-2 and unsubstituted furyl-2 group;
$R_4$ is selected from the group consisting of hydrogen, chloro, bromo, and fluoro;
and wherein said compound or salt thereof is an enantiomer with $R_1$ and $R_2$ in a syn configuration that inhibits hepatitis C viral replication,
thereby treating said hepatitis C viral infection in said subject.

2. The method of claim 1, wherein the subject is a human.

3. The method of claim 1, wherein the pharmaceutical composition can be administered in combination, either concurrently or sequentially, with at least one additional biologically active agent selected from the group consisting of immunomodulators, hepatoprotectants, anti-inflammatory agents, antibiotics, and antivirals.

4. The method of claim 3, wherein at least one agent of said at least one additional biologically active agent is an antiviral agent selected from the group consisting of interferon, pegylated interferon, ribavirin, viral protease inhibitors, viral polymerase inhibitors, antiviral small interfering RNA compounds, anti-sense antiviral compounds, nucleotide analogs, nucleoside analogs, and immunoglobulins.

5. The method of treating a hepatitis C viral infection of claim 1, wherein said enantiomer with $R_1$ and $R_2$ in a syn configuration that inhibits hepatitis C viral replication has the structure:

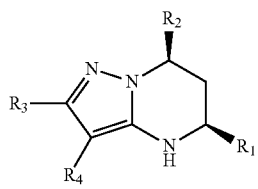

and wherein:

R₁ is unsubstituted furyl-2; R₂ is a polyhaloalkyl selected from the group consisting of —CCl₃, —CBr₃, and —CF₃; R₃ is is —CONHR"3, wherein R"3 is meta-hydroxyalkyl substituted, or —(X)—R, wherein X is —(CH₂)$_n$—, wherein n is 1 or 2, and wherein R is a unsubstituted thienyl-2 and unsubstituted furyl-2;

and R₄ is hydrogen, chloro, bromo, or fluoro.

6. The method of treating a hepatitis C viral infection of claim 5, wherein said enantiomer has the structure:

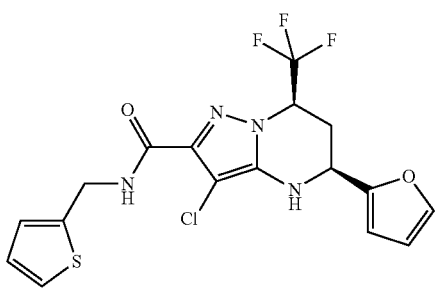 [SMILES: O=C(NCc1cccs1)c1nn2c(c1Cl)N[C@H](c1ccco1)C[C@@H]2C(F)(F)F]

or is a pharmaceutically acceptable salt thereof.

* * * * *